(12) United States Patent
Xin et al.

(10) Patent No.: US 7,795,407 B2
(45) Date of Patent: Sep. 14, 2010

(54) METASTATIC BREAST AND COLON CANCER REGULATED GENES

(75) Inventors: Hong Xin, Emeryville, CA (US); Klaus Giese, San Francisco, CA (US)

(73) Assignee: Novartis Vaccines and Diagnostics, Inc., Emeryville, CA (US)

( * ) Notice: Subject to any disclaimer, the term of this patent is extended or adjusted under 35 U.S.C. 154(b) by 0 days.

(21) Appl. No.: 11/657,337

(22) Filed: Jan. 24, 2007

(65) Prior Publication Data

US 2007/0178509 A1 Aug. 2, 2007

Related U.S. Application Data

(60) Division of application No. 10/601,091, filed on Jun. 19, 2003, now Pat. No. 7,279,307, which is a continuation of application No. 09/215,450, filed on Dec. 17, 1998, now Pat. No. 6,635,748.

(60) Provisional application No. 60/070,112, filed on Dec. 31, 1997.

(51) Int. Cl.
*C12N 15/11* (2006.01)
(52) U.S. Cl. .......................... 536/23.1; 435/6
(58) Field of Classification Search ................ None
See application file for complete search history.

(56) References Cited

U.S. PATENT DOCUMENTS

| | | | |
|---|---|---|---|
| 5,514,558 A | 5/1996 | Ceriani et al. | 435/7.92 |
| 5,658,784 A | 8/1997 | Eckner et al. | 435/325 |
| 5,994,104 A | 11/1999 | Anderson et al. | 435/69.52 |
| 6,025,180 A | 2/2000 | Powell et al. | 435/219 |
| 6,635,748 B2 | 10/2003 | Xin et al. | |
| 7,279,307 B2 | 10/2007 | Giese et al. | |

FOREIGN PATENT DOCUMENTS

| | | |
|---|---|---|
| EP | 0786519 | 7/1997 |
| EP | 0848062 A2 | 6/1998 |
| JP | 11-069981 A | 3/1999 |
| WO | WO-91/04328 | 4/1991 |
| WO | WO-96/01320 | 1/1996 |
| WO | WO-96/30511 | 10/1996 |
| WO | WO-96/40769 | 12/1996 |
| WO | WO-98/39448 | 9/1998 |
| WO | WO-99/33963 | 7/1999 |
| WO | WO-00/17369 | 3/2000 |
| WO | WO-02-22660 A2 * | 3/2002 |

OTHER PUBLICATIONS

Hillier et al, GenBank® Accession No. N34471 (Jan. 16, 1996).*
Pharmacia P-L Biochemicals 1984 Product Reference Guide, p. 56.*
Kennell, Progr. Nucl. Acid Res. Mol. Biol. 11: 259 (1971).*
Bonaldo et al., Genome Res., 6(9):791, 1996.
Hillier et al., Genome Res., 6(9):807, 1996.
Adams et al., Nature 377 (Supp), 3 Abstract only, 1995.
Wallace et al., Methods Enzymol., 152:432, 1987.
Duffy, *Proteases as Prognostic Markers in Cancer*, Clinical Cancer Research, 2:613-618, 1996.
Chen et al., *Membrane Proteases as Potential Diagnostic and Therapeutic Targets for Breast Malignancy*, Breast Cancer Research and Treatment, 31:217-226, 1994.
Hillier, L., et al., "zb44h05.r1", accession No. W20360, Database SRS [online] EBI; May 5, 1996 (abstract).
Adams, M. D., et al., "Use of human BAC End sequences for Sequence-Ready Map Building", accession No. AQ198349, Database SRS [online] EBI; Sep, 23, 1998 (abstract).
Alpan, R. S. et al. (Jul. 1996). "Identification of mRNAs Differentially Expressed in Quiescence or in Late G1 Phase of the Cell Cycle in Human Breast Cancer Cells by Using the Differential Display Method," *Molecular Medicine* 2(4):469-478.
Anisowicz, A. et al. (Sep. 1996). "A Novel Protease Homolog Differentially Expressed in Breast and Ovarian Cancer," *Molecular Medicine* 2(5):624-636.
EMBL Accession No. AA293614, last updated Aug. 31, 2006, located at <http://www.ebi.ac.uk/cgi-bin/emblfetch?style=html&id=AA293614&Submit=Go> visited on Jan. 9, 2009. (2 pages).
EMBL Accession No. AA630313, last updated Mar. 3, 2000, located at <http://www.ebi.ac.uk/cgi-bin/emblfetch?style=html&id=AA630313&Submit=Go> visited on Jan. 9, 2009. (2 pages).
EMBL Accession No. N46495, last updated Mar. 4, 2000, located at <http://www.ebi.ac.uk/cgi-bin/emblfetch?style=html&id=N46495&Submit=Go> visited on Jan. 9, 2009. (2 pages).
European Search Report mailed Jun. 16, 2004, for EP Application No. 98964933.0 filed Dec. 24, 1998, 4 pages.
GenBank Accession No. AA056282, last updated Nov. 29, 1996, located at <http://www.ncbi.nlm.nih.gov/entrez/viewer.fcgi?list_uids=1548686&db=nucest&dopt=gbwithparts> visited on Jan. 9, 2009. (2 pages).
International Search Report mailed Jun. 7, 1999, for PCT Application No. PCT/US98/26547 filed Dec. 14, 1998, 3 pages.
International Search Report mailed Sep. 17, 1999, for PCT Application No. PCT/US98/27608 filed Dec. 24, 1998, 8 pages.
Liu, Z. et al. (Feb. 13, 1997). "Differential Display of Reticulocalbin in the Highly Invasive Cell Line, MDA-MB-435, Versus the Poorly Invasive Cell Line, MCF-7," *Biochemical and Biophysical Research Communications* 231(2):283-289.
Partial European Search Report and Search Opinion mailed Jan. 23, 2007, for EP Application No. 06003362.8 filed Dec. 24, 1998, 17 pages.
Partial European Search Report and Search Opinion mailed Nov. 3, 2006, for EP Application No. 06003362.8 filed Dec. 24, 1998, 9 pages.

* cited by examiner

Primary Examiner—James Martinell
(74) Attorney, Agent, or Firm—Mark Seka; Patricia Tsao

(57) ABSTRACT

Gene sequences as shown in SEQ ID NO:1-18 have been discovered and isolated, and found to be significantly associated with metastatic spread of breast and colon cancer cells to other organs. Methods are provided for determining the risk of metastasis of a breast or colon tumor, which involve determining whether a tissue sample from a tumor expresses a polypeptide encoded by a gene as shown in SEQ ID NOS:1-18, or a substantial portion thereof. One of the gene sequences encodes a novel aspartyl protease termed CSP56, which can be used to provide reagents and methods for determining which tumors are likely to metastasize and for suppressing metastases of these tumors. Clinicians can use this information to predict which tumors will metastasize to other organs and to provide relevant therapies to appropriate patients.

7 Claims, 10 Drawing Sheets

FIG. 2A-1

```
AGGCACGAGGCCCCGCGGCCGAGTCGCTGAGCGCGGCCGGACGGGACCGGCTAGGCTGGGCCCCCCGGGCGCGTGGGC         100
ATGGGCGCACTGGCCCGGGCCCTGCTGCTGCCCCTGCTGGCCCAGTGGCTGCTGCGCGCGCCCGAGCTGGCTCCC         200
 M  G  A  L  A  R  A  L  L  L  P  L  L  A  Q  W  L  L  R  A  A P E L A P                33
                                                                  P F T L P L
GGGTGGCCCCGGCCACGAACCGCGTAGTTGCCCGGGACCCGGACCCCTGGCGCTGGCCCTGGAGCCTGC                  300
 R V A A A T N R V V A P T G P T P A E R H A D G L A L E P A                             66
CCTGCCGTCCGCGCTACCCGCGCCCAACTTCTGGCCATGTAGACAACCTGCAGGGGGACTCTGGCCGGGGACC              400
 L A S P A G A A N F L A M V D N L Q G D S G R G                                         99
TACTACCTGGAGATGCTGATCGGGACC
CCCCGCAGAAGCTACAGATTCTGTTGACACTGGAAGCAGTAACTTTGCGGTGGCAGGAACCCGACTTGACAGAGA           500
 P P Q K L Q L L V D T G S S N F A V A G T P H S Y I D T Y F D T E                       132
GGTCTAGCACATACCGCTCCAAGGGCTTTGACGTCACAGTGAAGTACACACAAGGAAGCTGGACGGGGTCTTCGTGG          600
 R S S T Y R S K G F D V T V K Y T Q G S W T G F V G E D L V T I P K                     165
AGGCTTCAATATTCTCTTCTGTCAACATTGCCACTATTTTTGAATCAGAGAATTTCTTTTTGCCTGGGATTAAATGAATACTTGGCCTAGCT 700
 R S T Y R S K G F D V T V K Y T Q G S W T G F V G E D L V T I P K                       198
 G F N T S F L V N I A T I F E S E N F F L P G I K W N G I L G L A
TATGCCACACTTGCCAAGCCATCAAGTCCTGAGACCTTCTTCGACTCCCTGGTGACACAAGCAAACATCCCAACGTTTCTCATGCAGATGTGTG 800
 Y A T L A K P S S S L E T F F D S L V T Q A N I P N V F S M Q M C                       231
GAGCCGGCTTGCCCGTCGTGCGATCTGGGACCAACGGAGGTAGTCTTGTGCTTGGGGTGATTGGGATTGAACCAAGTTTGTATAAAGGAGACATCTGGTATACCCC 900
 G A G L P V A G S G T N G G S L V L G G I E P S L Y K G D I W Y T P                     264
```

FIG. 2A-2

```
TATTAAGGAAGAGTGGTACTACCAGATAGAAATTCTGAAATTGGAGGCCAAAGCCTTAATCTGGACTGCAGAGATATAACGCAGACAAGGCC   1000
 I  K  E  E  W  Y  Y  Q  I  E  I  L  K  L  E  I  G  G  Q  S  L  N  L  D  C  R  E  Y  N  A  D  K  A    297
ATCGTGGACAGTGGCACCACGCTGCTGCGCCTGCCCCAGAAGGTGTTTGATGCGGTGTGAAGCTGTGGAAGCGCTGTGCCGCGCATCTGATTCAGAATTCTCTG   1100
 L  V  D  S  G  T  T  L  L  R  L  P  Q  K  V  F  D  A  V  V  E  A  V  A  R  A  S  L  I  P  E  F  S    330
ATGGTTTCTGGACTGGTCCCAGCTGCGCTGCAGAATTCGGACGAACACCTTGGTCTTCTTACTTCCGAAATCTCATCTGAGAGATGAGAACTC   1200
 D  G  F  W  T  G  S  Q  L  A  C  W  T  N  S  E  T  P  W  S  Y  F  P  K  I  S  I  Y  L  R  D  E  N  S    363
CAGCAGGTCATTCCGTATCACAATCTGCTCAGCTTACATTCAGCCGGCCTGAATTATGAATGTTACGCATTCGGCATTCCCCA   1300
 S  R  S  F  R  I  T  I  L  P  Q  L  Y  I  Q  P  M  M  G  A  G  L  N  Y  E  C  Y  R  F  G  I  S  P    396
TCCACAAATGCGCTGGTGATCGGTGCCACGGTGATGGAGGGCTTCTACGTGATCTTCGACAGAGCCCAGAAGAGGGTTGGCTTCGCAGCGAGCCCCTGTG   1400
 S  T  N  A  L  V  I  G  A  T  V  M  E  G  F  Y  V  I  F  D  R  A  Q  K  R  V  G  F  A  A  S  P  C    429
CAGAAATTCAGGTGCAGTGTCAGTGTCTGAAATTCCGGGCTTCACTGAAGATGTAGCCAGCAATGTGTCCCCGGCTCAGTCTTGAGCGAGCCCAT   1500
 A  E  I  A  G  A  A  V  S  E  I  S  G  P  F  S  T  E  D  V  A  S  N  C  V  P  A  Q  S  L  S  E  P  I    462
TTTGTGGATTGTGTCCTATGCGCTCATGAGCGTCTGTGAAGCCATCCTCCTTGTCTTAATCGTCCGTTCCGTTGTGCAGCTGCCCC   1600
 L  W  I  V  S  Y  A  L  M  S  V  C  G  A  I  L  L  V  L  L  L  P  F  R  C  Q  R  R  P    495
CGTGACCCTGAGTCGTCAATGATGAGTCCTCTCGTCAGACATGCTGAAATGAATAGCCAGGCCTGACCTGCAAGCAACCATGAACTCAGCTATTAA   1700
 R  D  P  E  V  V  N  D  E  S  S  L  V  R  H  R  W  K  *    513
GAAAATCACATTTCCAGGCAGCAGCCGGATGATGGTGGCGCTTTCTCTGTGCCACCCGTCTTCAATCTCTGTTCTCCCAGATGCCTTCTAGA   1800
TTCACTGTCTTTTGATTCTTGAAGCTTTGATTTTCAAGCTTTCAAATCCTCCCTACTTCCAAG(A)n   1855
```

FIG. 2B

```
AAAAAAAAACTTCATTCTAAACCAAAACAGAGTGGATTGGGCTGCAGGCTCTATGGGTTCGTTATGCCAAAGTGTCTACATGTCCACCAACATAAA      1955
CAAAACCAAGCCTTGGCTCGTTCTGTCTCTTCCAATCTCTGGAAAATACATAAGTTGATAACCCCTTAGCTTACAGGAGAAGCTTTTGTAT         2055
TAATTGCCTTTGAGGTTATTTCCGCAGACCTCAACCTGGGTCAAGTGGTACAGGAAGGCTTGCAGTATGATGGAGGAATCAGCCTGGGCCTGG        2155
GGATGTAACCAAGCTGTACCCTTGAGACCTGGAACCAGAGCCACAGCCCTTTGTGTGGTTCTCTGTCCTGAATGGGAGCCAGAATTCACTAGAG      2255
GTCATCAACCGATGGTCCTCACAAGGCCCTCTGAAGATGAAGGCCTTTGAGGTAGAGGGAAGAAATCTCTCTTTTGTACCAATACT             2355
TATGTTGTATTGTGGAAAGTAAAACACTACCCTCTTTTGAGACTTTGCCCAGGGTCCTGTGCCTGATGGGGTGCAGGCAGCCTTGACCACGGC       2455
TGTTCCCCTACCCAAAGAATTATCATCCAACAGCCAAGACCCAAGACTGTGCATGAACTGTGAACTGTCCATCAACAGGAGAAGAGTTCTATCCCAAGCTGGCCAC   2555
TATCACATATGCTTACTCTTGCTTAAAATTAATAAATCATGTTTTGATGAG(A)n   2606
```

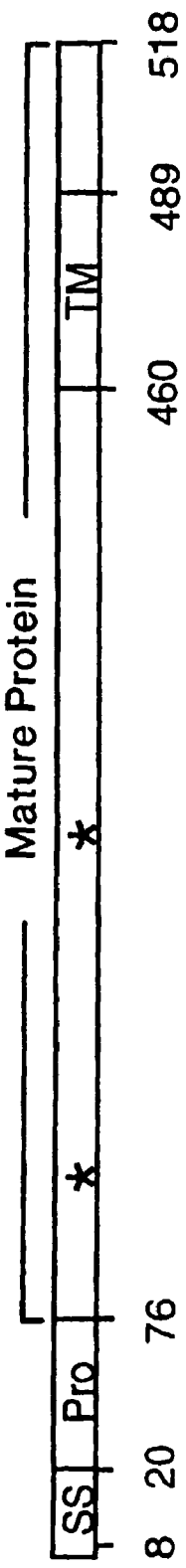

```
CatE    . . . . . . . . . . . . . . MKTL LLLLVL . . LELGEAQGS LHRVPLRRHP SLKKK    35
PepA    . . . . . . . . . . . . . . MKWL LLLGLVA. . L . . . . . SECI MYKVPLIKKK SLRRT    31
PepC    . . . . . . . . . . . . . . . . M KWVVL . . VCLQLLAAP. . VVKVPLKKFK SIFET    32
CatD    . . . . . . . . . . . . . . . QPS SLLPEAL. . CLLAAPASA LVRIPLHKFT SIFRT    35
Renin   . . . . . . . . . . . . MDGWRR MPRW GLLLLWGSC TFGLPTDTTT FKRIFLKRMP SIFES    45
CSP56   . . . . . . . . . MGA ARA LLLPLLAQWL LRAAPELAPA PFTLPLRVAA ATNRV        42

CatE    LRARS QLSEFWKSHN LDMIQ . FTE SCSMDQSAK . EPLINTLDME        77
PepA    LSERG LLKDFLKKHN LNPARKYFPQ WEAPTLVDE . QPLENYLDMA        75
PepC    MKEKG LLGEFLRTHK YDPAWKY . . RFGDLSVTY. EP . . IMDAA        72
CatD    MSEVG GSVEDLIAK . GPVSKYSQA VPAVTEGPIP EVLKNYLDAQ        78
Renin   LKERG VDMARLGPEW SQPMKRL . . TLGNTTSS . VILTNYMDTQ        85
CSP56   VAPTP GPGTPAERHA DGLALALEPA LASPAGAANF LAVDNLQGD         87

CatE    . . IFGTIS IGSPPQNFTV IFDTGSSNLW VPSVYCT. . S . . . PACKT     116
PepA    . . IFGTIH IGTPPQDFTV VFDTGSSNLW VPSVYCS . . . . . . LACTN    114
PepC    . . IFGEIG IGTPPQNFLV LFDTGSSNLW VPSVHCK . . . . . . QACTS    111
CatD    . . IFGEIG IGTPPQCFTV VFDTGSSNLW VPSIHCKLLD IHACWH         117
Renin   . . YYGEIG IGTPPQKFTV LVDTGSSNVM AGT. . . . SRLY . . TACVY   124
CSP56   GRGHYLEML IGTPPQKWTQ . . . . . . .              PHSYI   126

CatE    PSQSSTYSQP QSFSIQYGT GSLSGIHGAD QVS . . . . .    155
PepA    PEDSSTYSTN SETVSLHLR GGSMTGGILGYD QT . . . . .    153
PepC    PSESSTYKN GQTFSLQHIRS GSLSGFFGQD TT . . . . .    150
CatD    SDKSSTYVKN GTSFDIHYGS GGSLGGYLSQD T . . . PCQSAS 164
Renin   ASDSSYKHN GTELTLRIST GSWTGFVGED LTLPKGFNT        171
```

CatE    V.PDVTFTIN GVPYTLSPTA .TLDFVDGM QFCSSGFQGL DIHPP  363
PepA    SLPDDIVFTI HGVVQHPVPSA HHL..QSNNR GSCHSGFQGM NLPTE  356
PepC    NLPSLTVFTI KLGGVKPLPPS HL..SNNAWS GYCLTVGVEPT YLSSQ  355
CatD    TLPAITFTIH KLGGKGYKLSP TAL..KVSQAGK TLCLSGFMGM DIPPP  378
Renin   TLPDISFHLG GKEYTLTSAD HV.QESYSNS KLCTLAIHAM DIPPP  374
CSP56   QLACWTNSET PWSY..PKIS IYLRDENSSR SFRITILPQL YIQPM  384

CatE    AG.PL..... ..........  ..........  NILGD VFIRQFYSVF DFGNNEVG  392
PepA    SG.EL..... ..........  ..........  NILGD VFIRQYYTVF DFANQVG  385
PepC    NGQPL..... ..........  ..........  NILGD VFLRSYYTVF DLGNNRVGF  385
CatD    SG.PL..... ..........  ..........  NILGD VFIRQYYTVF DRDNNRVGF  407
Renin   TG.PT..... ..........  ..........  WALGA TFIRKFYTEF DRRNNRGGF  403
CSP56   MGAGL..... PSTNALVEGA TVMEGFIVLF DFAQKRVGF  429

CatE    PAVP...... ..........  ..........  ..........  ..........   396
PepA    PVA....... ..........  ..........  ..........  ..........   388
PepC    TAA.RL.... ..........  ..........  ..........  ..........   388
CatD    EAARL..... ..........  ..........  ..........  ..........   412
Renin   LAR....... ..........  ..........  ..........  ..........   406
CSP56   ASPCAEIAGA AVSEISGPFS TEDVASNCVP AQSLSEPILW IVSYA   474

CatE    .......... ..........  ..........  ..........  ..........   396
PepA    .......... ..........  ..........  ..........  ..........   388
PepC    .......... ..........  ..........  ..........  ..........   388
CatD    .......... ..........  ..........  ..........  ..........   412
Renin   .......... ..........  ..........  ..........  ..........   406
CSP56   LMSVC GAILLVLIVL LLLPFRCQRR PRDPEVVNDE SSLVRHRWK*   518
```

METASTATIC BREAST AND COLON CANCER REGULATED GENES

CROSS-REFERENCE TO RELATED APPLICATIONS

This application is a divisional and claims the benefit of priority under 35 USC §120 of U.S. application Ser. No. 10/601,091, filed Jun. 19, 2003 now U.S. Pat. No. 7,279,307 which is a continuation of U.S. application Ser. No. 09/215,450, filed Dec. 17, 1998 now U.S. Pat. No. 6,635,748 which claims benefit of U.S. application Ser. No. 60/070,112, filed Dec. 31, 1997. All of the preceding applications are expressly incorporated herein by reference in their entireties.

TECHNICAL FIELD OF THE INVENTION

This invention relates to methods for predicting the behavior of tumors and in particular, but not exclusively, to methods in which a tumor sample is examined for expression of a specified gene sequence which indicates propensity for metastatic spread.

BACKGROUND OF THE INVENTION

Despite use of a number of histochemical, genetic, and immunological markers, clinicians still have a difficult time predicting which tumors will metastasize to other organs. Some patients are in need of adjuvant therapy to prevent recurrence and metastasis and others are not. Distinguishing between these subpopulations of patients is not straightforward. Thus the course of treatment is not easily charted. There is therefore a need in the art for new markers for distinguishing between tumors of differing metastatic potential.

SUMMARY OF THE INVENTION

It is an object of the invention to provide reagents and methods for determining which tumors are likely to metastasize and for suppressing metastases of these tumors. These and other objects of the invention are provided by one or more of the embodiments described below.

One embodiment of the invention is an isolated and purified protein having an amino acid sequence which is at least 85% identical to an amino acid sequence encoded by a polynucleotide comprising a nucleotide sequence selected from the group consisting of SEQ ID NOS:1-18. Percent identity is determined using a Smith-Waterman homology search algorithm using an affine gap search with a gap open penalty of 12 and a gap extension penalty of 1.

Another embodiment of the invention is an isolated and purified polypeptide which consists of at least 8 contiguous amino acids of a protein having an amino acid sequence encoded by a polynucleotide comprising a nucleotide sequence selected from the group consisting of SEQ ID NOS:1-18.

Yet another embodiment of the invention is a fusion protein which comprises a first protein segment and a second protein segment fused to each other by means of a peptide bond. The first protein segment consists of at least 8 contiguous amino acids selected from an amino acid sequence encoded by a polynucleotide comprising a nucleotide sequence selected from the group consisting of SEQ ID NOS:1-18.

Still another embodiment of the invention is a preparation of antibodies which specifically bind to a protein with an amino acid sequence encoded by a polynucleotide comprising a nucleotide sequence selected from the group consisting of SEQ ID NOS:1-18.

Even another embodiment of the invention is a cDNA molecule which encodes an isolated and purified protein having an amino acid sequence which is at least 85% identical to an amino acid sequence encoded by a polynucleotide comprising a nucleotide sequence selected from the group consisting of SEQ ID NO:1-18. Percent identity is determined using a Smith-Waterman homology search algorithm using an affine gap search with a gap open penalty of 12 and a gap extension penalty of 1.

Another embodiment of the invention is a cDNA molecule which encodes at least 8 contiguous amino acids of a protein encoded by a polynucleotide comprising a nucleotide sequence selected from the group consisting of SEQ ID NOS:1-18.

Even another embodiment of the invention is a cDNA molecule comprising at least 12 contiguous nucleotides of a nucleotide sequence selected from the group consisting of SEQ ID NOS:1-18.

Still another embodiment of the invention is a cDNA molecule which is at least 85% identical to a nucleotide sequence selected from the group consisting of SEQ ID NOS:1-18. Percent identity is determined using a Smith-Waterman homology search algorithm using an affine gap search with a gap open penalty of 12 and a gap extension penalty of 1.

A further embodiment of the invention is an isolated and purified subgenomic polynucleotide comprising a nucleotide segment which hybridizes to a nucleotide sequence selected from the group consisting of SEQ ID NOS:1-18 after washing with 0.2×SSC at 65° C.

Another embodiment of the invention is a construct comprising a promoter and a polynucleotide segment encoding at least 8 contiguous amino acids of a protein encoded by a polynucleotide comprising a nucleotide sequence selected from the group consisting of SEQ ID NOS:1-18. The polynucleotide segment is located downstream from the promoter, wherein transcription of the polynucleotide segment initiates at the promoter.

Yet another embodiment of the invention is a host cell comprising a construct which comprises a promoter and a polynucleotide segment encoding at least 8 contiguous amino acids of a protein encoded by a polynucleotide comprising a nucleotide sequence selected from the group consisting of SEQ ID NOS:1-18.

Even another embodiment of the invention is a recombinant host cell comprising a new transcription initiation unit. The new transcription initiation unit comprises in 5' to 3' order (a) an exogenous regulatory sequence, (b) an exogenous exon and (c) a splice donor site. The new transcription initiation unit is located upstream of a coding sequence of a gene. The coding sequence comprises a nucleotide sequence selected from the group consisting of SEQ ID NOS:1-18. The exogenous regulatory sequence controls transcription of the coding sequence of the gene.

Still another embodiment of the invention is a polynucleotide probe comprising (a) at least 12 contiguous nucleotides selected from the group consisting of SEQ ID NOS:1-18 and (b) a detectable label.

Even another embodiment of the invention is a method for identifying a metastatic tissue or metastatic potential of a tissue. An expression product of a gene comprising a nucleotide sequence selected from the group consisting of SEQ ID NOS:1-4, 6-13, and 15-18 is measured in a tissue sample. A tissue sample which expresses a product of a gene comprising a nucleotide sequence selected from the group consisting of SEQ ID NOS:1, 4, 11, 16, 17, and 18 or which does not express a product of a gene comprising a nucleotide sequence selected from the group consisting of SEQ ID NOS:2, 3, 6, 7, 8, 9, 10, 12, 13, and 15 is identified as metastatic or as having metastatic potential.

Still another embodiment of the invention is a method of screening test compounds for the ability, to suppress the metastatic potential of a tumor. A biological sample is contacted with a test compound. Synthesis of a protein having an amino acid sequence encoded by a polynucleotide comprising a nucleotide sequence selected from the group consisting of SEQ ID NOS:1-4, 6-13, and 15-18 is measured in the biological sample. A test compound which decreases synthesis of a protein encoded by a polynucleotide comprising SEQ ID NOS:1, 4, 11, 16, 17, or 18 or which increases synthesis of a protein encoded by a polynucleotide comprising SEQ ID NOS:2, 3, 6, 7, 8, 9, 10, 12, 13, or 15 is identified as a potential agent for suppressing the metastatic potential of a tumor.

Another embodiment of the invention is a method of predicting propensity for high-grade or low-grade metastatic spread of a colon tumor. An expression product of a gene having a sequence selected from the group consisting of SEQ ID NO:16 and 17 is measured in a colon tumor sample. A colon tumor sample which expresses the product of SEQ ID NO:16 is categorized as having a high propensity to metastasize and a colon tumor sample which expresses the product of SEQ ID NO:17 is categorized as having a low propensity to metastasize.

Still another embodiment of the invention is a set of primers for amplifying at least a portion of a gene having a coding sequence selected from the group consisting of the nucleotide sequences shown in SEQ ID NOS:1-18.

Even another embodiment of the invention is a polynucleotide array comprising at least one single-stranded polynucleotide which comprises at least 12 contiguous nucleotides of a nucleotide sequence selected from the group consisting of SEQ ID NOS:1-18.

A further embodiment of the invention is a method of identifying a metastatic tissue or metastatic potential of a tissue. A tissue sample comprising single-stranded polynucleotide molecules is contacted with a polynucleotide array comprising at least one single-stranded polynucleotide probe. The at least one single-stranded polynucleotide probe comprises at least 12 contiguous nucleotides of a nucleotide sequence selected from the group consisting of SEQ ID NOS: 1-4, 6-13, and 15-18. The tissue sample is suspected of being metastatic or of having metastatic potential. Double-stranded polynucleotides bound to the polynucleotide array are detected. Detection of a double-stranded polynucleotide comprising contiguous nucleotides selected from the group consisting of SEQ ID NOS:1-4, 11, 16, 17, and 18 or lack of detection of a double-stranded polynucleotide comprising contiguous nucleotides selected from the group consisting of SEQ ID NOS:2, 3, 6, 7, 8, 9, 10, 12, 13, and 15 identifies the tissue sample as metastatic or of having metastatic potential.

The invention thus provides the art with a number of genes and proteins, which can be used as markers of metastasis. These are useful for more rationally prescribing the course of therapy for cancer patients, especially those with breast or colon cancer.

BRIEF DESCRIPTION OF THE DRAWINGS

FIG. 1. Arbitrary primer-based differential display and confirmation by RNA blot analysis of different human breast cancer cell line.

FIG. 2. Nucleotide sequence and deduced amino acid sequence of CSP56. FIGS. 2A-1 and 2A-2. Nucleotide sequence and deduced amino acid sequence of CSP56 (SEQ ID NOs: 18 and 19 respectively). FIG. 2A. The 518 amino acid long sequence is shown in single-letter code below the nucleotide sequence of 1855 base pairs. The active site residue (D) and flaming amino acid residues characteristic of aspartyl proteases are underlined. The putative propeptide is boxed. The putative signal peptide at the N-terminus and the transmembrane domain at the C-terminus are underlined. FIG. 2B. Expressed sequence tags (SEQ ID NO: 27) extending the nucleotide sequence of CSP56 to 2606 base pairs in length. FIG. 2C. Schematic representation of CSP56. SS, signal sequence; Pro, propeptide; TM transmembrane domain. The asterisks indicate the active sites.

FIGS. 3A-C. Multiple amino acid sequence alignment of CSP56 (SEQ ID NO: 19) with other members of the pepsin family of aspartyl proteases. Identical amino acid residues are indicated by black boxes. The aspartyl protease active residues (D-SiT-G) are indicated by a bar on top. The cysteine residues characteristic for aspartyl protease in members of the pepsin family are indicted by asterisks. The putative membrane attachment domain is underlined. Gaps are indicated by dots. Cat-E, cathepsin E (SEQ ID NO: 22); Pep-A, pepsinogen E (SEQ ID NO: 23); Pep-C, pepsinogen C (SEQ ID NO: 24); Cat-D, cathepsin D (SEQ ID NO: 25); and Renin (SEQ ID NO: 26).

FIG. 5. CSP56 is up-regulated in patient breast tumor samples.

DETAILED DESCRIPTION OF THE INVENTION

Figure 1A:
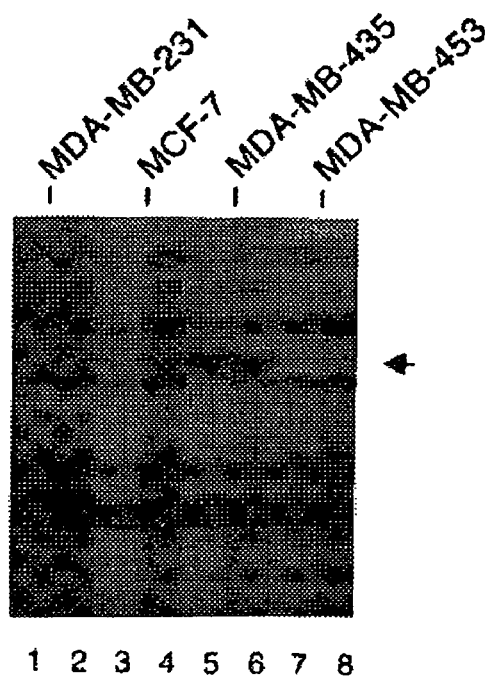
FIG. 1A. Autoradiograph of a differential display gel depicting two bands of approximately 1.2 kb in size in the human breast cancer cell line MDA-MB-435. Differential display reactions were prepared and run in duplicates.

It is a discovery of the present invention that a number of genes are differentially expressed between cancer cells and non-metastatic cancer cells (Table 1). This information can be utilized to make diagnostic reagents specific for the expression products of the differentially displayed genes. It can also be used in diagnostic and prognostic methods which will help clinicians in planning appropriate treatment regimes for cancers, especially of the breast or colon.

Some of the metastatic markers disclosed herein, such as clone 122, are up-regulated in metastatic cells relative to non-metastatic cells. Some of the metastatic markers, such as clones 337 and 280, are down-regulated in metastatic cells relative to non-metastatic cells. Identification of these relationships and markers permits the formulation of reagents and methods as further described below. In addition, homologies to knows proteins have been identified which suggest functions for the disclosed proteins. For example, transcript 280 is homologous to human N-acetylglucosamine-6-sulfatase precursor, transcript 245 is homologous to bifunctional ATP sulfurylase-adenosine 5'-phosphosulfate kinase, and transcript 122 is homologous to human pepsinogen c, an aspartyl protease.

It is another discovery of the present invention that a novel aspartyl-type protease, CSP56, is over-expressed in highly metastatic cancer, particularly in breast and colon cancer, and is associated with the progression of primary tumors to a metastatic state. This information can be utilized to make diagnostic reagents specific for expression products of the CSP56 gene. It can also be used in diagnostic and prognostic methods which will help clinicians to plan appropriate treatment regimes for cancers, especially of the breast and colon.

The amino acid sequence of CSP56 protein is shown in SEQ ID NO:19. Amino acid sequences encoded by novel polynucleotides of the invention can be predicted by running a translation program for each of the three reading frames for a particular polynucleotide sequence. A metastatic marker protein encoded by a polynucleotide comprising a nucleotide sequence as shown in SEQ ID NOS:1-17, the CSP56 protein shown in SEQ ID NO:19, or naturally or non-naturally occurring biologically active protein variants of metastatic marker proteins, including CSP56, can be used in diagnostic and therapeutic methods of the invention. Biologically active metastatic marker protein variants, including CSP56 variants, retain the same biological activities as the proteins encoded by polynucleotides comprising SEQ ID NOS:1-18. Biological activities of metastatic marker proteins include differential expression between tumors and normal tissue, particularly between tumors with high metastatic potential and normal tissue. Biological activity of CSP56 also includes the ability to permit metastases and aspartyl-type protease activity.

Biological activity of a metastatic marker protein variant, including a CSP56 variant, can be readily determined by one of skill in the art. Differential expression of the variant, for example, can be measured in cell lines which vary in metastatic potential, such as the breast cancer cell lines MDA-MB-231 (Brinkley et al., *Cancer Res.* 40, 3118-29, 1980), MDA-MB-435 Brinkley et al., 1980), MCF-7, BT-20, ZR-75-1, MDA-MB-157, MDA-MB-361, MDA-MB-453, Alab and MDA-MB-468, or colon cancer cell lines Km12C and Km12L4A. The MDA-MB-231 cell line was deposited at the ATCC on May 15, 1998 (ATCC CRL-12532). The Km12C cell line was deposited at the ATCC on May 15, 1998 (ATCC CRL-12533). The Km12L4A cell line was deposited at the ATCC on Mar. 19, 1998 (ATCC CRL-12496). The MDA-MB-435 cell line was deposited at the ATCC on Oct. 9, 1998 (ATCC CRL 12583). The MCF-7 cell line was deposited at the ATCC on Oct. 9, 1998 (ATCC CRL-12584).

Expression in a non-cancerous cell line, such as the breast cell line Hs58Bst, can be compared with expression in cancerous cell lines. Alternatively, a breast cancer cell line with high metastatic potential, such as MDA-MB-231 or MDA-MB-435, can be contacted with a polynucleotide encoding a variant and assayed for lowered metastatic potential, for example by monitoring cell division or protein or DNA synthesis, as is known in the art. Aspartyl protease activity of a potential CSP56 variant can also be measured, for example, as taught in Wright et al., *J. Prot. Chem.* 16, 171-81 (1997).

Naturally occurring biologically active metastatic marker protein variants, including variants of CSP56, are found in humans or other species and comprise amino acid sequences which are substantially identical to the amino acid sequences encoded by polynucleotides comprising nucleotide sequences of SEQ ID NOS:1-18. Non-naturally occurring biologically active metastatic marker protein variants can be constructed in the laboratory, using standard recombinant DNA techniques.

Preferably, naturally or non-naturally occurring biologically active metastatic marker protein variants have amino acid sequences which are at least 65%, 75%, 85%, 90%, or 95% identical to the amino acid sequences encoded by polynucleotides comprising nucleotide sequences of SEQ ID NOS:1-18 and have similar differential expression patterns, though these properties may differ in degree. Naturally or non-naturally occurring biologically active CSP56 variants also have aspartyl-type protease activity. More preferably, the variants are at least 98% or 99% identical. Percent sequence identity is determined using computer programs which employ the Smith-Waterman algorithm using an affine gap search with the following parameters, a gap open penalty of 12 and a gap extension penalty of 1. The Smith-Waterman homology search algorithm is taught in Smith and Waterman, *Adv. Appl. Math.* (1981) 2:482-489.

Guidance in determining which amino acid residues may be substituted, inserted, or deleted without abolishing biological or immunological activity may be found using computer programs well known in the art, such as DNASTAR software. Preferably, amino acid changes in biologically active metastatic marker protein variants are conservative amino acid changes, i.e., substitutions of similarly charged or uncharged amino acids. A conservative amino acid change involves substitution of one of a family of amino acids which are related in their side chains. Naturally occurring amino acids are generally divided into four families: acidic (Aspartate, glutamate), basic (lysine, arginine, histidine), non-polar (alanine, valine, leucine, isoleucine, proline, phenylalanine, methionine, tryptophan), and uncharged polar (glycine, asparagine, glutamine, cystine, serine, threonine, tyrosine) amino acids. Phenylalanine, tryptophan, and tyrosine are sometimes classified jointly as aromatic amino acids. It is reasonable to expect that an isolated replacement of a leucine with an isoleucine or valine, an aspartate with a glutamate, a threonine with a serine, or a similar replacement of an amino acid with a structurally related amino acid will not have a major effect on the biological properties of the resulting metastatic marker protein variant. For example, isolated conservative amino acid substitutions are not expected to have a major effect on the aspartyl protease activity of CSP56, especially if the replacement is not at the catalytic domains of the protease.

Metastatic marker protein variants also include allelic variants, species variants, muteins, glycosylated forms, aggregative conjugates with other molecules, and covalent conjugates with unrelated chemical moieties which retain biological activity. Covalent metastatic marker variants can be prepared by linkage of functionalities to groups which are found in the amino acid chain or at the N- or C-terminal residue, as is known in the art. Truncations or deletions of regions which do not affect the expression patterns of metastatic marker proteins or, for example, the aspartyl protease activity of CSP56, are also biologically active variants.

A subset of mutants, called muteins, is a group of proteins in which neutral amino acids, such as serine, are substituted for cysteine residues which do not participate in disulfide bonds. These mutants may be stable over a broader temperature range than naturally occurring proteins. See Mark et al., U.S. Pat. No. 4,959,314.

Metastatic marker polypeptides contain fewer amino acids than full-length metastatic marker proteins. Metastatic marker protein polypeptides can contain at least 8, 10, 12, 15, 25, 50, 75, 100, 150, 200, 250, 300, 350, 400, 450, 500, 550, 600, 650, or 700 contiguous amino acids encoded by a polynucleotide comprising SEQ ID NO: 1; at least 8, 10, 12, 15, 25, 50, 75, 100, or 125 contiguous amino acids encoded by a polynucleotide comprising SEQ ID NOS:2 or 9; at least 8, 10, 12, 15, 25, 50, 75, or 100 contiguous amino acids encoded by a polynucleotide comprising SEQ ID NOS:3, 4, 5, 8, or 10; at least 8; 10, 12, 15, 25, 50, 75, 100, 150, 200, 250, 300, 350, 400, 450, 500, 550, 600, 650, 700, 750, or 800 contiguous amino acids encoded by a polynucleotide comprising SEQ ID NO:6; at least 8, 10, 12, 14, 25, 50, 55, or 60 contiguous amino acids encoded by a polynucleotide comprising SEQ ID NO:7, 8, 10, 12, 15, 25, 50, 75, 100, 150, or 160 contiguous amino acids encoded by a polynucleotide comprising SEQ ID NO: 11; at least 8, 10, 12, 15, 25, 50, 75, 100, 125, or 130 contiguous amino acids encoded by a polynucleotide comprising SEQ ID NO:12 at least 8, 10, 12, 15, 25, 50, 75, or 100 contiguous amino acids encoded by a polynucleotide comprising SEQ ID NO:13; at least 8, 10, 12, 15, 25, 50, 75, 100, 125, 150, 175, 200, 225, 250, 275 or 300 contiguous amino acids encoded by a polynucleotide comprising SEQ ID NO:14; at least 8, 10, 12, 15, 25, 50, 75, 100, or 150 contiguous amino acids encoded by a polynucleotide comprising SEQ ID NO:15; at least 8, 10, 12, 15, 25, 50, 75, 100, 150, 200, 250, 300, 350, 400, 450, 500, 550, 600, 650, 700, 750, 800, 850, 900, 950, 1000, 1050, or 1100 contiguous amino acids encoded by a polynucleotide comprising SEQ ID NO:16; or at least 8, 10, 12, 15, 25, 50, 75, 100, 150, 200, 250, 300, 350, 400, 450, or 500 contiguous amino acids encoded by a polynucleotide comprising SEQ ID NO:17 in the same order as found in the full-length protein or biologically active variant. CSP56 polypeptides can contain at least 8, 10, 11, 12, 13, 14, 15, 16, 17, 20, 21, 23, 25, 28, 29, 30, 31, 32, 33, 35, 40, 50, 60, 75, 100, 111, 112, 120, 150, 175, 200, 225, 250, 275, 300, 325, 350, 375, 400, 425, 450, 475, or 500 or more amino acids of a CSP56 protein or biologically active variant. Preferred CSP56 polypeptides comprise at least amino acids 106-115, 105-116, 104-117, 100-120, 297-306, 296-307, 295-308, 290-320, 8-20, 7-21, 6-22, 1-30, 461-489, 460-490, 459-491, and 407-518 of SEQ ID NO:19. Polypeptide molecules having substantially the same amino acid sequence as the amino acid sequences encoded by polynucleotides comprising nucleotide sequences of SEQ ID NOS:1-38 thereof but possessing minor amino acid substitutions which do not substantially affect the biological properties of a particular metastatic marker polypeptide variant are within the definition of metastatic marker polypeptides.

Metastatic marker proteins or polypeptides can be isolated from, for example, human cells, using biochemical techniques well known to the skilled artisan. A preparation of isolated and purified metastatic marker protein is at least 80% pure; preferably, the preparations are at least 90%, 95%, 98%, or 99% pure. Metastatic marker proteins and polypeptides can also be produced by recombinant DNA methods or by synthetic chemical methods. For production of recombinant metastatic marker proteins or polypeptides, coding sequences selected from SEQ ID NOS:1-18 can be expressed in known prokaryotic or eukaryotic expression systems. Bacterial, yeast, insect, or mammalian expression systems can be used, as is known in the art. Alternatively, synthetic chemical methods, such as solid phase peptide synthesis, can be used to synthesize metastatic marker protein or polypeptides. Biologically active protein or polypeptide variants can be similarly produced.

Fusion proteins comprising contiguous amino acids of metastatic marker proteins of the invention can also be constructed. Fusion proteins are useful for generating antibodies against metastatic marker protein amino acid sequences and for use in various assay systems. For example, CSP56 fusion proteins can be used to identify proteins which interact with CSP56 protein and influence, for example, its aspartyl protease activity, its differential expression, or its ability to permit metastases. Physical methods, such as protein affinity chromatography, or library-based assays for protein-protein interactions, such as the yeast two-hybrid or phage display systems, can also be used for this purpose. Such methods are well known in the art and can also be used as drug screens.

A fusion protein comprises two protein segments fused together by means of a peptide bond. The first protein segment consists of at least 8, 10, 12, 15, 25, 50, 75, 100, 150, 200, 250, 300, 350, 400, 450, 500, 550, 600, 650 or 700 contiguous amino acids encoded by a polynucleotide comprising SEQ ID NO:1; at least 8, 10, 12, 15, 25, 50, 75, 100, or 125 contiguous amino acids encoded by a polynucleotide comprising SEQ ID NOS:2 or 9; at least 8, 10, 12, 15, 25, 50, 75, or 100 contiguous amino acids encoded by a polynucleotide comprising SEQ ID NOS:3, 4, 5, 8, or 10; at least 8, 10, 12, 15, 25, 50, 75, 100, 150, 200, 250, 300, 350, 400, 450, 500, 550, 600, 650, 700, 750, or 800 contiguous amino acids encoded by a polynucleotide comprising SEQ ID NO:6; at least 8, 10, 12, 14, 25, 50, 55, or 60 contiguous amino acids encoded by a polynucleotide comprising SEQ ID NO:7, 8, 10, 12, 15, 25, 50, 75, 100, 150, or 160 contiguous amino acids encoded by a polynucleotide comprising SEQ ID NO:11; at least 8, 10, 12, 15, 25, 50, 75, 100, 125, or 130 contiguous amino acids encoded by a polynucleotide comprising SEQ ID NO:12; at least 8, 10, 12, 15, 25, 50, 75, or 100 contiguous amino acids encoded by a polynucleotide comprising SEQ ID NO:13; at least 8, 10, 12, 15, 25, 50, 75, 100, 125, 150, 175, 200, 225, 250, 275, or 300 contiguous amino acids encoded by a polynucleotide comprising SEQ ID NO:14; at least 8, 10, 12, 15, 25, 50, 75, 100, or 150 contiguous amino acids encoded by a polynucleotide comprising SEQ ID NO:15; at least 8, 10, 12, 15, 25, 50, 75, 100, 150, 200, 250, 300, 350, 400, 450, 500, 550, 600, 650, 700, 750, 800, 850, 900, 950, 1000, 1050, or 1100 contiguous amino acids encoded by a polynucleotide comprising SEQ ID NO:16; or at least 8, 10, 12, 15, 25, 50, 75, 100, 150, 200, 250, 300, 350, 400, 450, or 500 contiguous amino acids encoded by a polynucleotide comprising SEQ ID NO:17, or at least 8, 10, 11, 12, 13, 14, 15, 16, 17, 20, 21, 23, 25, 28, 29, 30, 31, 32, 33, 35, 40, 50, 60, 75, 100, 111, 112, 120, 150, 175, 200, 225, 250, 275, 300, 325, 350, 375, 400, 425, 450, 475, or 500 contiguous amino acids of a CSP56 protein. The amino acids can be selected from the amino acid sequences encoded by polynucleotides comprising SEQ ID NOS:1-18 or from a biologically active variants of those sequences. The first protein segment can also be a full-length metastatic marker protein. The first protein segment can be N-terminal or C-terminal, as is convenient.

The second protein segment can be a full-length protein or a protein fragment or polypeptide. Proteins commonly used in fission protein construction include β-galactosidase, β-glucuronidase, green fluorescent protein (GFP), autofluorescent proteins, including blue fluorescent protein (BFP), glutathione-S-transferase (GST), luciferase, horseradish peroxidase (HRP), and chloramphenicol acetyltransferase (CAT). Additionally, epitope tags are used in fusion protein constructions, including histidine (His) tags, FLAG tags, influenza hemagglutinin (HA) tags, Myc tags, VSV-G tags, and thioredoxin (Trx) tags. Other fusion constructions can include maltose binding protein (UMP), S-tag, Lex A DNA binding domain (DD) fusions, GAL4 DNA binding domain fusions, and herpes simplex virus (HSV) BP16 protein fusions.

These fusions can be made, for example, by covalently linking two protein segments or by standard procedures in the art of molecular biology. Recombinant DNA methods can be used to prepare fusion proteins, for example, by making a DNA construct which comprises coding sequences selected from SEQ ID NOS:1-18 in proper reading frame with nucleotides encoding the second protein segment and expressing the DNA construct in a host cell, as is known in the art. Many kits for constructing fusion proteins are available from companies that supply research labs with tools for experiments, including, for example, Promega Corporation (Madison, Wis.), Stratagene (La Jolla, Calif.), Clontech (Mountain View, Calif.), Santa Cruz Biotechnology (Santa Cruz, Calif.), MBL International Corporation (MIC; Watertown, Mass.), and Quantum Biotechnologies (Montreal, Canada; 1-888-DNA-KITS).

Isolated metastatic marker proteins, polypeptides, biologically active variants, or fusion proteins can be used as immunogens, to obtain a preparation of antibodies which specifically bind to epitopes of metastatic marker protein. The antibodies can be used, inter alia, to detect metastatic marker proteins, such as CSP56, in human tissue, particularly in human tumors, or in fractions thereof. The antibodies can also be used to detect the presence of mutations in metastatic marker protein genes, such as the CSP56 gene, which result in under- or over-expression of a metastatic marker protein or in expression of a metastatic marker protein with altered size or electrophoretic mobility. By binding to CSP56, for example, antibodies can also prevent CSP56 aspartyl-type protease activity or the ability of CSP56 to permit metastases.

Antibodies which specifically bind to epitopes of metastatic marker proteins, polypeptides, fusion proteins, or biologically active variants can be used in immunochemical assays, including but not limited to Western Blots, ELISAs, radioimmunoassays, immunohistochemical assays, immunoprecipitations, or other immunochemical assays known in the art. Typically, antibodies of the invention provide a detection signal at least 5-, 10-, or 20-fold higher than a detection signal provided with other proteins when used in such immunochemical assays. Preferably, antibodies which specifically bind to epitopes of a particular metastatic marker protein do not detect other proteins in immunochemical assays and can immunoprecipitate that metastatic marker protein or polypeptide fragments of the metastatic marker protein from solution.

Metastatic marker protein-specific antibodies specifically bind to epitopes present in a metastatic marker protein having an amino acid sequence encoded by a polynucleotide comprising a nucleotide sequence of SEQ ID NOS:1-18 or to biologically active variants of those amino acid sequences. Typically, at least 6, 8, 10, or 12 contiguous amino acids are required to form an epitope. However, epitopes which involve non-contiguous amino acids may require more, e.g. at least 15, 25, or 50 amino acids. Preferably, metastatic marker protein epitopes are not present in other human proteins.

Epitopes of a metastatic marker protein which are particularly antigenic can be selected, for example, by routine screening of polypeptide fragments of the metastatic marker protein for antigenicity or by applying a theoretical method for selecting antigenic regions of a protein to the amino acid sequence of the metastatic marker protein. Such methods are taught, for example, in Hopp and Wood, *Proc. Natl. Acad. Sci. U.S.A.* 78, 3824-28 (1981), Hopp and Wood, *Mol. Immunol.* 20, 483-89 (1983), and Sutcliffe et al., *Science* 219, 660-66 (1983). By reference to FIG. 3, antigenic regions of CSP56 which could also bind to antibodies which crossreact with other aspartyl proteases can be avoided.

Any type of antibody known in the art can be generated to bind specifically to metastatic marker protein epitopes. For example, preparations of polyclonal and monoclonal antibodies can be made using standard methods which are well known in the art. Similarly, single-chain antibodies can also be prepared. Single-chain antibodies which specifically bind to metastatic marker protein epitopes can be isolated, for example, from single-chain immunoglobulin display libraries, as is known in the art. The library is "panned" against a metastatic marker protein amino acid sequence, and a number of single chain antibodies which bind with high-affinity to different epitopes of the metastatic marker protein can be isolated. Hayashi et al., 1995, *Gene* 160:129-30. Single-chain antibodies can also be constructed using a DNA amplification method, such as the polymerase chain reaction (PCR), using hybridoma cDNA as a template. Thirion et al., 1996, *Eur. J. Cancer Prev.* 5:507-11.

Single-chain antibodies can be mono- or bispecific, and can be bivalent or tetravalent. Construction of tetravalent, bispecific single-chain antibodies is taught, for example, in Coloma and Morrison, 1997, *Nat. Biotechnol.* 15:159-63. Construction of bivalent, bispecific single-chain antibodies is taught inter alia in Mallender and Voss, 1994, *J. Biol. Chem.* 269:199-206.

A nucleotide sequence encoding a single-chain antibody can be constructed using manual or automated nucleotide synthesis, cloned into an expression construct using standard recombinant DNA methods, and introduced into a cell to express the coding sequence, as described below. Alternatively, single-chain antibodies can be produced directly using, for example, filamentous phage technology. Verhaar et al., 1995, *Int. J. Cancer* 61:497-501; Nicholls et al., 1993, *J. Immunol. Meth.* 165:81-91.

Monoclonal and other antibodies can also be "humanized" in order to prevent a patient from mounting an immune response against the antibody when it is used therapeutically. Such antibodies may be sufficiently similar in sequence to human antibodies to be used directly in therapy or may require alteration of a few key residues. Sequence differences between, for example, rodent antibodies and human sequences can be minimized by replacing residues which differ from those in the human sequences, for example, by site directed mutagenesis of individual residues, or by grating of entire complementarity determining regions. Alternatively, one can produce humanized antibodies using recombinant methods, as described in GB2188638B. Antibodies which specifically bind to epitopes of a metastatic marker protein can contain antigen binding sites which are either partially or fully humanized, as disclosed in U.S. Pat. No. 5,565,332.

Other types of antibodies can be constructed and used therapeutically in methods of the invention. For example; chimeric antibodies can be constructed as disclosed, for example, in WO 93/03151. Binding proteins which are derived from immunoglobulins and which are multivalent and multispecific, such as the "diabodies" described in WO 94/13804, can also be prepared.

Antibodies of the invention can be purified by methods well known in the art. For example, antibodies can be affinity purified by passing the antibodies over a column to which a metastatic marker protein, polypeptide, variant, or fusion protein is bound. The bound antibodies can then be eluted from the column, using a buffer with a high salt concentration.

The invention also provides subgenomic polynucleotides which encode metastatic marker proteins, polypeptides, variants, or fusion proteins. Subgenomic polynucleotides contain less than a whole chromosome. Preferably, the subgenomic polynucleotides are intron-free. An isolated metastatic marker protein subgenomic polynucleotide comprises at least 8, 9, 10, 11, 12, 13, 14, 15, 16, 17, 18, 19, 20, 25, 30, 40, 50, 75, 100, 125, 150, 175, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, 2000, 2050, 2100, 2150, or 2200 contiguous nucleotides of SEQ ID NO:1 at least 8, 9, 10, 11, 12, 13, 14, 15, 16, 17, 18, 19, 20, 25, 30, 40, 50, 75, 100, 125, 150, 175, 200, 250, 300, 350, or 400 contiguous nucleotides of SEQ ID NOS:2 or 9; at let 8, 9, 10, 11, 12, 13, 14, 15, 16, 17, 18, 19, 20, 25, 30, 40, 50, 75, 100, 125, 150, 175, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, 2000, 2250, or 2500 contiguous nucleotides of SEQ ID NO:6; at least 8, 9, 10, 11, 12, 13, 14, 15, 16, 17, 18, 19, 20, 25, 30, 40, 50, 75, 100, 125, 150, or 175 contiguous nucleotides of SEQ ID NO:7, at least 8, 9, 10, 11, 12, 13, 14, 15, 16, 17, 18, 19, 20, 25, 30, 40, 50, 75, 100, 125, 150, 175, 200, 250, 300, or 350 contiguous nucleotides of SEQ ID NO:8; at least 8, 9, 10, 11, 12, 13, 14, 15, 16, 17, 18, 19, 20, 25, 30, 40, 50, 75, 100, 125, 150, 175, 200, 250, 300, or 350 contiguous nucleotides of SEQ ID NO:12; at least 8, 9, 10, 11, 12, 13, 14, 15, 16, 17, 18, 19, 20, 25, 30, 40, 50, 75, 100, 125, 150, 175, 200, 250, or 300 contiguous nucleotides of SEQ ID NOS:3, 4, 5, or 10; at least 8, 9, 10, 11, 12, 13, 14, 15, 16, 17, 18, 19, 20, 25, 30, 40, 50, 75, 100, 125, 150, 175, 200, 250, 300, 350, 400, 450, or 500 contiguous nucleotides of SEQ ID NO:11; at least 8, 9, 10, 11, 12, 13, 14, 15, 16, 17, 18, 19, 20, 25, 30, 40, 50, 75, 100, 125, 150, 175, 200, 250, or 300 contiguous nucleotides of SEQ ID NO:13; at least 8, 9, 10, 11, 12, 13, 14, 15, 16, 17, 18, 19, 20, 25, 30, 40, 50, 75, 100, 125, 150, 175, 200, 250, 306, 350, 400, 450, 560, 550, 600, 650, 700, 750, 800, 850, 900, or 950 contiguous nucleotides of SEQ ID NO:14; at least 8, 9, 10, 11, 12, 13, 14, 15, 16, 17, 18, 19, 20, 25, 30, 40, 50, 75, 100, 125, 150, 175, 200, 250, 300, 350, 400, or 450 contiguous nucleotides of SEQ ID NO:15; at least 8, 9, 10, 11, 12, 13, 14, 15, 16, 17, 18, 19, 20, 25, 30, 40, 50, 75, 100, 125, 150, 175, 200, 250, 300, 350, 400, 450, 500, 550, 600, 650, 700, 750, 800, 850, 900, 950, 3000, 1050, 1100, 1150, 1200, 1250, 1300, 1350, 1400, 1450, 1500, 1550, 1600, 1650, 1700, 1750, 1800, 1850, 1900, 1950, 2000, 2250, 2500, 2750, 3000, 3250, or 3500 contiguous nucleotides of SEQ ID NO:16; or at least 8, 9, 10, 11, 12, 13, 14, 15, 16, 17, 18, 19, 20, 25, 30, 40, 50, 75, 100, 125, 150, 175, 200, 250, 300, 350, 400, 450, 500, 550, 600, 650, 700, 750, 800, 850, 900, 950, 1000, 1050, 1100, 1150, 1200, 1250, 1300, 1350, 1400, 1450, or 1500 contiguous nucleotides of SEQ ID NO:17 or can comprise one of SEQ ID NOS:1-17.

A CSP56 polynucleotide can comprise a contiguous sequence of at least 10, 11, 12, 15, 20, 24, 25, 30, 32, 33, 35, 36, 40, 42, 45, 48, 50, 51, 54, 60, 63, 69, 70, 74, 75, 80, 84, 87, 90, 93, 96, 99, 100, 105, 114, 120, 125, 150, 225, 300, 333, 336, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, or 1850 nucleotides selected from SEQ ID NO:18 or can comprise SEQ ID NO:18. An isolated CSP56 polynucleotide encodes at least 8, 10, 12, 14, 15, 17, 18, 20, 25, 29, 30, 31, 32, 40, 50, 75, 100 or 111 contiguous amino acids of SEQ ID NO:19 and can encode the entire amino acid sequence shown in SEQ ID NO:19. Preferred CSP56 polynucleotides encode at least amino acids 1-30, 8-20, 7-21, 6-22, 106-115, 105-116, 104-117, 100-120, 297-306, 296-307, 295-308, 290-320, 461-489, 460-490, 459-491, and 407-518 of SEQ ID NO:19.

The complements of the nucleotide sequences shown in SEQ ID NOS:1-18 are contiguous nucleotide sequences which form Watson-Crick base pairs with a contiguous nucleotide sequence as shown in SEQ ID NOS:1-18. The complements of SEQ ID NOS:1-18 are also polynucleotides of the invention. Complements of coding sequences can be used to provide antisense oligonucleotides and probes. Antisense oligonucleotides and probes of the invention can consist of at least 11, 12, 15, 20, 25, 30, 50, or 100 contiguous nucleotides. A complement of an entire coding sequence can also be used. Double-stranded polynucleotides which comprise all or a portion of the nucleotide sequences shown in SEQ ID NOS: 1-18, as well as polynucleotides which encode metastatic marker protein-specific antibodies or ribozymes, are also polynucleotides of the invention.

Degenerate nucleotide sequences encoding amino acid sequences of metastatic marker proteins and or variants, as well as homologous nucleotide sequences which are at least 65%, 75%, 85%, 90%, 95%, 98%, or 99% identical to the nucleotide sequences shown in SEQ ID NOS:1-18, are also polynucleotides of the invention. Percent sequence identity can be determined using computer programs which employ the Smith-Waterman algorithm, for example as implemented in the MPSRCH program (Oxford Molecular), using an affine gap search with the following parameters: a gap open penalty of 12 and a gap extension penalty of 1.

Typically, homologous polynucleotide sequences of the invention can be confirmed by hybridization under stringent conditions, as is known in the art. For example, using the following wash conditions—2×SSC, 0.1% SDS, room temperature twice, 30 minutes each; then 2×SSC, 0.1% SDS, 50° C. once for 30 minutes; then 2×SSC, room temperature twice, 10 minutes each—homologous sequences can be identified that contain at most about 25-30% basepair mismatches. More preferably, homologous nucleic acid strands contain 15-25% basepair mismatches, even more preferably 5-15%, 2-10%, or 1-5% basepair mismatches. Degrees of homology of polynucleotides of the invention can be selected by varying the stringency of the wash conditions for identification of clones from gene libraries (or other sources of genetic material), as is well known in the art and described, for example, in manuals such as Sambrook et al., MOLECULAR CLONING: A LABORATORY MANUAL, 2d ed. (1989).

Species homologs of subgenomic polynucleotides of the invention can also be identified by making suitable probes or primers and screening cDNA expression libraries or genomic libraries from other species, such as mice, monkeys, yeast, or bacteria. Complete polynucleotide sequences can be obtained by chromosome walking, screening of libraries for overlapping clones, 5' RACE, or other techniques well known in the art. It is well known that the $T_m$ of a double-stranded DNA decreases by 1-1.5° C. with every 1% decrease in homology (Bonner et al., *J. Mol. Biol.* 81, 123 (1973). Homologous human polynucleotides or polynucleotides of other species can therefore be identified, for example, by hybridizing a putative homologous polynucleotide with a polynucleotide having a nucleotide sequence of SEQ ID NOS:1-18, comparing the melting temperature of the test hybrid with the melting temperature of a hybrid comprising a polynucleotide having a nucleotide sequence of SEQ ID NOS:1-18 and a polynucleotide which is perfectly complimentary to the nucleotide sequence, and calculating the number of basepair mismatches within the test hybrid.

Nucleotide sequences which hybridize to the nucleotide sequences shown in SEQ ID NOS:1-18 following stringent hybridization and/or wash conditions are also subgenomic polynucleotides of the invention. Stringent wash conditions are well known and understood in the art and are disclosed, for example, in Sambrook et al., 1989, at pages 9.50-9.51.

Typically, for stringent hybridization conditions a combination of temperature and salt concentration should be chosen that is approximately 12-20° C. below the calculated $T_m$ of the hybrid under study. The $T_m$ of a hybrid between a polynucleotide sequence shown in SEQ ID NOS:1-18 and a polynucleotide sequence which is 65%, 75%, 85%, 90%, 95%, 96%, 97%, 98%, or 99% identical to that sequence can be calculated, for example, using the equation of Bolton and McCarthy, *Proc. Natl. Acad. Sci. U.S.A.* 48, 1390 (1962):

$$T_m = 81.5° C. - 16.6(\log_{10}[Na^+]) + 0.41(\% G+C) - 0.63(\% \text{formamide}) - 600/l,$$

where l=the length of the hybrid in basepairs.

Stringent wash conditions include, for example, 4×SSC at 65° C., or 50% formamide, 4×SSC at 42° C., or 0.5×SSC, 0.1% SDS at 65° C. Highly stringent wash conditions include, for example, 0.2×SSC at 65° C.

Subgenomic polynucleotides can be purified free from other nucleotide sequences using standard nucleic acid purification techniques. For example, restriction enzymes and probes can be used to isolate polynucleotides which comprise nucleotide sequences encoding metastatic marker proteins. Alternatively, PCR can be used to synthesize and amplify such polynucleotides. At least 90% of a preparation of isolated and purified polynucleotides comprises metastatic marker protein encoding polynucleotides.

Complementary DNA (cDNA) molecules which encode metastatic marker proteins are also subgenomic polynucleotides of the invention. cDNA molecules can be made with standard molecular biology techniques, using mRNA as a template. cDNA molecules can thereafter be replicated using molecular biology techniques known in the art and disclosed in manuals such as Sambrook et al., 1989. An amplification technique, such as the polymerase chain reaction (PCR), can be used to obtain additional copies of subgenomic polynucleotides of the invention, using either human genomic DNA or cDNA as a template.

Alternatively, synthetic chemistry techniques can be used to synthesize subgenomic polynucleotide molecules of the invention. The degeneracy of the genetic code allows alternate nucleotide sequences to be synthesized which will encode a metastatic marker protein having an amino acid sequence encoded by a polynucleotide comprising a nucleotide sequence selected from SEQ ID NOS:1-17, a CSP56 amino acid sequence as shown in SEQ ID NO:19, or a biologically active variant of those sequences. All such nucleotide sequences are within the scope of the present invention.

The invention also provides polynucleotide probes which can be used to detect metastatic marker polypeptide sequences, for example, in hybridization protocols such as Northern or Southern blotting or in situ hybridizations. Polynucleotide probes of the invention comprise at least 12, 13, 14, 15, 16, 17, 18, 19, 20, 30, or 40 or more contiguous nucleotides selected from SEQ ID NOS:1-18. Polynucleotide probes of the invention can comprise a detectable label, such as a radioisotopic, fluorescent, enzymatic, or chemiluminescent label.

Isolated polynucleotides can be used, for example, as primers to obtain additional copies of the polynucleotides or as probes for detecting mRNA. Poly nucleotides can also be used to express metastic marker protein mRNA, protein, polypeptides, biologically active variants, single-chain antibodies, ribozymes, or fusion proteins.

Any of the polynucleotides described above can be present in a construct, such as a DNA or RNA construct. The construct can be a vector and can be used to transfer the polynucleotide into a cell, for example, for propagation of the polynucleotide. Constructs, can be linear or circular molecules. They can be on autonomously replicating molecules or on molecules without replication sequences, and they can be regulated by their own or by other regulatory sequences, as is known in the art.

A construct can also be an expression construct. An expression construct comprises a promoter which is functional in a selected host cell. For example, the skilled artisan can readily select an appropriate promoter from the large number of cell type-specific promoters known and used in the art. The expression construct can also contain a transcription terminator which is functional in the host cell. The expression construct comprises a polynucleotide segment which encodes, for example, all or a portion of a metastatic marker protein, polypeptide, biologically active variant, antibody, ribozyme, or fusion protein. The polynucleotide segment is located downstream from the promoter. Transcription of the polynucleotide segment initiates at the promoter. The expression construct can be linear or circular and can contain sequences, if desired, for autonomous replication.

Subgenomic polynucleotides can be propagated in vectors and cell lines using techniques well known in the art. Expression systems in bacteria include those described in Chang et al., *Nature* (1978) 275: 615, Goeddel et al., *Nature* (1979) 281: 544, Goeddel et al., *Nucleic Acids Res.* (1980) 8: 4057, EP 36,776, U.S. Pat. No. 4,551,433, deBoer et al., *Proc. Natl. Acad. Sci. USA* (1983) 80: 21-25, and Siebenlist et al., *Cell* (1980) 20: 269.

Expression systems in yeast include those described in Hinnen et al., *Proc. Natl. Acad. Sci. USA* (1978) 75: 1929; Ito et al., *J. Bacteriol.* (1983) 153: 163; Kurtz et al., *Mol. Cell. Biol.* (1986) 6: 142; Kunze et al., *J. Basic Microbiol.* (1985) 25: 141; Gleeson et al., *J. Gen. Microbiol.* (1986) 132: 3459, Roggenkamp et al., *Mol. Gen. Genet.* (1986) 202:302) Das et al., *J. Bacteriol.* (1984) 158: 1165; De Louvencourt et al. *J. Bacteriol.* (1983) 154: 737, Van den Berg et al., *Bio/Technology* (1990) 8: 135; Kunze et al., *J. Basic Microbiol.* (1985) 25: 141; Cregg et al., *Mol. Cell. Biol.* (1985) 5: 3376, U.S. Pat. No. 4,837,148, U.S. Pat. No. 4,929,555; Beach and Nurse, *Nature* (1981) 300: 706; Davidow et al., *Curr. Genet.* (1985) 10: 380, Gaillardin et al. *Curr. Genet.* (1985) 10: 49, Ballance et al., *Biochem. Biophys. Res. Commun.* (1983) 112: 284-289; Tilburn et al., *Gene* (1983) 26: 205-221, Yelton et al., *Proc.*

*Natl. Acad. Sci. USA* (1984) 81: 1470-1474, Kelly and Hynes, *EMBO J.* (1985) 4: 475479; EP 244,234, and WO 91/00357.

Expression of subgenomic polynucleotides in insects can be accomplished as described in U.S. Pat. No. 4,745,051, Friesen et al. (1986) "The Regulation of Baculovirus Gene Expression" in: THE MOLECULAR BIOLOGY OF BACULOVIRUSES (W. Doerfler, ed.), EP 127,839, EP 155,476, and Vlak et al., *J. Gen. Virol.* (1988) 69: 765-776, Miller et al., *Ann. Rev. Microbiol.* (1988) 42: 177, Carbonell et al., *Gene* (1988) 73: 409, Maeda et al., *Nature* (1985) 315: 592-594, Lebacq-Verheyden et al., *Mol. Cell. Biol.* (1988) 8: 3129; Smith et al., *Proc. Natl. Acad. Sci. USA* (1985) 82: 8404, Miyajima et al., *Gene* (1987) 58: 273; and Martin et al., *DNA* (1988) 7:99. Numerous baculoviral strains and variants and corresponding permissive insect host cells from hosts are described in Luckow et al., *Bio/Technology* (1988) 6: 47-55, Miller et al., in GENETIC ENGINEERING (Setlow, J. K. et al. eds.), Vol. 8 (Plenum Publishing, 1986), pp. 277-279, and Maeda et al., *Nature*, (1985) 315: 592-594.

Mammalian expression of subgenomic polynucleotides can be accomplished as described in Dijkema et al., *EMBO J.* (1985) 4: 761, Gorman et al., *Proc. Natl. Acad. Sci. USA* (1982b) 79: 6777, Boshart et al., *Cell* (1985) 41: 521 and U.S. Pat. No. 4,399,216. Other features of mammalian expression can be facilitated as described in Ham and Wallace, *Meth. Enz.* (1979) 58: 44, Barnes and Sato, *Anal. Biochem.* (1980) 102: 255, U.S. Pat. No. 4,767,704, U.S. Pat. No. 4,657,866, U.S. Pat. No. 4,927,762, U.S. Pat. No. 4,560,655, WO 90/103430, WO 87/00195, and U.S. RE 30,985.

Subgenomic polynucleotides can be on linear or circular molecules. They can be on autonomously replicating molecules or on molecules without replication sequences. They can be regulated by their own or by other regulatory sequences, as is known in the art. Subgenomic polynucleotides can be introduced into suitable host cells using a variety of techniques which are available in the art, such as transferrin-polycation-mediated DNA transfer, transfection with naked or encapsulated nucleic acids, liposome-mediated DNA transfer, intracellular transportation of DNA-coated latex beads, protoplast fusion, viral infection, electroporation, and calcium phosphate-mediated transfection.

Polynucleotides of the invention can also be used in gene delivery vehicles, for the purpose of delivering an mRNA or oligonucleotide (either with the sequence of a native mRNA or its complement), full-length protein, fusion protein, polypeptide, or ribozyme, or single-chain antibody, into a cell, preferably a eukaryotic cell. According to the present invention, a gene delivery vehicle can be, for example, naked plasmid DNA, a viral expression vector comprising a polynucleotide of the invention, or a polynucleotide of the invention in conjunction with a liposome or a condensing agent.

In one embodiment of the invention, the gene delivery vehicle comprises a promoter and one of the polynucleotides disclosed herein. Preferred promoters are tissue-specific promoters and promoters which are activated by cellular proliferation, such as the thymidine kinase and thymidylate synthase promoters. Other preferred promoters include promoters which are activatable by infection with a virus, such as the α- and β-interferon promoters, and promoters which are activatable by a hormone, such as estrogen. Other promoters which can be used include the Moloney virus LTR, the CMV promoter, and the mouse albumin promoter.

A gene delivery vehicle can comprise viral sequences such as a viral origin of replication or packaging signal. These viral sequences can be selected from viruses such as astrovirus, coronavirus, orthomyxovirus, papovavirus, paramyxovirus, parvovirus, picornavirus, poxvirus, retrovirus, togavirus or adenovirus. In a preferred embodiment, the gene delivery vehicle is a recombinant retroviral vector. Recombinant retroviruses and various uses thereof have been described in numerous references including, for example, Mann et al., *Cell* 33:153, 1983, Cane and Mulligan, *Proc. Nat'l. Acad. Sci. USA* 81:6349, 1984, Miller et al., *Human Gene Therapy* 1:5-14, 1990, U.S. Pat. Nos. 4,405,712, 4,861,719, and 4,980,289, and PCT Application Nos. WO 89/02,468, WO 89/05,349, and WO 90/02,806. Numerous retroviral gene delivery vehicles can be utilized in the present invention, including for example those described in EP 0,415,731; WO 90/07936; WO 94/03622; WO 93/25698; WO 93/25234; U.S. Pat. No. 5,219,740; WO 9311230; WO 9310218; Vile and Hart, *Cancer Res.* 53:3860-3864, 1993; Vile and Hart, *Cancer Res.* 53:962-967, 1993; Ram et al., *Cancer Res.* 53:83-88, 1993; Takamiya et al., *J. Neurosci. Res.* 33:493-503, 1992; Baba et al., *J. Neurosurg.* 79:729-735, 1993 (U.S. Pat. No. 4,777,127, GB 2,200,651, EP 0,345,242 and WO91/02805).

Particularly preferred retroviruses are derived from retroviruses which include avian leukosis virus (ATCC Nos. VR-535 and VR-247), bovine leukemia virus (VR-1315), murine leukemia virus (MLV), mink-cell focus-inducing virus (Koch et al., *J. Vir.* 49:828, 1984; and Oliff et al., *J. Vir.* 48:542, 1983), murine sarcoma virus (ATCC Nos. VR-844; 45010 and 45016), reticuloendotheliosis virus (ATCC Nos VR-994, VR-770 and 45011), Rous sarcoma virus, Mason-Pfizer monkey virus; baboon endogenous virus, endogenous feline retrovirus (e.g., RD114), and mouse or rat gL30 sequences used as a retroviral vector.

Particularly preferred strains of MLV from which recombinant retroviruses can be generated include 4070A and 1504A (Hartley and Rowe, *J. Vir.* 19:19, 1976), Abelson (ATCC No. VR-999), Friend (ATCC No. VR-245). Graffi (Ru et al., *J. Vir.* 67:4722, 1993; and Yantchev *Neoplasma* 26:397, 1979), Gross (ATCC No. VR-590), Kirsten (Albino et al., *J. Exp. Med.* 164:1710, 1986), Harvey sarcoma virus (Manly et al. *J. Vir.* 62:3540, 1988; and Albino et al., *J. Exp. Med.* 164:1710, 1986) and Rauscher (ATCC No. VR-998), and Moloney MLV (ATCC No. VR-190).

A particularly preferred non-mouse retrovirus is Rous sarcoma virus. Preferred Rous sarcoma viruses include Bratislava (Manly et al., *J. Vir.* 62:3540, 1988; and Albino et al., *J. Exp. Med.* 164:1710, 1986), Bryan high titer (e.g., ATCC Nos. VR-334, VR-657, VR-726, VR-659, and VR-728), Bryan standard (ATCC No. VR-140), Carr-Zilber (Adgighitov et al., *Neoplasma* 27:159, 1980), Engelbreth-Holm (Laurent et al., *Biochem Biophys Acta* 908:241, 1987), Harris, Prague (e.g., ATCC Nos. VR-772, and 45033), and Schmidt-Ruppin (e.g. ATCC Nos. VR-724, VR-725, VR-354) viruses.

Any of the above retroviruses can be readily utilized in order to assemble or construct retroviral gene delivery vehicles given the disclosure provided herein and standard recombinant techniques (e.g., Sambrook et al., 1989, and Kunkle, *Proc. Natl. Acad. Sci. U.S.A.* 82:488, 1985) known in the art. Portions of retroviral expression vectors can be derived from different retroviruses. For example, retrovector LTRs can be derived from a murine sarcoma virus, a tRNA binding site from a Rous sarcoma virus, a packaging signal from a murine leukemia virus, and an origin of second strand synthesis from an avian leukosis virus. These recombinant retroviral vectors can be used to generate transduction competent retroviral vector particles by introducing them into appropriate packaging cell lines (see Ser. No. 07/800,921, filed Nov. 29, 1991). Recombinant retroviruses can be produced which direct the site-specific integration of the recombinant retroviral genome into specific regions of the host cell DNA. Such site-specific integration can be mediated by a chimeric integrase incorporated into the retroviral particle (see Ser. No. 08/445,466 filed May 22, 1995). It is preferable that the recombinant viral gene delivery vehicle is a replication-defective recombinant virus.

Packaging cell lines suitable for use with the above-described retroviral gene delivery vehicles can be readily prepared (see Ser. No. 08/240,030, filed May 9, 1994; see also WO 92/05266) and used to create producer cell lines (also termed vector cell lines or "VCLs") for production of recombinant viral particles. In particularly preferred embodiments of the present invention, packaging cell lines are made from human (e.g., HT1080 cells) or mink parent cell lines, thereby allowing production of recombinant retroviral gene delivery vehicles which are capable of surviving inactivation in human serum. The construction of recombinant retroviral gene delivery vehicles is described in detail in WO 91/02805. These recombinant retroviral gene delivery vehicles can be used to generate transduction competent retroviral particles by introducing them into appropriate packaging cell lines (see Ser. No. 07/800,921). Similarly, adenovirus gene delivery vehicles can also be readily prepared and utilized given the disclosure provided herein (see also Berkner, *Biotechniques* 6:616-627, 1988, and Rosenfeld et al., *Science* 252:431-434, 1991, WO 93/07283, WO 93/06223, and WO 93/07282).

A gene delivery vehicle can also be a recombinant adenoviral gene delivery vehicle. Such vehicles can be readily prepared and utilized given the disclosure provided herein (see Berkner, *Biotechniques* 6:616, 1988, and Rosenfeld et al., *Science* 252:431, 1991, WO 93/07283, WO 93/06223, and WO 93/07282). Adeno-associated viral gene delivery vehicles can also be constructed and used to deliver proteins or polynucleotides of the invention to cells in vitro or in vivo. The use of adeno-associated viral gene delivery vehicles in vitro is described in Chatterjee et al., *Science* 258: 1485-1488 (1992), Walsh et al., *Proc. Nat'l. Acad. Sci.* 89: 7257-7261 (1992), Walsh et al., *J. Clin. Invest.* 94: 1440-1448 (1994), Flotte et al., *J. Biol. Chem.* 268: 3781-3790 (1993), Ponnazhagan et al., *J. Exp. Med.* 179: 733-738 (1994), Miller et al., *Proc. Nat'l Acad. Sci.* 91: 10183-10187 (1994), Einerhand et al., *Gene Ther.* 2: 336-343 (1995), Luo et al., *Exp. Hematol.* 23:1261-1267 (1995), and Zhou et al., *Gene Therapy* 3: 223-229 (1996). In viva use of these vehicles is described in Flotte et al., *Proc. Nat'l Acad. Sci.* 90: 10613-10617 (1993), and Kaplitt et al., *Nature Genet.* 8:148-153 (1994).

In another embodiment of the invention, a gene delivery vehicle is derived from a togavirus. Preferred togaviruses include alphaviruses, in particular those described in U.S. Ser. No. 08/405,627, filed Mar. 15, 1995, WO 95/07994. Alpha viruses, including Sindbis and ELVS viruses can be gene delivery vehicles for polynucleotides of the invention. Alpha viruses are described in WO 94/21792. WO 92/10578 and WO 95/07994. Several different alphavirus gene delivery vehicle systems can be constructed and used to deliver polynucleotides to a cell according to the present invention. Representative examples of such systems include those described in U.S. Pat. Nos. 5,091,309 and 5,217,879. Particularly preferred alphavirus gene delivery vehicles for use in the present invention include those which are described in WO 95/07994, and U.S. Ser. No. 08/405,627.

Preferably, the recombinant viral vehicle is a recombinant alphavirus viral vehicle based on a Sindbis virus. Sindbis constructs, as well as numerous similar constructs, can be readily prepared essentially as described in U.S. Ser. No. 08/198,450. Sindbis viral gene delivery vehicles typically comprise a 5' sequence capable of initiating Sindbis virus transcription, a nucleotide sequence encoding Sindbis nonstructural proteins, a viral junction region inactivated so as to prevent fragment transcription, and a Sindbis RNA polymerase recognition sequence. Optionally, the viral junction region can be modified so that polynucleotide transcription is reduced, increased, or maintained. As will be appreciated by those in the art, corresponding regions from other alphaviruses can be used in place of those described above.

The viral junction region of an alphavirus-derived gene delivery vehicle can comprise a first viral junction region which has been inactivated in order to prevent transcription of the polynucleotide and a second viral junction region which has been modified such that polynucleotide transcription is reduced. An alphavirus-derived vehicle can also include a 5' promoter capable of initiating synthesis of viral RNA from cDNA and a 3' sequence which controls transcription termination.

Other recombinant togaviral gene delivery vehicles which can be utilized in the present invention include those derived from Semliki Forest virus (ATCC VR-67; ATCC VR-1247), Middleberg virus (ATCC VR-370), Ross River virus (ATCC VR-373; ATCC VR-1246), Venezuelan equine encephalitis virus (ATCC VR-923; ATCC VR-1250; ATCC VR-1249; ATCC VR-532), and those described in U.S. Pat. Nos. 5,091, 309 and 5,217,879 and in WO 92/10578. The Sindbis vehicles described above, as well as numerous similar constructs, can be readily prepared essentially as described in U.S. Ser. No. 08/198,450.

Other viral gene delivery vehicles suitable for use in the present invention include, for example, those derived from poliovirus (Evans et al., *Nature* 339:385, 1989, and Sabin et al., *J. Biol. Standardization* 1:115, 1973) (ATCC VR-58); rhinovirus (Arnold et al., *J. Cell. Biochem.* L401, 1990) (ATCC VR-1110); pox viruses, such as canary pox virus or vaccinia virus (Fisher-Hoch et al., *PROC. NATL. ACAD. SCI. U.S.A.*, 86:317, 1989; Flexner et al., *Ann. N.Y. Acad. Sci.* 569:86, 1989; Flexner et al., *Vaccine* 8:17, 1990; U.S. Pat. No. 4,603,112 and U.S. Pat. No. 4,769,330; WO 89/01973) (ATCC VR-111; ATCC VR-2010); SV40 (Mulligan et al., *Nature* 277:108, 1979) (ATCC VR-305), (Madzak et al., *J. Gen. Vir.* 73:1533, 1992); influenza virus (Luytjes et al., *Cell* 59:1107, 1989; McMicheal et al., *The New England Journal of Medicine* 309:13, 1983; and Yap et al., *Nature* 273:238, 1978) (ATCC VR-797); parvovirus such as adeno-associated virus (Samulski et al., *J. Vir.* 63:3822, 1989, and Mendelson et al., *Virology* 166:154, 1988) (ATCC VR-645); herpes simplex virus it et al. *Adv. Exp. Med. Biol.* 215:219, 1989) (ATCC VR-977; ATCC VR-260); *Nature* 277: 108, 1979); human immunodeficiency virus (EPO 386,882, Buchschacher et al. *J. Vir.* 66:2731, 1992); measles virus (EPO 440,219) (ATCC VR-24); A (ATCC VR-67; ATCC VR-1247), Aura (ATCC VR-368). Bebaru virus (ATCC VR-600; ATCC VR-1240), Cabassou (ATCC VR-922), Chikungunya virus (ATCC VR-64; ATCC VR-1241), Fort Morgan (ATCC VR-924), Getah virus (ATCC VR-369; ATCC VR-1243), Kyzylagach (ATCC VR-927), Mayaro (ATCC VR-66), Mucambo virus (ATCC VR-580; ATCC VR-1244), Ndumu (ATCC VR-371), Pixuna virus (ATCC VR-372; ATCC VR-1-245), Tonate (ATCC VR-925), Triniti (ATCC VR-469), Una (ATCC VR-374), Whataroa (ATCC VR-926), Y-62-33 (ATCC VR-375), O'Nyong virus, Eastern encephalitis virus (ATCC VR-65; ATCC VR-1242), Western encephalitis virus (ATCC VR-70; ATCC VR-1251; ATCC VR-622; ATCC VR-1252), and coronavirus (Hamre et al., *Proc. Soc. Exp. Biol. Med.* 121:190, 1966) (ATCC VR-740).

A polynucleotide of the invention can also be combined with a condensing agent to form a gene delivery vehicle. In a preferred embodiment, the condensing agent is a polycation, such as polylysine, polyarginine, polyornithine, protamine, spermine, spermidine, and putrescine. Many suitable methods for making such linkages are known in the art (see, for example. Ser. No. 08/366,787, filed Dec. 30, 1994).

In an alternative embodiment, a polynucleotide is associated with a liposome to form a gene delivery vehicle. Liposomes are small, lipid vesicles comprised of an aqueous compartment enclosed by a lipid bilayer, typically spherical or slightly elongated structures several hundred Angstroms in diameter. Under appropriate conditions, a liposome can fuse with the plasma membrane of a cell or with the membrane of an endocytic vesicle within a cell which has internalized the liposome, thereby releasing its contents into the cytoplasm. Prior to interaction with the surface of a cell, however, the liposome membrane acts as a relatively impermeable barrier which sequesters and protects its contents, for example, from degradative enzymes.

Because a liposome is a synthetic structure, specially designed liposomes can be produced which incorporate desirable features. See Stryer, *Biochemistry*, pp. 236-240, 1975 (W.H. Freeman, San Francisco, Calif.); Szoka et al., *Biochim. Biophys. Acta* 6001, 1980; Bayer et al., *Biochim. Biophys. Acta.* 550:464, 1979; Rivnay et al., *Meth. Enzymol.* 149:119, 1987; Wang et al., *Proc. Natl. Acad. Sci. U.S.A.* 84: 7851, 1987, Plant et al., *Anal. Biochem.* 176:420, 1989, and U.S. Pat. No. 4,762,915. Liposomes can encapsulate a variety of nucleic acid molecules including DNA, RNA, plasmids, and expression constructs comprising polynucleotides such those disclosed in the present invention.

Liposomal preparations for use in the present invention include cationic (positively charged), anionic (negatively charged) and neutral preparations. Cationic liposomes have been shown to mediate intracellular delivery of plasmid DNA (Felgner et al., *Proc. Natl. Acad. Sci. USA* 84:7413-7416, 1987), mRNA (Malone et al., *Proc. Natl. Acad. Sci. USA* 86:6077-6081, 1989), and purified transcription factors (Debs et al., *J. Biol. Chem.* 265:10189-10192, 1990); in functional form. Cationic liposomes are readily available. For example, N[1-2,3-dioleyloxy)propyl]-N,N,N-triethylammonium (DOTMA) liposomes are available under the trademark Lipofectin, from GIBCO BRL, Grand Island, N.Y. See also Felgner et al., *Proc. Natl. Acad. Sci. USA* 91: 5148-5152.87, 1994. Other commercially available liposomes include Transfectace (DDAB/DOPE) and DOTAP/DOPE (Boerhinger). Other cationic liposomes can be prepared from readily available materials using techniques well known in the art. See, e.g., Szoka et al., *Proc. Natl. Acad. Sci. USA* 75:4194-4198, 1978; and WO 90/11092 for descriptions of the synthesis of DOTAP (1,2-bis(oleoyloxy)-3-(trimethylammonio)propane) liposomes.

Similarly, anionic and neutral liposomes are readily available, such as from Avanti Polar Lipids (Birmingham, Ala.), or can be easily, prepared using readily available materials. Such materials include phosphatidyl choline, cholesterol, phosphatidyl ethanolamine, dioleoylphosphatidyl choline (DOPC), dioleoylphosphatidyl glycerol (DOPG), dioleoylphoshatidyl ethanolamine (DOPE), among others. These materials can also be mixed with the DOTMA and DOTAP starting materials in appropriate ratios. Methods for making liposomes using these materials are well known in the art.

The liposomes can comprise multilammelar vesicles (MLVs), small unilamellar vesicles (SUVs), or large unilamellar vesicles (LUVs). The various liposome-nucleic acid complexes are prepared using methods known in the art. See, e.g., Straubinger et al., METHODS OF IMMUNOLOGY (1983), Vol. 101, pp. 512-527; Szoka et al., *Proc. Natl. Acad. Sci. USA* 87.3410-3414, 1990; Papahadjopoulos et al., *Biochim. Biophys. Acta* 394:483, 1975; Wilson et al., *Cell* 17:77, 1979; Deamer and Bangham, *Biochim. Biophys. Acta* 443:629, 1976; Ostro et al., *Biochem. Biophys. Res. Commun.* 76:836, 1977; Fraley et al., *Proc. Natl. Acad. Sci. USA* 76:3348, 1979; Enoch and Strittmatter, *Proc. Natl. Acad. Sci. USA* 76:145, 1979; Fraley et al., *J. Biol. Chem.* 255:10431, 1980; Szoka and Papahadjopoulos, *Proc. Natl. Acad. Sci. USA* 75:145, 1979; and Schaefer-Ridder et al., *Science* 215:166, 1982.

In addition, lipoproteins can be included with a polynucleotide of the invention for delivery to a cell. Examples of such lipoproteins include chylomicrons, HDL, IDL, LDL, and VLDL. Mutants, fragments, or fusions of these proteins can also be used. Modifications of naturally occurring lipoproteins can also be used, such as acetylated LDL. These lipoproteins can target the delivery of polynucleotides to cells expressing lipoprotein receptors. Preferably, if lipoproteins are included with a polynucleotide, no other targeting ligand is included in the composition.

In another embodiment, naked polynucleotide molecules are used as gene delivery vehicles, as described in WO 90/11092 and U.S. Pat. No. 5,580,859. Such gene delivery vehicles can be either DNA or RNA and, in certain embodiments, are linked to killed adenovirus. Curiel et al. *Hum. Gene Ther.* 3:147-154, 1992. Other suitable vehicles include DNA-ligand (Wu et al., *J. Biol. Chem.* 264:16985-116987, 1989), lipid-DNA combinations (Felgner et al. *Proc. Natl. Acad. Sci. USA* 84:7413 7417, 1989), liposomes (Wang et al., *Proc. Natl. Acad. Sci.* 84:7851-7855, 1987) and microprojectiles (Williams et al., *Proc. Natl. Acad. Sci.* 88:2726-2730, 1991).

One can increase the efficiency of naked polynucleotide uptake into cells by coating the polynucleotides onto biodegradable latex beads. This approach takes advantage of the observation that latex beads, when incubated with cells in culture, are efficiently transported and concentrated in the perinuclear region of the cells. The beads will then be transported into cells when injected into muscle. Polynucleotide-coated latex beads will be efficiently transported into cells after endocytosis is initiated by the latex beads and thus increase gene transfer and expression efficiency. This method can be improved further by treating the beads to increase their hydrophobicity, thereby facilitating the disruption of the endosome and release of polynucleotides into the cytoplasm.

The invention also provides a method of detecting metastatic marker genes expression in a biological sample, such as a tissue sample of the breast or colon. Detection of metastatic marker genes expression is useful, for example, for identifying metastatic tissue and identifying metastatic potential of a tissue, to identify patients who are at risk for developing metastatic cancers in other organs of the body.

The tissue sample can be, for example, a solid tissue or a fluid sample. Protein or nucleic acid expression products can be detected in the tissue sample. In one embodiment, the tissue sample is assayed for the presence of a metastatic marker proteins. The metastatic marker protein has a sequence encoded by polynucleotides comprising SEQ ID NOS:1-18 and can be detected using the metastatic marker protein-specific antibodies of the present invention. The antibodies can be labeled, for example, with a radioactive, fluorescent biotinylated, or enzymatic tag and detected directly, or can be detected using indirect immunochemical methods, using a labeled secondary antibody. The presence of the metastatic marker proteins can be assayed, for example, in tissue sections by immunocytochemistry, or in lysates, using Western blotting, as is known in the art.

In another embodiment, the tissue sample is assayed for the presence of metastatic marker protein mRNA. Metastatic marker protein mRNA can be detected by in situ hybridization in tissue sections or in Northern blots containing poly A+ mRNA. Metastatic marker protein-specific probes may be generated using the cDNA sequences disclosed in SEQ ID NOS:1-18. The probes are preferably 15 to 50 nucleotides in length, although they may be 8, 10, 11, 12, 20, 25, 30, 35, 40, 45, 60, 75, or 100 nucleotides in length. The probes can be synthesized chemically or can be generated from longer polynucleotides using restriction enzymes. The probes can be labeled, for example, with a radioactive, biotinylated, or fluorescent tag. If desired, the tissue sample can be subjected to a nucleic acid amplification process.

A tissue sample in which an expression product of a polynucleotide comprising SEQ ID NOS:1, 4, 11, 16, 17, or 18 is detected is identified as metastatic or as having metastatic potential. A tissue sample in which an expression product of a polynucleotide comprising SEQ ID NOS:2, 3, 6, 7, 8, 9, 10, 12, 13, or 15 is identified as not metastatic or as having a low metastatic potential.

Propensity for high- or low-grade metastasis of a colon tumor can also be predicted, by measuring in a colon tumor sample an expression product of a gene comprising the nucleotide sequence of SEQ ID NOS:16 or 17. A colon tumor sample which expresses a product of a gene comprising the nucleotide sequence of SEQ ID NO:16 is categorized as having a high propensity to metastasize. A colon tumor sample which expresses a product of a gene comprising the nucleotide sequence of SEQ ID NO:17 is categorized as having a low propensity to metastasize.

Optionally, the level of a particular metastatic marker expression product in a tissue sample can be quantitated. Quantitation can be accomplished, for example, by comparing the level of expression product detected in the tissue sample with the amounts of product present in a standard curve. A comparison can be made visually or using a technique such as densitometry, with or without computerized assistance. For use as controls, tissue samples can be isolated from other humans, other non-cancerous organs of the patient being tested, or preferably non-metastatic breast or colon cancer from the patient being tested.

Polynucleotides encoding metastatic marker-specific reagents of the invention, such as antibodies and nucleotide probes, can be supplied in a kit for detecting them in a biological sample. The kit can also contain buffers or labeling components, as well as instructions for using the reagents to detect the metastatic marker expression products in the biological sample.

Metastatic marker gene expression in a cell can be increased or decreased, as desired. Metastatic marker genes expression can be altered for therapeutic purposes, as described below, or can be used to identify therapeutic agents.

In one embodiment of the invention, expression of a metastatic marker gene whose expression is upregulated in metastatic cancer is decreased using a ribozyme, an RNA molecule with catalytic activity. See, e.g., Cech, 1987, *Science* 236: 1532-1539; Cech, 1990, *Ann. Rev. Biochem.* 59:543-568; Cech, 1992, *Curr. Opin. Struct. Biol.* 2: 605-609; Couture and Stinchcomb, 1996, *Trends Genet.* 12: 510-515. Ribozymes can be used to inhibit gene function by cleaving an RNA sequence, as is known in the art (e.g., Haseloff et al., U.S. Pat. No. 5,641,673).

The coding sequence of the metastatic marker genes can be used to generate a ribozyme which will specifically bind to mRNA transcribed from a metastatic marker genes. Methods of designing and constructing ribozymes which can cleave other RNA molecules in trans in a highly sequence specific manner have been developed and described in the art (see Haseloff et al. (1988), *Nature* 334:585-591). For example, the cleavage activity of ribozymes can be targeted to specific RNAs by engineering a discrete "hybridization" region into the ribozyme. The hybridization region contains a sequence complementary to the target RNA and thus specifically hybridizes with the target (see, for example, Gerlach et al. EP 321,201). Longer complementary sequences can be used to increase the affinity of the hybridization sequence for the target. The hybridizing and cleavage regions of the ribozyme can be integrally related, thus, upon hybridizing to the target RNA through the complementary regions, the catalytic region of the ribozyme can cleave the target.

Ribozymes can be introduced into cells as part of a DNA construct, as is known in the art. The DNA construct can also include transcriptional regulatory elements, such as a promoter element, an enhancer or UAS element, and a transcriptional terminator signal, for controlling the transcription of the ribozyme in the cells.

Mechanical methods, such as microinjection, liposome-mediated transfection, electroporation, or calcium phosphate precipitation, can be used to introduce the ribozyme-containing DNA construct into cells whose division it is desired to decrease, as described above. Alternatively, if it is desired that the DNA construct be stably retained by the cells, the DNA construct can be supplied on a plasmid and maintained as a separate element or integrated into the genome of the cells, as is known in the art.

As taught in Haseloff et al., U.S. Pat. No. 5,641,673, the ribozyme can be engineered so that its expression will occur in response to factors which induce expression of the metastatic marker genes. The ribozyme can also be engineered to provide an additional level of regulation, so that destruction of mRNA occurs only when both the ribozyme and the metastatic marker genes are induced in the cells.

Expression of the metastatic marker genes can also be altered using an antisense oligonucleotide sequence. The antisense sequence is complementary to at least a portion of the coding sequence of a metastatic marker genes having the nucleotide sequence shown in SEQ ID NO:1-18. The complement of the nucleotide sequence shown in SEQ ID NO:1-18 consists of a contiguous sequence of nucleotides which form Watson-Crick basepairs with the contiguous nucleotide sequence shown in SEQ ID NO:1-18.

Preferably, the antisense oligonucleotide sequence is at least six nucleotides in length but can be about 8, 12, 15, 20, 25, 30, 35, 40, 45, or 50 nucleotides long. Longer sequences can also be used. Antisense oligonucleotide molecules can be provided in a DNA construct and introduced into cells whose division is to be decreased, as described above.

Antisense oligonucleotides can be composed of deoxyribonucleotides, ribonucleotides, or a combination of both. Oligonucleotides can be synthesized manually or by an automated synthesizer, by covalently linking the 5' end of one nucleotide with the 3' end of another nucleotide with non-phosphodiester internucleotide linkages such alkylphosphonates, phosphorothioates, phosphorodithioates, alkylphosphonothioates, alkylphosphonates, phosphoramidates, phosphate esters, carbamates, acetamidate, carboxymethyl esters, carbonates, and phosphate triesters. See Brown, 1994, *Meth. Mol. Biol.* 20:1-8. Sonveaux, 1994, *Meth. Mol. Biol.* 26:1-72; Uhlmann et al., 1990, *Chem. Rev.* 90:543-583.

Precise complementarity is not required for successful duplex formation between an antisense molecule and the complementary coding sequence of a metastatic marker gene. Antisense molecules which comprise, for example, 2, 3, 4, or 5 or more stretches of contiguous nucleotides which are precisely complementary to a portion of a coding sequence of a metastatic marker gene, each separated by a stretch of contiguous nucleotides which are not complementary to adjacent coding sequences, can provide targeting specificity for mRNA of a metastatic marker gene. Preferably, each stretch of contiguous nucleotides is at least 4, 5, 6, 7, or 8 or more nucleotides in length. Non-complementary intervening sequences are preferably 1, 2, 3, or 4 nucleotides in length. One skilled in the art can easily use the calculated melting point of an antisense-sense pair to determine the degree of mismatching which will be tolerated between a particular antisense oligonucleotide and a particular metastatic marker gene coding sequence.

Antisense oligonucleotides can be modified without affecting their ability to hybridize to a metastatic marker protein coding sequence. These modifications can be internal or at one or both ends of the antisense molecule. For example, internucleoside phosphate linkages can be modified by adding cholesteryl or diamine moieties with varying numbers of carbon residues between the amino groups and terminal ribose. Modified bases and/or sugars, such as arabinose instead of ribose, or a 3',5'-substituted oligonucleotide in which the 3' hydroxyl group or the 5' phosphate group are substituted, can also be employed in a modified antisense oligonucleotide. These modified oligonucleotides can be prepared by methods well known in the art. Agrawal et al., 1992, *Trends Biotechnol.* 10:152-158; Uhlmann et al., 1990, *Chem. Rev.* 90:543-584; Uhlmann et al., 1987, *Tetrahedron. Lett.* 215:3539-3542.

Antibodies of the invention which specifically bind to a metastatic marker protein can also be used to alter metastatic marker gene expression. Specific antibodies bind to the metastatic marker proteins and prevent the protein from functioning in the cell. Polynucleotides encoding specific antibodies of the invention can be introduced into cells, as described above.

To increase expression of metastatic marker genes which are down-regulated in metastatic cells, all or a portion of a metastatic marker gene or expression product can be introduced into a cell. Optionally, the gene or expression product can be a component of a therapeutic composition comprising a pharmaceutically acceptable carrier (see below). The entire coding sequence can be introduced, as described above. Alternatively, a portion of the metastatic marker protein or a nucleotide sequence encoding it can be introduced into the cell.

Expression of an endogenous metastatic marker genes in a cell can also be altered by introducing in frame with the endogenous metastatic marker genes a DNA construct comprising a metastatic marker protein targeting sequence, a regulatory sequence, an exon, and an unpaired splice donor site by homologous recombination, such that a homologously recombinant cell comprising the DNA construct is formed. The new transcription unit can be used to turn the metastatic marker genes on or off as desired. This method of affecting endogenous gene expression is taught in U.S. Pat. No. 5,641,670.

The targeting sequence is a segment of at least 10, 12, 15, 20, or 50 contiguous nucleotides selected from the nucleotide sequence shown in SEQ ID NO:1-18. The transcription unit is located upstream of a coding sequence of the endogenous metastatic marker protein gene. The exogenous regulatory sequence directs transcription of the coding sequence of the metastatic marker genes.

Expression of the metastatic marker proteins of the present invention can be used to screen for drugs which have a therapeutic anti-metastatic effect. The effect of a test compound on metastatic marker protein synthesis can also be used to identify test compounds which modulate metastasis. Synthesis of metastatic marker proteins in a biological sample, such as a cell culture, tissue sample, or cell-free homogenate, can be measured by any means for measuring protein synthesis known in the art, such as incorporation of labeled amino acids into proteins and detection of labeled metastatic marker proteins in a polyacrylamide gel. The amount of metastatic marker proteins can be detected, for example, using metastatic marker protein-specific antibodies of the invention in Western blots. The amount of the metastatic marker proteins synthesized in the presence or absence of a test compound can be determined by any means known in the art, such as comparison of the amount of metastatic marker protein synthesized with the amount of the metastatic marker proteins present in a standard curve.

The effect of a test compound on metastatic marker protein synthesis can also be measured by Northern blot analysis, by measuring the amount of metastatic marker protein mRNA expression in response to the test compound using metastatic marker protein specific nucleotide probes of the invention, as is known in the art. A test compound which decreases synthesis of a metastatic marker protein encoded by a polynucleotide comprising SEQ ID NOS:1, 4, 11, 16, 17, or 18 or which increases synthesis of a metastatic marker protein encoded by a polynucleotide comprising SEQ ID NOS:2, 3, 6, 7, 8, 9, 10, 12, 13, or 15 is identified as a possible therapeutic agent.

Typically, a biological sample, such as a breast or colon sample, is contacted with a range of concentrations of the test compound, such as 1.0 nM, 5.0 nM, 10 nM 50 nM, 100 nM, 500 nM, 1 mM, 10 mM, 50 mM, and 100 mM. Preferably, the test compound increases or decreases expression of a metastatic marker protein by 60%, 75%, or 80%. More preferably, an increase or decrease of 85%, 90%, 95%, or 98% is achieved.

The invention provides therapeutic compositions for increasing or decreasing expression of metastatic marker protein as is appropriate. Therapeutic compositions for increasing metastatic marker gene expression are desirable for metastatic markers down-regulated in metastatic cells. These comprise polynucleotides encoding all or a portion of a metastatic marker protein gene expression product. Preferably, the therapeutic composition contains an expression construct comprising a promoter and a polynucleotide segment encoding at least six contiguous amino acids of the metastatic marker protein. Within the expression construct, the polynucleotide segment is located downstream from the promoter, and transcription of the polynucleotide segment initiates at the promoter. A more complete description of gene transfer vectors, especially retroviral vectors is contained in U.S. Ser. No. 08/869,309.

Decreased metastatic marker gene expression is desired in conditions in which the metastatic marker gene is upregulated in metastatic cancer. Therapeutic compositions for treating these disorders comprise a polynucleotide encoding reagent which specifically binds to a metastatic marker protein expression product, as disclosed herein.

Metastatic marker therapeutic compositions of the invention also comprise a pharmaceutically acceptable carrier. Pharmaceutically acceptable carriers are well known to those in the art. Such carriers include, but are not limited to, large, slowly metabolized macromolecules such as proteins, polysaccharides, polylactic acids, polyglycolic acids, polymeric amino acids, amino acid copolymers, and inactive virus particles. Pharmaceutically acceptable salts can also be used in the composition, for example, mineral salts such as hydrochlorides, hydrobromides, phosphates, or sulfates, as well as the salts of organic acids such as acetates, propionates, malonates, or benzoates.

Therapeutic compositions can also contain liquids, such as water, saline, glycerol, and ethanol, as well as substances such as wetting agents, emulsifying agents, or pH buffering agents. Liposomes, such as those described in U.S. Pat. No. 5,422,120, WO 95/13796, WO 91/14445, or EP 524,968 B1, can also be used as a carrier for the therapeutic composition.

Typically, a therapeutic metastatic marker composition is prepared as an injectable, either as a liquid solution or suspension; however, solid forms suitable for solution in, or suspension in, liquid vehicles prior to injection can also be prepared. A metastatic marker composition can also be formulated into an enteric coated tablet or get capsule according to known methods in the art, such as those described in U.S. Pat. No. 4,853,230, EP 225,189, AU 9,224,296, and AU 9,230,801.

Administration of the metastatic marker therapeutic agents of the invention can include local or systemic administration, including injection, oral administration, particle gun, or catheterized administration, and topical administration. Various methods can be used to administer a therapeutic metastatic marker composition directly to a specific site in the body.

For treatment of tumors, for example, a small tumor or metastatic lesion can be located and a therapeutic metastatic marker composition injected several times in several different locations within the body of tumor. Alternatively, arteries which serve a tumor can be identified, and a therapeutic composition injected into such an artery, in order to deliver the composition directly into the tumor.

A tumor which has a necrotic center can be aspirated and the composition injected directly into the now empty center of the tumor. A therapeutic metastatic marker composition can be directly adminstered to the surface of a tumor, for example, by topical application of the composition. X-ray imaging can be used to assist in certain of the above delivery methods. Combination therapeutic agents, including an the metastatic marker protein, polypeptide, or subgenomic polynucleotide and other therapeutic agents, can be administered simultaneously or sequentially.

Receptor-mediated targeted delivery can be used to deliver therapeutic compositions containing subgenomic polynucleotides, proteins, or reagents such as antibodies, ribozymes, or antisense oligonucleotides to specific tissues. Receptor-mediated delivery techniques are described in, for example, Findeis et al. (1993), *Trends in Biotechnol.* 11, 202-05; Chiou et al. (1994), GENE THERAPEUTICS: METHODS AND APPLICATIONS OF DIRECT GENE TRANSFER (J. A. Wolff, ed.); Wu & Wu (1988), *J. Biol. Chem.* 263, 621-24; Wu et al. (1994), *J. Biol. Chem.* 269, 542-46; Zenke et al. (1990), *Proc. Natl. Acad. Sci. U.S.A.* 87, 3655-59; Wu et al. (1991), *J. Biol. Chem.* 266, 338-42.

Alternatively, a metastatic marker therapeutic composition can be introduced into human cells ex vivo, and the cells then replaced into the human. Cells can be removed from a variety of locations including, for example, from a selected tumor or from an affected organ. In addition, a therapeutic composition can be inserted into non-affected, for example, dermal fibroblasts or peripheral blood leukocytes. If desired, particular fractions of cells such as a T cell subset or stem cells can also be specifically removed from the blood (see, for example, PCT WO 91/16116). The removed cells can then be contacted with a metastatic marker therapeutic composition utilizing any of the above-described techniques, followed by the return of the cells to the human, preferably to or within the vicinity of a tumor or other site to be treated. The methods described above can additionally comprise the steps of depleting fibroblasts or other non-contaminating tumor cells subsequent to removing tumor cells from a human, and/or the step of inactivating the cells, for example, by irradiation.

Both the dose of a metastatic marker composition and the means of administration can be determined based on the specific qualities of the therapeutic composition, the condition, age, and weight of the patient, the progression of the disease, and other relevant factors. Preferably, a therapeutic composition of the invention increases or decreases expression of the metastatic marker genes by 50%, 60%, 70%, or 80%. Most preferably, expression of the metastatic marker genes is increased or decreased by 90%, 95%, 99%, or 100%. The effectiveness of the mechanism chosen to alter expression of the metastatic marker genes can be assessed using methods well known in the art, such as hybridization of nucleotide probes to mRNA of the metastatic marker genes, quantitative RT-PCR, or detection of metastatic marker proteins using specific antibodies.

If the composition contains the metastatic marker proteins, polypeptide, or antibody, effective dosages of the composition are in the range of about 5 µg to about 50 µg/kg of patient body weight, about 50 µg to about 5 mg/kg, about 100 µg to about 500 µg/kg of patient body weight, and about 200 to about 250 µg/kg.

Therapeutic compositions containing metastatic marker subgenomic polynucleotides can be administered in a range of about 100 ng to about 200 mg of DNA for local administration in a gene therapy protocol. Concentration ranges of about 500 µg to about 50 mg, about 1 µg to about 2 mg, about 5 µg to about 500 µg, and about 20 µg to about 100 µg of DNA can also be used during a gene therapy protocol. Factors such as method of action and efficacy of transformation and expression are considerations that will affect the dosage required for ultimate efficacy of the metastatic marker protein subgenomic polynucleotides. Where greater expression is desired over a larger area of tissue, larger amounts of metastatic marker protein subgenomic polynucleotides or the same amounts readministered in a successive protocol of administrations, or several administrations to different adjacent or close tissue portions of, for example, a tumor site, may be required to effect a positive therapeutic outcome. In all cases, routine experimentation in clinical trials will determine specific ranges for optimal therapeutic effect.

Metastatic marker subgenomic polynucleotides of the invention can also be used on polynucleotide arrays. Polynucleotide arrays provide a high throughput technique that can assay a large number of polynucleotide sequences in a single sample. This technology can be used, for example, as a diagnostic tool to identify metastatic lesions or to assess the metastatic potential of a tumor.

To create arrays, single-stranded polynucleotide probes can be spotted onto a substrate in a two-dimensional matrix or array. Each single-stranded polynucleotide probe can comprise at least 6, 7, 8, 9, 10, 11, 12, 13, 14, 15, 16, 17, 18, 19, 20, 25, or 30 or more contiguous nucleotides selected from the nucleotide sequences shown in SEQ ID NOS:1-18. Preferred arrays comprise at least one single-stranded polynucleotide probe comprising at least 6, 7, 8, 9, 10, 11, 12, 13, 14, 15, 16, 17, 18, 19, 20, 25, or 30 or more contiguous nucleotides selected from the nucleotide sequences shown in SEQ ID NOS:1, 4, 11, 16, 17, and 18. Other preferred arrays comprise at least one single-stranded polynucleotide probe comprising at least 6, 7, 8, 9, 10, 11, 12, 13, 14, 15, 16, 17, 18, 19, 20, 25, or 30 or more contiguous nucleotides selected from the nucleotide sequences shown in SEQ ID NOS:2, 3, 6, 7, 9, 10, 12, 13, and 15. Still other preferred arrays comprise at least one single-stranded polynucleotide probe comprising at least 6, 7, 8, 9, 10, 11, 12, 13, 14, 15, 16, 17, 18, 19, 20, 25, or 30 or more contiguous nucleotides selected from the nucleotide sequences shown in SEQ ID NOS: 5 and 14 or SEQ ID NOS:16 and 17.

The substrate can be any substrate to which polynucleotide probes can be attached, including but not limited to glass, nitrocellulose, silicon, and nylon. Polynucleotide probes can be bound to the substrate by either covalent bonds or by non-specific interactions, such as hydrophobic interactions. Techniques for constructing arrays and methods of using these arrays are described in EP No. 0 799 897; PCT No. WO 97/29212; PCT No. WO 97/27317; EP No. 0 785 280; PCT No. WO 97/02357; U.S. Pat. No. 5,593,839; U.S. Pat. No. 5,578,832; EP No. 0 728 520; U.S. Pat. No. 5,599,695; EP No. 0 721 016; U.S. Pat. No. 5,556,752; PCT No. WO 95/22058; and U.S. Pat. No. 5,631,734. Commercially available polynucleotide arrays, such as Affymetrix GeneChip™, can also be used. Use of the GeneChip™ to detect gene expression is described, for example, in Lockhart et al., *Nature Biotechnology* 14:1675 (1996); Chee et al., *Science* 274:610 (1996); Hacia et al., *Nature Genetics* 14:441, 1996; and Kozal et al., *Nature Medicine* 2:753, 1996.

Tissue samples which are suspected of being metastatic of the metastatic potential of which is unknown can be treated to form single-stranded polynucleotides, for example by heating or by chemical denaturation, as is known in the art. The single-stranded polynucleotides in the tissue sample can then be labeled and hybridized to the polynucleotide probes on the array. Detectable labels which can be used include but are not limited to radiolabels, biotinylated labels, fluorophors, and chemiluminescent labels. Double stranded polynucleotides, comprising the labeled sample polynucleotides bound to polynucleotide probes, can be detected once the unbound portion of the sample is washed away. Detection can be visual or with computer assistance.

Detection of a double-stranded polynucleotide comprising contiguous nucleotides selected from the group consisting of SEQ ID NOS:1-4, 11, 16, 17, and 18 or lack of detection of a double-stranded polynucleotide comprising contiguous nucleotides selected from the group consisting of SEQ ID NOS:2, 3, 6, 7, 8, 9, 10, 12, 13, and 15 identifies the tissue sample as metastatic or of having metastatic potential.

All of the references cited in this disclosure are expressly incorporated herein by reference. The above disclosure generally describes the present invention. A more complete understanding can be obtained by reference to the following specific examples which are provided herein for purposes of illustration only and are not intended to limit the scope of the invention.

EXPERIMENTAL PROCEDURES

The following materials and methods were used in the examples below.

Cell lines. Cell lines MCF-7, BR-3, BT-20, ZR-75-1, MDA-MB-157, MDA-MB-231, MDA-MB-361, MDA-MB-435, MDA-MB-453, MDA-MB-468, Alab, and Hs578Bst were obtained from American Type Culture Collection. All cell lines were grown according to their specifications.

Differential Display. Differential display was performed using the Hieroglyph mRNA profile kit according to the manufacturer's directions (Genomyx Corp., Foster City, Calif.). A total of 200 primer pairs were used to profile gene expression. Following amplification of randomly primed mRNAs by reverse-transcription-polymerase chain reaction RT-PCR), the cDNA products were separated on 6% sequencing-type gels using a genomyxLR sequencer (Genomyx Corp). The dried gels were exposed to Kodak XAR-2 film Kodak, Rochester, N.Y.) for various times.

Differentially-expressed cDNA fragments were excised and reamplified according to the manufacturer's directions (Genomyx Corp.). Because a gel slice excised from the gel contains 1 to 3 cDNA fragments of the same size (Martin et al., *BioTechniques* 24, 1018-26, 1998; Giese et al., Differential Display, Academic Press, 1998), reamplified products were separated by single strand confirmation polymorphism gels as described in (Mathieu-Dande et al., *Nucl. Acids Res.* 24, 1504-07, 1996) and directly sequenced using M13 universal and T7 primers.

Construction and screening of human bone marrow stromal cell cDNA library. RNA was isolated from human bone marrow stromal cells (Poietic Technologies, Inc., Germantown, Md.) using a guanidinium thiocyanate/phenol chloroform extraction protocol (Chirgwin et al., *Biochem.* 18, 5294-99, 1979). Poly(A)$^+$ RNA was isolated using oligo-dT spin columns (Stratagene, La Jolla, Calif.). First and second strand synthesis was carried out according to the manufacturer's instructions (Pharmacia, Piscataway, N.J.). Double-stranded cDNA was ligated into pBK-CMV phagemid vector (Stratagene, La Jolla, Calif.). Approximately, $1 \times 10^6$ plaques were screened using a 1.2 kb CSP56 cDNA fragment. Plasmid DNA from positive clones was obtained according to the manufacturer's instructions. Correctness of the nucleotide sequence was determined by double-strand sequencing.

Northern blot analysis and RT-PCR. Northern blots containing poly(A)$^+$ RNA prepared from various human normal and tumor tissues were purchased from ClonTech (Palo Alto, Calif.) and Biochain Institute (San Leandro, Calif.). All other Northern blots were prepared using 20 to 30 µg total RNA isolated using a guanidinium thiocyanate/phenol chloroform extraction protocol (Chirgwin et al., 1979) from different human breast cancer and normal cell lines. Northern blots were hybridized at 65° C. in Express-hyb (ClonTech).

RT-PCR was performed using the reverse transcriptase RNA PCR kit (Perkin-Elmer, Roche Molecular Systems, Inc., Branchburg, N.J.) according to the manufacturer's instructions.

In situ hybridization. In situ hybridization was performed on human tissues, frozen immediately after surgical removal and cryosection at 10 µm; following the protocol of Pfaff et al., *Cell* 84, 309-20, 1996. Digoxigenin-UTP-labeled riboprobes were generated using the CSP56-containing plasmid DNA as a template. For generation of the antisense probe, the DNA was linearized with EcoRI (approximately 1 kb transcript) or NcoI (full-length transcript) and transcribed with T3 polymerase. For the sense control, the DNA was linearized with XhoI (full-length transcript) and transcribed with T7 polymerase. Hybridized probes were detected with alkaline phosphatase-coupled anti-digoxigenen antibodies using BM Purple as the substrate (Boehringer Mannheim).

Tumor growth in the mammary fatpad of immunodeficient mice. Scid (severe combined immunodeficient) mice (Jackson Laboratory) were anesthetized, and a small incision was made to expose the mammary fatpad. Approximately $4 \times 10^6$ cells were injected into the fatpad of each mouse. Tumor growth was monitored by weekly examination, and growth was determined by caliper measurements. After approximately 4 weeks, primary tumors were removed from anesthetized mice, and the skin incisions were closed with wound clips. Approximately 4 weeks later, mice were killed and inspected for the presence of lung metastases. Primary tumors and lung metastasis were analyzed histologically for the presence of human cells. A chunk of tumor tissue representing more than 80% cells of human origin was used to isolate total RNA. In the case of MDA-MD-435, large lung metastases representing more than 90% human cells were used. Total RNA was amplified by RT-PCR using specific primers for the CSP56 coding region. The reaction products were dot blotted onto nylon membranes and hybridized with a CSP56-specific probe.

Example 1

This example demonstrates identification of a differentially-expressed gene in the aggressive-invasive human breast cancer cell line MDA-MB-435.

To identify genes associated with the metastatic phenotype, we compared the gene expression profiles in four human breast cancer cell lines using which display different malignant phenotypes, MDA-MB-453, MCF-7, MDA-MB-231, and MDA-MB-435, ranging from poorly-invasive to most aggressively-invasive (Engel et al., Cancer Res. 38, 4327-39, 1978; Shafie and Liotta, Cancer Lett. 11, 81-87, 1990; Ozello and Sordat, Eur. J. Cancer 16, 553-59, 1980; Price et al., Cancer Res. 50, 717-21, 1990). Cell lines were chosen as staring material based on the ability to obtain high amounts of pure RNA. In contrast, human breast cancer biopsies consist of a mixture of cancer and other cell types including macrophages and lymphocytes (Kelly et al., Br. J. Cancer 57, 174-77, 1988; Whitford et al., Br. J. Cancer 62, 971-75, 1990). The described human breast cancer cell lines have been extensively studied in mouse models allowing one to functionally characterize identified candidate genes in tumor progression.

To ensure that the cell lines retained their original malignant properties after prolonged passage in culture, we examined their potential to grow in scid mice and to form metastasis following injection into the mammary fatpad. Three of the four cell lines formed primary tumors, consistent with previous reports (Engel et al., 1978; Shafie and Liotta, 1990; Ozello and Sordat, 1980; Price et al., 1990). No primary tumor formation was detected with MDA-MB-453. In addition, mice injected with MDA-MB-231 and MDA-MB-435 developed lung metastases, with the highest incidence being detected using MDA-MB-435.

Next, we performed a differential display analysis using total RNA isolated from the breast cancer cell lines and a total of 200 different primer pair combinations. Among several differentially expressed transcripts, a 1.2-kb cDNA fragment was specifically amplified from the MDA-MB-435 RNA sample using the primer pair combination, Ap8 [5'-ACGACTCACTATAGG GC(T)$_{12}$AA] (SEQ ID NO:20) and Arp1 (5'-ACAATTTCACACAGGACGACTCCAAG) (SEQ ID NO:21) (FIG. 1A, lanes 5 and 6). Weak expression was also detected in MDA-MB-231 (FIG. 1A, lanes 1 and 2), whereas no signal was detected in the RNA samples isolated from MCF-7 and MDA-MB-453 (FIG. 1A, lanes 3, 4, 7, and 8).

Figure 1B:
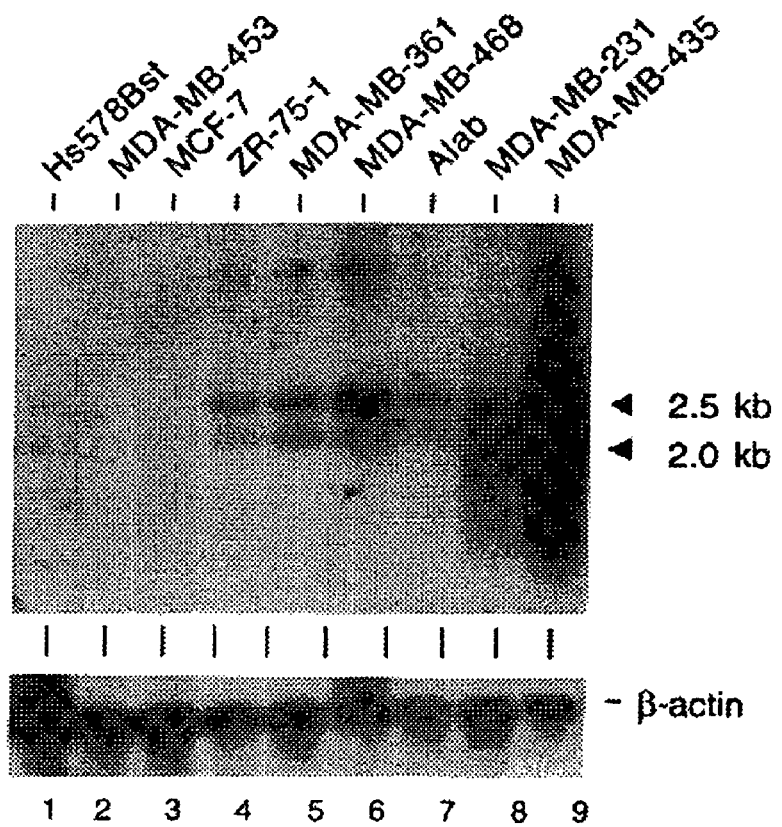
FIG. 1B. Northern blot analysis verifying the expression pattern in MDA-MB-435. cDNA isolated from the differential display gel hybridized to two transcripts of approximately 2.0 kb and 2.5 kb in size. Equal amounts of RNA in each lane were loaded as judged by staining of the membrane with methylene blue and hybridization of the membrane with a human β-actin probe.

To confirm the expression pattern, the DNA fragment was isolated from the gel, reamplified, radiolabeled, and used as a hybridization probe in a Northern blot analysis of human breast cancer cell lines with different malignant phenotypes and a non-tumorigenic breast cell line (FIG. 1B). The radioactive probe hybridized with similar intensity to two transcripts of approximately 2.0-kb and 2.5-kb in size in the MDA-MB-435 RNA sample (lane 9). Weak expression of these transcripts was detected in the poorly invasive human breast cell lines (lanes 2 and 3) or in the non-tumorigenic line Hs578Bst (lane 1). No signal was detected in MDA-MB-453 and MCF-7. These data show a restricted expression pattern of this gene to highly or moderately metastatic human breast cancer cell lines.

Example 2

This example demonstrates the nucleotide sequence of CSP56 cDNA.

Comparison of the nucleotide sequence of CSP56 cDNA to public databases showed no significant homologies. To obtain more nucleotide sequence information, we screened a human bone marrow stromal cell cDNA library. One of the positive clones extended the original clone to 1855 nucleotides in length (FIG. 2A). This sequence was further extended at the 3'-end with several expressed sequenced tags to 2606 nucleotides in length (FIG. 2B). The additional 750 nucleotides are most probably the result of alternative poly-A site selection.

Analysis of the nucleotide sequence revealed a single open reading frame of 518 amino acids, beginning with a start codon for translation at nucleotide position 101 and terminating with a stop codon at nucleotide position 1655, A consensus Kozak sequence (Kozak, Cell 44, 283-92, 1986) around the start codon and the analysis of the codon usage (Wisconsin package, UNIX) suggests that this cDNA clone contains the entire coding region.

Translation of the open reading frame predicts a protein with a molecular mass of 56 kD. On the basis of its specific expression in the highly metastatic human breast cancer cell lines, the cDNA-encoded protein was termed CSP56 for cancer-specific protein 56-kd.

Example 3

This example demonstrates that CSP56 is a novel aspartyl-type protease.

Comparison of the CSP56 open reading frame with proteins in public databases shows some homology to members of the pepsin family of aspartyl proteases (FIG. 3). A characteristic feature of this protease family is the presence of two active centers which evolved by gene duplication (Davies, Ann. Rev. Biophys. Biochem. 19, 189-215, 1990; Neil and Barrett, Meth. Enz. 248, 105-80, 1995). The amino acid residues comprising the catalytic domains (Asp-Thr/Ser-Gly) and the flanking residues display the highest conservation in this family and are conserved in CSP56 (FIGS. 2 and 3).

CSP56, however, shows structural features which are distinct from other aspartyl proteases. Overall similarities of CSP56 to pepsinogen C and A, renin, and cathepsin D and E are only 55, 51, 54, 52, and 51%, respectively, neglecting the CSP56 C-terminal extension. The cysteine residues found following and preceding the catalytic domains in other members are absent in CSP56 (FIG. 3). CSP56 also contains a carboxy-terminal extension of approximately 90 amino acid residues which shows no significant homology to known proteins.

CSP56 also contains a hydrophobic motif consisting of 29 amino acid residues in the C-terminal extension which may function as a membrane attachment domain. (FIGS. 2C and 3) CSP56 also contains a putative signal sequence.

CSP56 is therefore a novel aspartyl-type protease with a putative transmembrane domain (amino acids 8-20) and a stretch of approximately 45 amino acids representing a putative propeptide (amino acids 21 to 76).

Example 4

This example demonstrates the expression pattern of CSP56 throughout human breast cancer development and in metastasis.

Figure 4:
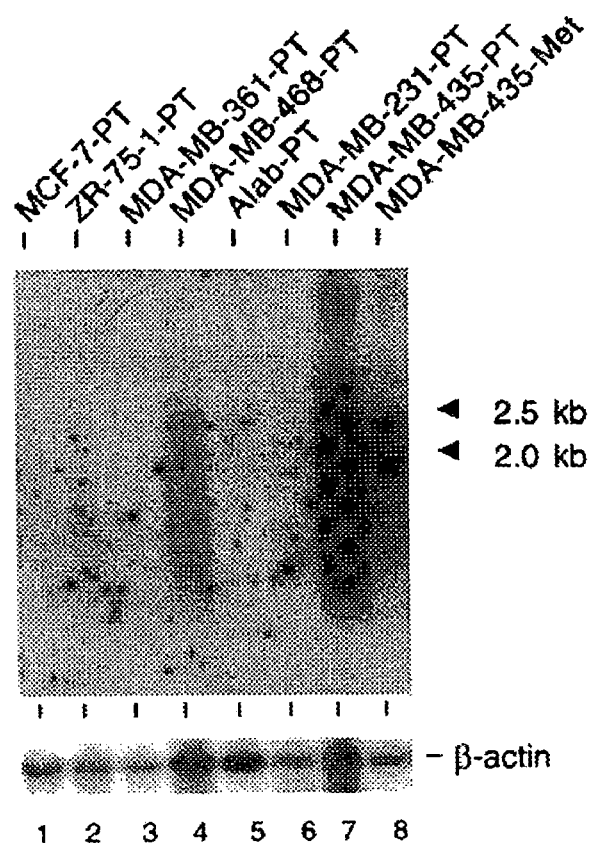
FIG. 4. CSP56 expression in primary tumor and metastases isolated from scid mice. Northern blot analysis using RNA isolated from primary tumors (PT) and metastatic tissues (Met) of mice injected with different human breast cancer cell lines. Equal amounts of RNA in each lane were loaded as judged by staining of the membrane with methylene blue and hybridization of the membrane with a human β-action probe.

To further examine the expression pattern of CSP56, we performed a Northern blot analysis using additional human breast cancer and normal cell lines (FIG. 4). Expression of CSP56 was detected in MDA-MB-435, MDA-MB-468, and BR-3 (lanes 1, 4, and 9), with the strongest signal in MDA-MB-435. Other cell lines showed weak expression. No signal was detected in the poorly-invasive human breast cancer cell lines MDA-MB-453 and MCF-7 and in a normal breast cell line Hs578Bst. Together, these data are consistent with the increased expression of CSP56 in highly malignant human breast cancer cell lines.

Example 5

This example demonstrates the expression pattern of CSP56 in normal human tissues.

Figure 7:
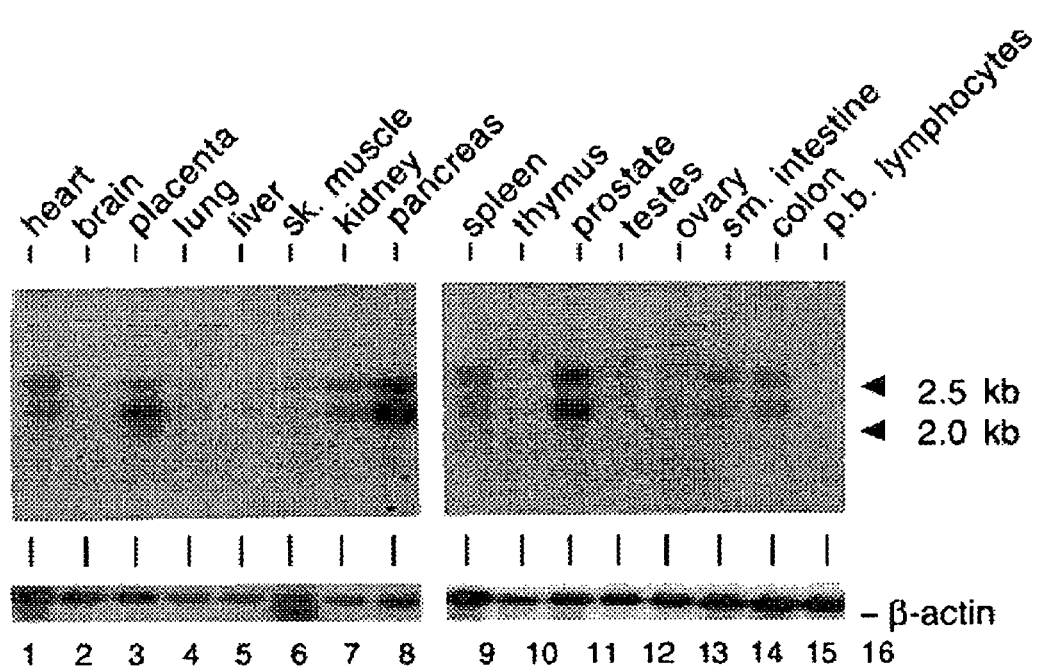
FIG. 7. Expression of CSP56 in human tissues. RNA blot analysis depicting two CSP56 transcripts of 2.0 kb and 2.5 kb in various human tissues. sk. muscle, skeletal muscle; sm. intestine, small intestine; p.b. lymphocytes, peripheral blood lymphocytes.

To determine the tissue distribution of CSP56, polyA+ RNA from various human tissues was examined by Northern blot analysis (FIG. 7). Two major transcripts were detected that are similar in size to those detected in cancer cell lines and human tissues. Highest expression was detected in pancreas, prostate, and placenta. Weak or no signal was detected in brain and peripheral blood lymphocytes.

Example 6

This example demonstrates identification of CSP56 transcripts in primary tumors and metastatic lung tissue isolated from immunodeficient mice injected with MDA-MB-435.

The scid mouse model was used to examine CSP56 expression in tumors. This model has been shown to be suitable for evaluating the function of genes implicated in the tumorigenicity and metastasis of human breast cancer cells (Steeg et al., *Breast Cancer Res. Treat.* 25, 175-87, 1993; Price, *Breast Cancer Res. Treat* 39, 93-102, 1996).

Different human breast cancer cell lines were injected into the mammary fatpad of immunodeficient mice. Primary tumors and, if applicable, lung metastases were isolated from mice, and total RNA was prepared for Northern blot analysis (FIG. 4).

CSP56 transcripts were detected in primary tumor RNA derived from MDA-MB-435, MDA-MB-468 and Alab, but not from MCF-7 (FIG. 4). CSP56 gene expression was also detected in lung metastasis of mice injected with MDA-MB-435 (lane 1). Failure to detect CSP56 transcripts in primary tumors of mice injected with ZR-75-1, MDA-MB-361, and MDA-MB-231 could be explained with the small amount of human cancer tissues in these tumors as judged by the weak human β-actin signal when compared to other primary tumor RNA samples.

Together these data exclude in vitro culture conditions as a cause for CSP56 up-regulation and establishes this gene as a novel tumor maker.

Example 7

This example demonstrates detection of CSP56 gene expression detected in patient samples.

Figures 5A, 5B:
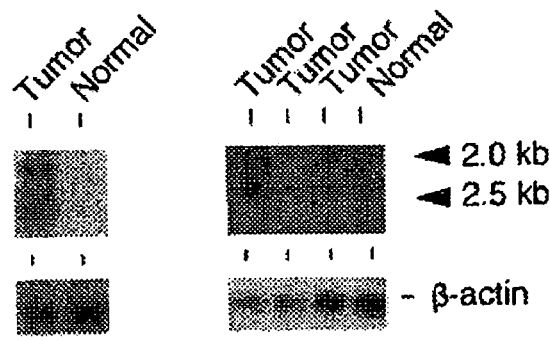
FIG. 5A. Northern blot analysis using RNA isolated from tumor and normal breast tissue from the same patient.
FIG. 5B. Northern blot analysis using RNA isolated from three different human breast tumor patients and normal breast tissue.

CSP56 expression was examined in RNA samples isolated from patient tumor biopsies. A Northern blot containing total RNA from breast tumor tissue and normal breast tissue from the same patient was hybridized with a CSP56-specific probe (FIG. 5A) CSP56 transcripts were detected in the tumor sample whereas no signal was detected in the normal breast RNA (lanes 1 and 2). Similarly) expression of CSP56 transcripts were up-regulated in two other breast cancer RNA samples when compared to a normal breast RNA control (FIG. 5B). Increased expression of CSP56 was also detected in human colon cancer tissue when compared to normal colon tissue of the same patient.

Figures 6A, 6B, 6C:
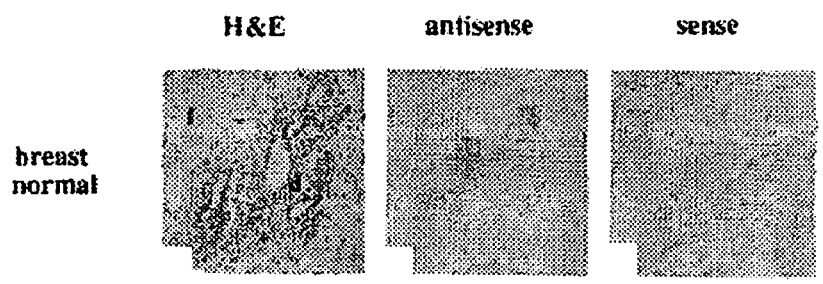
FIG. 6. In situ hybridization analysis of CSP56 expression in breast and colon tumors. Adjacent or near-adjacent sections through normal breast tissue (A-C) and the primary breast tissue (D-F) of one patient and through normal colon tissue (C, H), the primary colon tumor (J, K), and the liver metastatis (L, M) of another patient. Sections A, D, G, J, and L were stained with haematoxylin and eosin (H & E). Sections B, E, H, K, and M were hybridized with the antisense CSP56 probe, and sections C and F were hybridized with the CSP56 sense control probe. d, lactiferous duct; f, fatty connective tissue; ly, lymphocytes; m, colon mucosa; met, metastatic tissue; PT, primary tumor; st, stroma; tc, tumor cells.
Figures 6D, 6E, 6F:
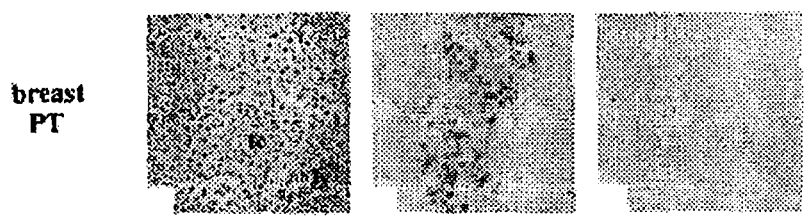

To identify the cell types that express CSP56 transcripts in vivo, we performed an in situ hybridization analysis on tissue samples obtained from one breast cancer patient (FIG. 6A-6F). A weak CSP56 signal was detected in the cells of the ducts of normal breast tissue (FIG. 6B). In the primary tumor, CSP56 was highly expressed in the tumor cells but not in the surrounding lymphocytes (FIG. 6E). No signal was detected using the sense probe (FIGS. 6C and 6F).

Figures 6G, 6H:
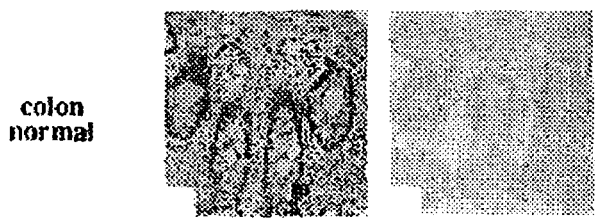
Figures 6J, 6K:
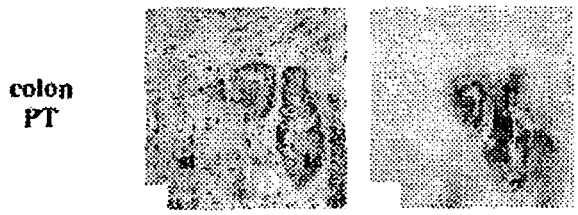
Figures 6L, 6M:
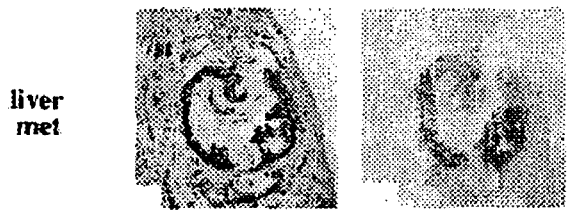

We also analyzed tissue samples obtained from two colon cancer patients (FIGS. 6G-6M) for CSP56 expression. No signal was detected in normal colon tissue (FIG. 6H), whereas CSP56 transcripts were abundant in the tumor cells of both the primary colon tumor and the liver metastasis, and no expression was detected in the surrounding stroma (FIGS. 6K and 6M).

These data demonstrate that CSP56 is over-expressed in tumor cells of human cancer patients and may play a role in the development and progression of different types of tumors.

TABLE 1

| TRANSCRIPT NUMBER | SEQ ID NO: and Figure No. | non-metastatic breast | breast cancer metastatic to bone | breast cancer metastatic to lung | low metastatic from colon | high metastatic from colon |
|---|---|---|---|---|---|---|
| 122 | 1 | – | – | + | | |
| 156 | 2 | + | – | – | | |
| 166 | 3 | + | – | – | | |
| 172 | 4 | – | – | + | | |
| 245 | 5 | + | + | – | | |
| 280 | 6 | + | – | – | | |
| 288 | 7 | + | – | – | | |
| 337 | 8 | + | – | – | | |
| 344 | 9 | + | – | – | | |
| 355 | 10 | + | – | – | | |
| 42 | 11 | – | – | + | | |
| 59 | 12 | + | – | – | | |
| 87 | 13 | + | – | – | | |
| 310 | 14 | + | + | – | | |
| 349 | 15 | + | – | – | | |
| 362c | 16 | | | | – | + |
| 305c | 17 | | | | + | – |

+ indicates that the transcript is detectable in Northern blots.
– indicates that the transcript is not detectable in Northern blots.
Some transcripts are detectable upon RT-PCR even when not detectable in Northern blots.

SEQUENCE LISTING

<160> NUMBER OF SEQ ID NOS: 27

<210> SEQ ID NO 1
<211> LENGTH: 2429
<212> TYPE: DNA
<213> ORGANISM: human

```
<400> SEQUENCE: 1
acaagttgca cttaagaagc tatgctaaga aaacaaacac acagaagcct acatcattac      60
atgtatagaa tgttcaagaa ctgatgaaac cagtccgtgg tcacaaaagc cagaaagtgg     120
ttgcttctgg ggaccagaag ggaaaggggc ataaggaac cttttgaggt gaatagaagt      180
ttctgcatct tggtttggca cacatgccaa aactcaccag ctacagattc tcgttgacac     240
tggaagcagt aactttgccg tgcaggaaac cccgcactcc tacatagaca cgtactttga     300
cacagagagg tctagcacat accgctccaa gggctttgac gtcacagtga agtacacaca     360
aggaagctga cgggcttcg ttggggaaga cctcgtcacc atccccaaag gcttcaatac      420
ttcttttctt gtcaacattg ccactatttt tgaatcagag aatttctttt tgcctgggat     480
taaatggaat ggaatacttg gcctagctta tgccacactt gccaagccat caagttctct     540
ggagaccttc ttcgactccc tggtgacaca agcaaacatc cccaacgttt tctccatgca    600
gatgtgtgga gccggcttgc ccgttgctgg atctgggacc aacggaggta gtcttgtctt    660
gggtggaatt gaaccaagtt tgtataaagg agacatctgg tatacccta ttaaggaaga     720
gtggtactac cagatagaaa ttctgaaatt ggaaattgga ggccaaagcc ttaatctgga    780
ctgcagagag tataacgcag acaaggccat cgtggacagt ggcaccacgc tgctgcgcct    840
gcccagaaag gtgtttgatg cggtggtgga agctgtggcc cgcgcatctc tgattccaga    900
attctctgat ggtttctgga ctgggtccca gctggcgtgc tggacgaatt cggaaacacc    960
ttggtcttac ttccctaaaa tctccatcta cctgagagat gagaactcca gcaggtcatt   1020
ccgtatcaca atcctgcctc agctttacat tcagcccatg atgggggccg gcctgaatta   1080
tgaatgttac cgattcggca tttccccatc cacaaatgcg ctggtgatcg gtgccacggt   1140
gatggagggc ttctacgtca tcttcgacag agcccagaag agggtgggct cgcagcgag   1200
cccctgtgca gaaattgcag gtgctgcagt gtctgaaatt tccgggcctt tctcaacaga   1260
ggatgtagcc agcaactgtg tccccgctca gtctttgagc gagcccattt tgtggattgt   1320
gtcctatgcg ctcatgagcg tctgtggagc catcctcctt gtcttaatcg tcctgctgct   1380
gctgccgttc cggtgtcagc gtcgcccccg tgaccctgag gtcgtcaatg atgagtcctc   1440
tctggtcaga catcgctgga atgaatagc caggcctgac ctcaagcaac catgaactca    1500
gctattaaga aaatcacatt tccagggcag cagccgggat cgatggtggc gctttctcct   1560
gtgcccaccc gtcttcaatc tctgttctgc tcccagatgc cttctagatt cactgtcttt   1620
tgattcttga ttttcaagct ttcaaatcct ccctacttcc aagaaaaata attaaaaaaa   1680
aaacttcatt ctaaaccaaa acagagtgga ttgggctgca ggctctatgg ggttcgttat   1740
gccaaagtgt ctacatgtgc caccaacata aaacaaaacc aagccttggc tcgttctctt   1800
ctctcttcaa tctctggaaa aataagtaca tatagttgat accccctctt agcttacagg   1860
aagcttttg tattaattgc ctttgaggtt attttccgcc agacctcaac ctgggtcaaa     1920
gtggtacagg aaggcttgca gtatgatggc aggagaatca gcctgggcc tggggatgta    1980
accaagctgt acccttgaga cctggaacca gagccacagg ccccttttgt gggtttctct   2040
gtgctctgaa tgggagccag aattcactag gaggtcatca accgatggtc ctcacaagcc   2100
tcttctgaag atgaaggcc ttttgcccgt tgaggtagag gggaaggaaa tctcctcttt     2160
tgtaccccaat acttatgttg tattgttggt gcgaaagtaa aaacactacc tcttttgaga   2220
cttgcccag ggtcctgtgc ctggatgggg gtgcaggcag ccttgaccac ggctgttccc    2280
ctcacccaaa agaattatca tcccaacagc caagacccaa caggtgctga actgtgcatc   2340
```

```
aaccaggaag agttctatcc ccaagctggc cactatcaca tatgcttact cttgcttaaa    2400
attaataaat catgttttga tgagaraaa                                      2429

<210> SEQ ID NO 2
<211> LENGTH: 486
<212> TYPE: DNA
<213> ORGANISM: human
<220> FEATURE:
<221> NAME/KEY: misc_feature
<222> LOCATION: (1)...(486)
<223> OTHER INFORMATION: n = A,T,C or G

<400> SEQUENCE: 2
tgtggwtggt ctcctagcat gttaatagat ataactcaca taaaaaatta ttgaggtctt      60
caataatttt tttttttraaa cagggaactc tctctgttgc ccaggctgga ttgcattggc    120
acaatcacgg ctcactggag gcctcaattg cctgggctca attaattccc tcatcttacc    180
ctcccaatta cctgggacca caaacttttg ccaccaggct gggttattat ttttaaatac    240
aaggtctcgt tattttggcc aaactggtct caaatyccctg gctcaacca atcccyctccc   300 catttcctcc caaatttctg ggattacagg cttaagctac cacacctggc cagccctcaa    360
taatttttaa aattaaaaaa attctcctaa acccaaaaat tttaaggacc tktaaggtac    420
aaaaaaacta tthtyaaaaa aatttcttac tcccycmmmm aaaaaaaaaa ccccntttt    480 tttttt                                                              486

<210> SEQ ID NO 3
<211> LENGTH: 397
<212> TYPE: DNA
<213> ORGANISM: human
<220> FEATURE:
<221> NAME/KEY: misc_feature
<222> LOCATION: (1)...(397)
<223> OTHER INFORMATION: n = A,T,C or G

<400> SEQUENCE: 3
tggtatctga canaataasr atgcamccat ttktganggg gtawtattta tctcagggat     60
ttactgtaaa tatgtataca cacatacaaa aacccaggca ttgttaagag aaaataatgg    120
cccaraggtt gaaattatca gacagaacct ttaaaaataa ttatgattaa tgtgttaaaa    180
ttctagtgga aaagataaat aacatgctca ggaaatttta gcagagagat agaaactatg    240
tgggaagctc aaatgaaaat gctaggaaat gaaaagcagt attggaggtg aaagattcct    300
ttggcaattt atcaacanac tggagatggc anaggcataa tcagtantat tgaaggcaga    360
ttactatnta ttatncaanc aaaaaaaaaa accccct                             397

<210> SEQ ID NO 4
<211> LENGTH: 376
<212> TYPE: DNA
<213> ORGANISM: human

<400> SEQUENCE: 4
gtttctactt gaaagtactg atcaaatgta gcattaccag gtatggacaa cttgatatta     60
tgggctatat tactcatcta ggactgccat aacaaaacac cacagactag gagccttaaa    120
caacagaaac ttatttttctc acggttctga aggggtggaa gtccaagatc gtggtgtcaa    180
caggcttggt ttcccccgag gcctcacccc ttggcttgca gacaacagcc ttttatagc    240 atcctcctac ggcctttcct ctgcgcatga gcactcccag tgtctgtctc tctcacctgt    300
```

```
tgtaagaaca ccaatcttat tggatgctat aggcctccac ccttatgacg tcattaaact    360
ttaaatgccg gtttaa                                                    376

<210> SEQ ID NO 5
<211> LENGTH: 380
<212> TYPE: DNA
<213> ORGANISM: human

<400> SEQUENCE: 5
tttygtttaa gatagcaagg cactagaact ggaaaagaca cagaaaaaca aagaatccaa     60 cccctttcatc ttacaggtga acaaactgt gatgatgcac atgtatgtgt tttgtaagct    120
gtgagcaccg taacaaaatg taaatttgcc attattagga agtgctggtg gcagtgaaga    180
agcacccagg ccacttgact cccagtctgg tgccctgtct acaccagaca acacaggagc    240
tgggtcagat tcccctcagc tgcttaacaa agttcctcga acagaaaagt gcttacaaag    300
ctgccttctc ggatactgga aaggtcgagt tttctgaact gcactgattt tattgcagtt    360
gaaaaaaaaa aaacccttwt                                                380

<210> SEQ ID NO 6
<211> LENGTH: 2730
<212> TYPE: DNA
<213> ORGANISM: human

<400> SEQUENCE: 6
cttgattacg ccaagctcga aattaaccct cactaaaggg aacaaaagct ggagctcgcg     60
cgcctgcagg tcgacactag tggatccaaa gaattcggca cgagacgtga ggggccccaa    120
cgtggaagcc ggctgtctga atccccacat cgtcctcaac attgacctgg cccccaccat    180
cctggacatt gcaggcctgg acatacctgc ggatatggac gggaaatcca tcctcaagct    240
gctggacacg gagcggccgg tgaatcggtt tcacttgaaa aagaagatga gggtctggcg    300
ggactccttc ttggtggaga gaggcaagct gctacacaag agagacaatg acaaggtgga    360
cgcccaggag gagaactttc gcccaagtac cagcgtgtga aggacctgtg tcagcgtgct    420
gagtaccaga cggcgtgtga gcagctggga cagaagtggc agtgtgtgga ggacgccacg    480
gggaagctga agctgcataa gtgcaagggc cccatgcggc tgggcggcag cagagccctc    540
tccaacctcg tgcccaagta atacgggcag ggcagcgagg cctgcacctg tgacagcggg    600
gagtacaagc tcagcctggc cggacgccgg aaaaaactct tcaagaagaa gtacaaggcc    660
agctatgtcc gcagtcgctc catccgctca gtggccatcg aggtggacgg cagggtgtac    720
cacgtaggcc tggtgatgc cgcccagccc cgaaacctca ccaagcggca ctggccaggg    780 gccccctgagg accaagatga caaggatggt ggggacttca gtggcactgg aggccttccc    840
gactactcag ccgccaaccc cattaaagtg acacatcgca ggtgctacat cctagagaac    900
gacacagtcc agtgtgacct ggacctgtac aagtccctgc aggcctggaa agaccacaag    960
ctgcacatcg accacgagat tgaaaccctg cagaacaaaa ttaagaacct gagggaagtc   1020
cgaggtcacc tgaagaaaaa gcggccagaa gaatgtgact gtcacaaaat cagctaccac   1080
acccagcaca aaggccgcct caagcacaga ggctccagtc tgcatccttt caggaagggc   1140
ctgcaagaga aggacaaggt gtggctgttg cgggagcaga gcgcaagaa gaaactccgc   1200 aagctgctca agcgcctgca gaacaacgac acgtgcagca tgccaggcct cacgtgcttc   1260
acccacgaca accagcactg gcagacgcg ccttttctgga cactgggcc tttctgtgcc   1320 tgcaccagcg ccaacaataa cacgtactgg tgcatgagga ccatcaatga gactcacaat   1380
```

```
ttcctcttct gtgaatttgc aactggcttc ctagagtact tgatctcaa cacagacccc    1440 taccagctga tgaatgcagt gaacacactg gacagggatg tcctcaacca gctacacgta    1500
cagctcatgg agctgaggag ctgcaagggt tacaagcagt gtaaccccg gactcgaaac    1560 atggacctgg gacttaaaga tggaggaagc tatgagcaat acaggcagtt tcagcgtcga    1620
aagtggccag aaatgaagag accttcttcc aaatcactgg gacaactgtg ggaaggctgg    1680
gaaggttaag aaacaacaga ggtggacctc caaaaacata gaggcatcac ctgactgcac    1740
aggcaatgaa aaccatgtg ggtgatttcc agcagacctg tggtattggc caggaggcct     1800
gagaaagcaa gcacgcactc tcagtcaaca tgacagattc tggaggataa ccagcaggag    1860
cagagataac ttcaggaagt ccattttgc ccctgctttt gctttggatt atacctcacc     1920
agctgcacaa aatgcatttt ttcgtatcaa aaagtcacca ctaaccctcc cccagaagct    1980
cacaaaggaa aacggagaga gcgagcgaga gagatttcct tggaaatttc tcccaagggc    2040
gaaagtcatt ggaattttta atcataggg aaaagcagtc ctgttctaaa tcctcttatt     2100
cttttggttt gtcacaaaga aggaactaag aagcaggaca gaggcaacgt ggagaggctg    2160
aaaacagtgc agagacgttt gacaatgagt cagtagcaca aaagagatga catttaccta    2220
gcactataaa ccctggttgc ctctgaagaa actgccttca ttgtatatat gtgactattt    2280
acatgtaatc aacatgggaa cttttagggg aacctaataa gaaatcccaa ttttcaggag    2340
tggtggtgtc aataaacgct ctgtggccag tgtaaaagaa aatccctcgc agttgtggac    2400
atttctgttc ctgtccagat accatttctc ctagtatttc tttgttatgt cccagaactg    2460
atgttttttt tttaaggtac tgaaaagaaa tgaagttgat gtatgtccca agttttgatg    2520
aaactgtatt agtaaaaaaa attttgtagt ttaagtattg tcatacagtg ttcaaaaccc    2580
cagccaatga ccagcagttg gtatgaagaa cctttgacat tttgtaaaag gccatttctt    2640
ggggaaaaaa aaaaaaaaaa aaaaaaaaaa aactcgagag tacttctaga gcggccgcgg    2700
gcccatcgat tttccacccg ggtggggtat                                     2730

<210> SEQ ID NO 7
<211> LENGTH: 218
<212> TYPE: DNA
<213> ORGANISM: human
<220> FEATURE:
<221> NAME/KEY: misc_feature
<222> LOCATION: (1)...(218)
<223> OTHER INFORMATION: n = A,T,C or G

<400> SEQUENCE: 7
ttntccatga ctcggggtcn cnnatggcat caaacaggan gnngnggctt catngtaaan     60
naccgtnatn tctnctncgg tccggtgtcc atnttggccn tcngacatcc tggtangacg    120
ccgagacaat ataaatgtac aatggatacc cgatgcaaac aatgtattgt ggttaactag    180
gtgtnatccc ncccattgtg ntantaaggg cngntgtc                            218

<210> SEQ ID NO 8
<211> LENGTH: 426
<212> TYPE: DNA
<213> ORGANISM: human
<220> FEATURE:
<221> NAME/KEY: misc_feature
<222> LOCATION: (1)...(426)
<223> OTHER INFORMATION: n = A,T,C or G

<400> SEQUENCE: 8
```

-continued

| | |
|---|---|
| gtyyatgatc acatctgacg ctattcctat cccottcctc cccgggacct tttcccottc | 60 |
| ctccctggga cctttccccc ttcctgttta anaagccagg gctgcctgga ggaagctttg | 120 |
| tcagatctag tggaatgtga cctccctgga atatgtgccc aggggtttgt ctaagcagtt | 180 |
| tcaggctatg gcctttactc catctggtcc ccatccctct tatctctctc atgtgtggct | 240 |
| gcacctggac gcttggacca tagctgtcac agcccctgg ggaggaaccc actccttggc | 300 |
| catgtcagcc tgtgcaatgc aaggctcttg tttgatctgt gtgctgacan aaagcccagc | 360 |
| ttccttaaga acttttcatg tggaacactt tggttttgag aagaaaataa atcanaaacc | 420 |
| attaaa | 426 |

<210> SEQ ID NO 9
<211> LENGTH: 480
<212> TYPE: DNA
<213> ORGANISM: human
<220> FEATURE:
<221> NAME/KEY: misc_feature
<222> LOCATION: (1)...(480)
<223> OTHER INFORMATION: n = A,T,C or G

<400> SEQUENCE: 9

| | |
|---|---|
| ctctacccctt tcctgatcca tgatcggggt cgcctttgga gcananagga ggcnatggcc | 60 |
| acatgganaa cnaggtgatc tgcncccctgg tcctggtgtc cangctggcc ctcggcnccc | 120 |
| tgggcnaagc nccnactnag acntntanna nnnccccccg gantanacnt aatgntagnt | 180 |
| ctnctnntnt cccncccctcc ccntnttctn nttaaggctg cnnttttccnc tacaccnncc | 240 |
| ntgnggtcnc nngnnncttc cntcctagtg tnttctantt ccttcccnat gacgattgtc | 300 |
| aattacagac accccccntca cgcangtggg agggacgaac nccggtgcct ccgtcactct | 360 |
| ggggggcnatt nncataccnt ggaatttaac cccnttctna ctgttcttnt ttgaatnnat | 420 |
| tgttntgtnc agtntttgtt caatattgat aagctacgta tttanaaaat atcatgctgt | 480 |

<210> SEQ ID NO 10
<211> LENGTH: 402
<212> TYPE: DNA
<213> ORGANISM: human
<220> FEATURE:
<221> NAME/KEY: misc_feature
<222> LOCATION: (1)...(402)
<223> OTHER INFORMATION: n = A,T,C or G

<400> SEQUENCE: 10

| | |
|---|---|
| tcgatacagg gaattaacaa atatatgaag tgtttcatga tcctccatca gttttttaaat | 60 |
| atgtctaatt aactcattta cctagaaaaa tataattgtc gatgagtttt taatgtgagg | 120 |
| agaasagctc ggctctcggc atctgtccac gtgcaggac cacttgggag tgatcatttc | 180 |
| aagcaggggt cttggagagc caggctgagg ccaggtcatt tgggctgtt tgcaatccta | 240 |
| actgggtcag ggcgaggcag gccagtgaag ggattaaaac tcttcaccct ctctaggccc | 300 |
| gtgttctgcc tccycwttag cactcatctg tmrcttggtt tagtccctgg tcanccaagg | 360 |
| ggggaattcc tggcccctgt caaaattctc aggaggctcc aa | 402 |

<210> SEQ ID NO 11
<211> LENGTH: 575
<212> TYPE: DNA
<213> ORGANISM: human
<220> FEATURE:
<221> NAME/KEY: misc_feature
<222> LOCATION: (1)...(575)
<223> OTHER INFORMATION: n = A,T,C or G

<400> SEQUENCE: 11

```
ttgcacagga gcatggnaga atgatgaact tccgtcagcg gatgggatgg attggagtgg      60
gattgtatct gttagccagt gcagcagcat tttactatgt ttttgaaatc agtgagactt     120
acaacaggct ggccttggaa cacattcaac agcaccctga ggagcccctt gaaggaacca    180
catggacaca ctccttgaaa gctcaattac tctccttgcc tttttgggtg tggacagtta    240
tttttctggt accttactta cagatgtttt tgttcctata ctcttgtaca agagctgatc    300
ccaaaacagt gggctactgt atcatcccta tgcttggc agttatttgc aatcgccacc       360
aggcatttgt caaggcttct aatcagatca gcagactaca actgattgac acgtnaaatc    420
agtcaccgtt ttttccctac nattacaaaa ctgccagtcc tatatggagt ctgatcacaa    480
gactgcagtt tcttcacaga tctcaggaag ttgtcgtggg gcanaagctt tttaaaaaca    540
tgtgattagg gagctatctt tatctgaata ataac                                575
```

<210> SEQ ID NO 12
<211> LENGTH: 442
<212> TYPE: DNA
<213> ORGANISM: human

<400> SEQUENCE: 12

```
gtatattkgc agtcagaggc accaaaaatg cacaccttgc aggttcctga aaaccactca     60
gtagccttaa accaaactac aaatggccat actgaatcaa ataactatat atataaaacc   120
ttgggtgtaa ataagcagac agaaaatcta aagaatcaac agactgagaa tctacttaaa   180
aggcgaagtt tcccgttatt tgacaactca aaagccaact tagatcctgg aaatagtaag   240
cattatgtat atagtacact taccaggaat cgagttagac aaccagaaaa gcccawagca   300
akatttgctg aaawgttcta aaagcatgcr caatgtgact cataacttgg aggaggatga   360
ggaggaagtt accaagaaga aactctccaa gtggcactac taccaaatca gtttccattg   420
ctgctttact tgatgtgaat aa                                              442
```

<210> SEQ ID NO 13
<211> LENGTH: 332
<212> TYPE: DNA
<213> ORGANISM: human
<220> FEATURE:
<221> NAME/KEY: misc_feature
<222> LOCATION: (1)...(332)
<223> OTHER INFORMATION: n = A,T,C or G

<400> SEQUENCE: 13

```
ccaagttaca agttttttc tagtgcttat gtacgtttta agcccatgc ctacctgtgg       60
gagtgcacct acaagccgga gtgtttcatt caatctatat ctaatcttta actagagtct   120
ggagtctgga aggttttctc tagagtcttg gaaagtttct taagtgggcc ctggtacaag   180
gtatacgtgt aagaatgcct ttattattca atcagacatt agggtctaag aaaacccagg   240
tggggtcata atgggtttgt tttcgtattc canccgttgt actcaggcac cagtttcccc   300
agttctttaa tgtttaactt ctacatacat ca                                   332
```

<210> SEQ ID NO 14
<211> LENGTH: 970
<212> TYPE: DNA
<213> ORGANISM: human
<220> FEATURE:
<221> NAME/KEY: misc_feature
<222> LOCATION: (1)...(970)
```

<223> OTHER INFORMATION: n = A,T,C or G

<400> SEQUENCE: 14

| | | | | | | |
|---|---|---|---|---|---|---|
| aaaagctgga | gctcgcgcgc | ctgcaggtcg | acactagtgg | atccaaagaa | ttcggcacga | 60 |
| gaggcaccaa | tgaagacatg | gtgtttcgtg | gaaacattga | taacaacact | ccatatgcta | 120 |
| actctttcac | acccccata | aaagctcagt | atgtaagact | ctatccccaa | gtttgtcgaa | 180 |
| gacattgcac | tttgcgaatg | gaacttcttg | gctgtgaact | gtcgggttgt | tctgagcctc | 240 |
| tgggtatgaa | atcaggacat | atacaagact | atcagatcac | tgcctccagc | atcttcagaa | 300 |
| cgctcaacat | ggacatgttc | acttgggaac | caaggaaaag | ctcggctgga | caagcaaggc | 360 |
| aaagtgaatg | cctggacctc | tggccacaat | gaccagtcac | aatggttaca | ggtggatctt | 420 |
| cttgttccaa | ccaaatgact | ggcatcatta | cacaaggagc | taaagatttt | ggtcatgtac | 480 |
| agtttgttgg | ctcctacaaa | ctggcttaca | gcaatgatgg | agaacactgg | actgtatacc | 540 |
| aggatgaaaa | gcaagaaaaa | gataaggttt | tccaggaaaa | ttttgacaat | gacactcaca | 600 |
| gaaaaaatgt | catcgaccct | ccatctatg | cacgacacat | aagaatcctt | ccttggtcct | 660 |
| ggtacgggag | gatcacattg | cggtcagagc | tgctgggctg | cacagaggag | gaatgagggg | 720 |
| aggctacatt | tcacaaccct | cttccctatt | tccctaaaag | tatctccatg | gaatgaactg | 780 |
| tgcaaaatct | gtaggaaact | gaatggtttt | ntttttttt | tcatgaaaaa | gtgctcaaat | 840 |
| tatggtaggc | aactaacggt | gttttaagg | gggtctaagc | ctgcctttc | aatgatttaa | 900 |
| ttggatttta | ttttatccgc | aaatctctta | agtaacaaca | cattaagtgt | gaattacttt | 960 |
| tctctcattg | | | | | | 970 |

<210> SEQ ID NO 15
<211> LENGTH: 528
<212> TYPE: DNA
<213> ORGANISM: human
<220> FEATURE:
<221> NAME/KEY: misc_feature
<222> LOCATION: (1)...(528)
<223> OTHER INFORMATION: n = A,T,C or G

<400> SEQUENCE: 15

| | | | | | | |
|---|---|---|---|---|---|---|
| ttctacccctt | tcctgagcca | catgtttcac | acaagtgtag | aaaatgccag | ggatccacca | 60 |
| caagatggag | atggtcagca | caaaccgatt | ctgttcctct | ttaaagtgta | tattagccac | 120 |
| ttagcaatct | ctatattctt | tcaagtaacc | aagctgttga | cttcttact | acttgcagta | 180 |
| gcctgtcccc | aacttttcca | tccagtgctt | aacctaaaaa | actccttaac | tctgccttga | 240 |
| cctgaggaan | accatgctaa | ctggtgttat | tttgtatgta | ccctgtgctt | aattctataa | 300 |
| cagtaaaccc | catacgcagg | tgggagggag | gaacaccggt | gcctcggtca | ctctgggggc | 360 |
| agtttagatg | ctgtgaaatt | aaacctgttc | taagtgtact | tgtttgaatt | aattgtattg | 420 |
| taatattatt | tgttgaatgt | agtaattagg | tatttatgaa | tatattgctg | taatttctga | 480 |
| caacatccaa | aaaataaaat | cttcctaaat | taaaaaaaaa | aaacccaa | | 528 |

<210> SEQ ID NO 16
<211> LENGTH: 3831
<212> TYPE: DNA
<213> ORGANISM: human

<400> SEQUENCE: 16

| | | | | | | |
|---|---|---|---|---|---|---|
| ggcacgagct | gggctcctgc | agagcagatc | ctgtctgcgt | cctccaggag | gagtgggtgg | 60 |
| caggactggg | gtttcccaca | ggttttgggg | cggcggcgag | attggcacgg | tccggggtcg | 120 |

-continued

```
caggcgcgca gccacgcccc tggaagtccg ccccggcccc cgcccccaac ccgcctcttc      180
ggggctttat ggcgtgaggt ttggggctgg gatccatctg gagccgagca gaaaactttt      240
cccctcccgt tccggtccc ttttgtcttt cttggacgcg gtggcggcgc cgcctgagcg       300
gcgactccct ctccctgcc cggcttgctg cgcccggtgc cctccgaggg caggcgcgcc       360
tggactctgc gcccggatgg cggcggccct ctgtgagcac cggcagcggc gcatcccctg      420
ccccgaggcc tccggtgccc ccccggcgcg ggcatagggg cgcccccacc ctccgtccgc      480
ttgcacccct tgctccccgc ccctcgcct gactcatccg cccgcggtgg ccgcccgagc       540
cctgggatgg ggagggagac cgcggctgcc cgcggcggcc gagattcccg ctgacgcccc      600
cgaccctgcc gccttcttcg tccgcctcca gaggcgcccg acgtcccgac agctcctgga      660
gtgagaccag gactgagaac agggagaggc gacccgaccc ccagggcccg gtgctcatga      720
cagcacacag agccgctgaa aacgactgaa gagagcaatg gatttcctgt gacatctggc      780
tctggagagt aaaatgccaa gctatgatag caactggtgg agtgataact ggcctggccg      840
ccttgaaaag gcaagactct gccagatcac agcagcatgt caacctcagc ccgtctcctg      900
ctacccaaga gaagaagccc atccaggcgc ccggcccccg ggcagatgtc gtggttgttc      960
gtggcaaaat ccggctttat tccccatctg gttttttct tattttagga gtgctcatct      1020
ccattatagg aattgctatg gccgttcttg gatattggcc ccaaaagaa cattttattg       1080 atgctgaaac aacactgtca acaaatgaaa ctcaggtcat tcggaatgaa ggcggtgtgg      1140
tggttcgctt ctttgagcag catttgcatt ctgataagat gaaaatgctt ggcccattca      1200
ccatggggat tggcatttc attttcattt gtgctaatgc cattcttcat gaaaaccgtg       1260
acaaagagac caaaatcata cacatgaggg atatctattc cacagtcatt gacattcaca      1320
cgctaagaat caaggagcaa aggcaaatga acggcatgta cactggtttg atgggagaaa      1380
cagaagtaaa acagaatggg agctcctgtg cctcgagatt ggcagcaaat acgatcgcct      1440
ctttctcggg ttttcggagc agttttcgaa tggacagctc cgtggaggag gatgaactta      1500
tgttaaatga aggtaagagt tctgggcatc ttatgccccc tttgctctct gacagctctg      1560
tgtctgtctt tggcctctat ccacctcctt ccaagacaac tgatgataag accagcggct      1620
ctaagaaatg tgaaaccaag tcaattgtgt catcgtccat cagtgctttt acattgcctg      1680
tgatcaaact taataactgt gttattgatg agcccagtat agataacatc actgaagatg      1740
ctgacaacct caaaagtagg tcaaggaatt tgtcaatgga ttcccttgtg gttccttgc      1800 ccaacaccag tgaatccttc cagcccgtca gcacagtgct accaaggaat aattccattg      1860
gggagtcgtt gtcgagtcag tacaagtcat ctatggctct cggacctggg gctggagagc      1920
tcttgtctcc tggggctgcc agaagacagt ttgggtccaa tacatccttg catttgctct      1980
cgtcacactc aaagtccttg gacttagacc ggggtccctc cactctaact gttcaggcag      2040
aacaacggaa acatccaagt tggcctaggt tggatcggaa caacagcaag ggatatatga      2100
aactagagaa caaagaagac ccgatggata ggttgcttgt gccccaagtt gccatcaaaa      2160
aggactttac caataaggag aagcttctta tgatttcaag atctcacaat aatttgagtt      2220
ttgaacatga tgagtttttg agtaacaacc taaagagggg aacttctgaa acaaggtttt      2280
aatgttaaaa gaatatatca ttttacaagg gtatatattt taaaacgatt ttcactggtg      2340
tttccttctt aaagtattgg ctgtaacgtt tttaatcaaa tggtttgtag tgtattagaa      2400
ttggctgctt agttctgtaa tgaagatggt tgtatgtttg ggtacttgt gactgcagta      2460
```

| | | | | | |
|---|---|---|---|---|---|
| ctctatgtta | ccacacatga | ttttattttt | ctcttccttt | gaaagcatga | tctcttttat | 2520 |
| taatatgaat | gcaaaatgct | tgcatccaaa | ttaaagctta | ttttctttac | ttttaagttc | 2580 |
| tttgattgcc | ctattcataa | aatgaaatgt | ccagtatgga | aaacataggg | taccaaagtg | 2640 |
| tggaccagga | gtacaaattc | agtcccaata | ctcaatacgt | attatagatg | actatgagtg | 2700 |
| caaaccttag | gatgtgattt | tctgaataat | tgttctttgt | aggatttggt | tacattattt | 2760 |
| aaaatgaaaa | agatctagtt | ttagtgtgag | ctcagtaatg | ttaattggtt | aagttcattg | 2820 |
| tgaatcttga | gttttagata | agtagttatt | tttttcaata | tcacttctgt | ttttagtgat | 2880 |
| attatatcaa | gaaacaacgt | attcaagagc | catggctgac | agtgccagat | atacttaggg | 2940 |
| ataaacatca | aaatgcaatt | atagttgcta | taacgttaga | tactcggaat | caaaatttat | 3000 |
| ttgcaagctg | acttgataaa | ctaaatgaac | caataaaatt | tgtagaaatg | gctatcctga | 3060 |
| aataattata | tacatgaaga | caatgttgac | taatgaatta | agatacatta | tatactagtt | 3120 |
| aatgctaact | agtctcagta | cctgttttta | gccatctgtt | actgtccaat | agcacctcat | 3180 |
| tcccacattc | tattttcccc | cggtattctt | tagatcctag | tatttggaaa | acaatcggct | 3240 |
| aaccttgaca | tttctttta | ccttcatatg | ccactatctc | ggtagttcaa | aaaaatttag | 3300 |
| ttcttgataa | attgccttga | agtttacctt | gtgctggaga | gccttatgat | aactccaaag | 3360 |
| actttcttac | ggtataatac | atgttgttta | ggattgtgtt | tcttagtcac | tgaagataat | 3420 |
| aaatattaaa | atggatgttt | tcatcagaaa | attttcatgt | tttcctttaa | ggtaacataa | 3480 |
| ttgtaagaat | tgtttaataa | aatactcagg | aaattctaaa | ggtttctccc | aatacctaaa | 3540 |
| catttctgaa | catcagtatt | gcagttgtgg | aagagcagaa | ggaggataca | tttgtttgtg | 3600 |
| ttgctcccca | aaattccacc | ttgcatttgc | atcacaaact | tccctcaatt | gaggcagttt | 3660 |
| tctttgttag | aacattaagt | ctgtgtattg | taatagagtg | ggctcaatat | tttactataa | 3720 |
| agcatttaat | aaactgttac | caatagaagt | ttgtgttctt | cacacctttg | ctattgctttt | 3780 |
| ttaaataaaa | tgtacatttc | tgcttaaaaa | aaaaaaaaaa | aaaaaaaaaa | g | 3831 |

```
<210> SEQ ID NO 17
<211> LENGTH: 1718
<212> TYPE: DNA
<213> ORGANISM: human

<400> SEQUENCE: 17
```

| | | | | | |
|---|---|---|---|---|---|
| aatgaaagag | cttcttaccc | agtgctgttg | ccctttgag | tatttttgtt | tttaaaataa | 60 |
| tgattgtaaa | atgttttaca | agtaatgtaa | aagctagtat | cattcttaca | tacttctgtg | 120 |
| tttaaatttt | cattcttacc | aaaacagtta | actctttctt | tccaatcaat | ttatacaaaa | 180 |
| gaggtcgctc | cagccctacc | acaggtctga | ctggcactgc | cttttgtttg | cccttgaaca | 240 |
| gggcagtgtt | gtgggactg | caaaagagaa | aacgtccagg | cgagcccagt | tgtcctcgcc | 300 |
| cacagggtcc | tgcaggctcc | atcagtcacc | gctttctatg | gcgtttgtag | ttgtgtcttt | 360 |
| taagaagtga | gtgtgattgt | ttacttgata | aatcagctca | ctctctggtg | cttttttagag | 420 |
| aagtcccctga | ttccttctta | aacttggaat | gatagatgaa | attcacaccc | ctgcagatca | 480 |
| gaaaaacaaa | tagaagaaaa | tgagggttac | agtaacctgt | tgtctttata | taacttgcaa | 540 |
| caaactaatt | tatttttttt | tccttttttt | gttttggtt | tttatggtt | ttttaaggaa | 600 |
| aatactttc | tcctttgaag | ttttacagct | ttttgtaaat | gcgtcctgat | aatgattagg | 660 |
| aaaatcgacc | ttttcatcca | tgatgaccat | cctcatagct | cagatttcct | ttcaaagtag | 720 |
| tggctttctg | gatggtaatt | ccatcttaag | gtgtcagaac | tattttcaaa | tgctgccttt | 780 |

-continued

```
gacagttctt ggaatttttct gatattaagc agttccatgc aaatattcgt gtttttataaa    840
tagctctcat agtctgctcc atcttgatag ttaagtgatt tctgaagcgt tgtgtgtgt       900
gttgatcagg ttgtgtgata ttttgcttg ataaagaatc aaatttgaaa caattaacca       960
gccagtagat tgtctgtcag tgaccttctg tagtaataaa gttttttgcca ctgtaaataa    1020
aaacagtatc cgtagctatc aggatcattg cgcactcata tatgctaagc cttctgttct    1080
ctaatagaag cctttctttt ccattgtttc tggatatttg tattatccaa atgtgcttat    1140
ttctttgcct tagcacacgt tttatggagt acttgttata ctaggtttga tttgaaactg    1200
gtgcttgtcg cagaactgtc agagcatgag gagcgctcct cctgtgggtg gacgcattca    1260
cgcactcccc aggttgcacc tgctgctggc ggtgagcagg gggttcagca gcttgaccga    1320
tgcccccga gggggctctc cccagcttaa actttgttgt ttaaatttgt taacttttta    1380
tattaatgac tattgaaagt ggtaataaaa atttatatta taggcttcaa tgttttcatg    1440
aatgttaccc aaaaagctgt gttttctttg gtcagaggtc aaaatttatg aaaaacaaaa    1500
tgctgtatga atggaaatca ttttgcaatt gagtgacact tcattgtaat tcacagtgta    1560
aatttaatcc aaactgaaat tttgtttcaa ctgaatttgt aattaactct gaatttgttt    1620
ttaatcatta gtaatatttc agttgggtat ctttttaagt aaaacaaca aataaactct    1680
gtacatgtaa aacgtgaaaa aaaaaaaaaa aaaaaaaa                            1718
```

<210> SEQ ID NO 18
<211> LENGTH: 1873
<212> TYPE: DNA
<213> ORGANISM: human

<400> SEQUENCE: 18

```
aggcacgagg ccccgcgcgc cggccgagtc gctgagccgc ggctgccgga cgggacgggga      60
ccggctaggc tgggcgcgcc ccccgggccc cgccgtgggc atgggcgcac tggccccggc     120
gctgctgctg cctctgctgg cccagtggct cctgcgcgcc gccccggagc tggccccgc      180
gcccttcacg ctgcccctcc gggtggccgc ggccacgaac cgcgtagttg cgcccacccc     240
gggacccggg accctgccg agcgccacgc cgacggcttg gcgctcgccc tggagcctgc      300
cctggcgtcc cccgcgggcg ccgccaactt cttggccatg gtagacaacc tgcaggggga     360
ctctggccgc ggctactacc tggagatgct gatcgggacc cccccgcaga agctacagat     420
tctcgttgac actggaagca gtaactttgc cgtggcagga accccgcact cctacataga     480
cacgtacttt gacacagaga ggtctagcac ataccgctcc aagggctttg acgtcacagt     540
gaagtacaca caaggaagct ggacgggctt cgttggggaa gacctcgtca ccatccccaa     600
aggcttcaat acttcttttc ttgtcaacat tgccactatt tttgaatcag agaatttctt     660
tttgcctggg attaaatgga atggaatact tggcctagct tatgccacac ttgccaagcc     720
atcaagttct ctggagacct tcttcgactc cctggtgaca caagcaaaca tccccaacgt     780
tttctccatg cagatgtgtg gagccggctt gcccgttgct ggatctggga ccaacggagg     840
tagtcttgtc ttgggtggaa ttgaaccaag tttgtataaa ggagacatct ggtatacccc     900
tattaaggaa gagtggtact accagataga aattctgaaa ttggaaattg gaggccaaag     960
ccttaatctg gactgcagag agtataacgc agacaaggcc atcgtggaca gtggcaccac    1020
gctgctgcgc ctgccccaga aggtgttga tgccggtggtg gaagctgtgg cccgcgcatc    1080
tctgattcca gaattctctg atggttttcg gactgggtcc cagctggcgt gctggacgaa    1140
```

-continued

| | |
|---|---|
| ttcggaaaca ccttggtctt acttccctaa aatctccatc tacctgagag atgagaactc | 1200 |
| cagcaggtca ttccgtatca caatcctgcc tcagctttac attcagccca tgatggggc | 1260 |
| cggcctgaat tatgaatgtt accgattcgg catttcccca tccacaaatg cgctggtgat | 1320 |
| cggtgccacg gtgatggagg gcttctacgt catcttcgac agagcccaga gagggtggg | 1380 |
| cttcgcagcg agcccctgtg cagaaattgc aggtgctgca gtgtctgaaa tttccgggcc | 1440 |
| tttctcaaca gaggatgtag ccagcaactg tgtccccgct cagtctttga gcgagcccat | 1500 |
| tttgtggatt gtgtcctatg cgctcatgag cgtctgtgga gccatcctcc ttgtcttaat | 1560 |
| cgtcctgctg ctgctgccgt tccggtgtca gcgtcgcccc cgtgaccctg aggtcgtcaa | 1620 |
| tgatgagtcc tctctggtca gacatcgctg gaatgaata gccaggcctg acctcaagca | 1680 |
| accatgaact cagctattaa gaaaatcaca tttccagggc agcagccggg atcgatggtg | 1740 |
| gcgctttctc ctgtgcccac ccgtcttcaa tctctgttct gctcccagat gccttctaga | 1800 |
| ttcactgtct tttgattctt gattttcaag ctttcaaatc ctccctactt ccaagaaaaa | 1860 |
| aaaaaaaaaa aaa | 1873 |

<210> SEQ ID NO 19
<211> LENGTH: 518
<212> TYPE: PRT
<213> ORGANISM: human

<400> SEQUENCE: 19

Met Gly Ala Leu Ala Arg Ala Leu Leu Leu Pro Leu Leu Ala Gln Trp
1               5                   10                  15

Leu Leu Arg Ala Ala Pro Glu Leu Ala Pro Ala Pro Phe Thr Leu Pro
            20                  25                  30

Leu Arg Val Ala Ala Ala Thr Asn Arg Val Val Ala Pro Thr Pro Gly
        35                  40                  45

Pro Gly Thr Pro Ala Glu Arg His Ala Asp Gly Leu Ala Leu Ala Leu
    50                  55                  60

Glu Pro Ala Leu Ala Ser Pro Ala Gly Ala Ala Asn Phe Leu Ala Met
65                  70                  75                  80

Val Asp Asn Leu Gln Gly Asp Ser Gly Arg Gly Tyr Tyr Leu Glu Met
                85                  90                  95

Leu Ile Gly Thr Pro Pro Gln Lys Leu Gln Ile Leu Val Asp Thr Gly
            100                 105                 110

Ser Ser Asn Phe Ala Val Ala Gly Thr Pro His Ser Tyr Ile Asp Thr
        115                 120                 125

Tyr Phe Asp Thr Glu Arg Ser Ser Thr Tyr Arg Ser Lys Gly Phe Asp
    130                 135                 140

Val Thr Val Lys Tyr Thr Gln Gly Ser Trp Thr Gly Phe Val Gly Glu
145                 150                 155                 160

Asp Leu Val Thr Ile Pro Lys Gly Phe Asn Thr Ser Phe Leu Val Asn
                165                 170                 175

Ile Ala Thr Ile Phe Glu Ser Glu Asn Phe Phe Leu Pro Gly Ile Lys
            180                 185                 190

Trp Asn Gly Ile Leu Gly Leu Ala Tyr Ala Thr Leu Ala Lys Pro Ser
        195                 200                 205

Ser Ser Leu Glu Thr Phe Phe Asp Ser Leu Val Thr Gln Ala Asn Ile
    210                 215                 220

Pro Asn Val Phe Ser Met Gln Met Cys Gly Ala Gly Leu Pro Val Ala
225                 230                 235                 240

```
Gly Ser Gly Thr Asn Gly Gly Ser Leu Val Leu Gly Gly Ile Glu Pro
                245                 250                 255

Ser Leu Tyr Lys Gly Asp Ile Trp Tyr Thr Pro Ile Lys Glu Glu Trp
            260                 265                 270

Tyr Tyr Gln Ile Glu Ile Leu Lys Leu Glu Ile Gly Gln Ser Leu
        275                 280                 285

Asn Leu Asp Cys Arg Glu Tyr Asn Ala Asp Lys Ala Ile Val Asp Ser
290                 295                 300

Gly Thr Thr Leu Leu Arg Leu Pro Gln Lys Val Phe Asp Ala Val Val
305                 310                 315                 320

Glu Ala Val Ala Arg Ala Ser Leu Ile Pro Glu Phe Ser Asp Gly Phe
                325                 330                 335

Trp Thr Gly Ser Gln Leu Ala Cys Trp Thr Asn Ser Glu Thr Pro Trp
            340                 345                 350

Ser Tyr Phe Pro Lys Ile Ser Ile Tyr Leu Arg Asp Glu Asn Ser Ser
        355                 360                 365

Arg Ser Phe Arg Ile Thr Ile Leu Pro Gln Leu Tyr Ile Gln Pro Met
370                 375                 380

Met Gly Ala Gly Leu Asn Tyr Glu Cys Tyr Arg Phe Gly Ile Ser Pro
385                 390                 395                 400

Ser Thr Asn Ala Leu Val Ile Gly Ala Thr Val Met Glu Gly Phe Tyr
                405                 410                 415

Val Ile Phe Asp Arg Ala Gln Lys Arg Val Gly Phe Ala Ala Ser Pro
            420                 425                 430

Cys Ala Glu Ile Ala Gly Ala Ala Val Ser Glu Ile Ser Gly Pro Phe
        435                 440                 445

Ser Thr Glu Asp Val Ala Ser Asn Cys Val Pro Ala Gln Ser Leu Ser
450                 455                 460

Glu Pro Ile Leu Trp Ile Val Ser Tyr Ala Leu Met Ser Val Cys Gly
465                 470                 475                 480

Ala Ile Leu Leu Val Leu Ile Val Leu Leu Leu Pro Phe Arg Cys
                485                 490                 495

Gln Arg Arg Pro Arg Asp Pro Glu Val Val Asn Asp Glu Ser Ser Leu
            500                 505                 510

Val Arg His Arg Trp Lys
        515

<210> SEQ ID NO 20
<211> LENGTH: 31
<212> TYPE: DNA
<213> ORGANISM: human

<400> SEQUENCE: 20
acgactcact ataggctttt tttttttta a                               31

<210> SEQ ID NO 21
<211> LENGTH: 26
<212> TYPE: DNA
<213> ORGANISM: human

<400> SEQUENCE: 21
acaatttcac acaggacgac tccaag                                    26

<210> SEQ ID NO 22
<211> LENGTH: 396
<212> TYPE: PRT
<213> ORGANISM: Homo sapien
```

<400> SEQUENCE: 22

```
Met Lys Thr Leu Leu Leu Leu Leu Val Leu Glu Leu Gly Glu
 1               5                  10                  15

Ala Gln Gly Ser Leu His Arg Val Pro Leu Arg Arg His Pro Ser Leu
            20                  25                  30

Lys Lys Lys Leu Arg Ala Arg Ser Gln Leu Ser Glu Phe Trp Lys Ser
        35                  40                  45

His Asn Leu Asp Met Ile Gln Phe Thr Glu Ser Cys Ser Met Asp Gln
 50                  55                  60

Ser Ala Lys Glu Pro Leu Ile Asn Tyr Leu Asp Met Glu Tyr Phe Gly
 65                  70                  75                  80

Thr Ile Ser Ile Gly Ser Pro Pro Gln Asn Phe Thr Val Ile Phe Asp
                85                  90                  95

Thr Gly Ser Ser Asn Leu Trp Val Pro Ser Val Tyr Cys Thr Ser Pro
            100                 105                 110

Ala Cys Lys Thr His Ser Arg Phe Gln Pro Ser Gln Ser Ser Thr Tyr
        115                 120                 125

Ser Gln Pro Gly Gln Ser Phe Ser Ile Gln Tyr Gly Thr Gly Ser Leu
    130                 135                 140

Ser Gly Ile Ile Gly Ala Asp Gln Val Ser Val Glu Gly Leu Thr Val
145                 150                 155                 160

Val Gly Gln Gln Phe Gly Glu Ser Val Thr Glu Pro Gly Gln Thr Phe
                165                 170                 175

Val Asp Ala Glu Phe Asp Gly Ile Leu Gly Leu Gly Tyr Pro Ser Leu
            180                 185                 190

Ala Val Gly Gly Val Thr Pro Val Phe Asp Asn Met Met Ala Gln Asn
        195                 200                 205

Leu Val Asp Leu Pro Met Phe Ser Val Tyr Met Ser Ser Asn Pro Glu
    210                 215                 220

Gly Gly Ala Gly Ser Glu Leu Ile Phe Gly Gly Tyr Asp His Ser His
225                 230                 235                 240

Phe Ser Gly Ser Leu Asn Trp Val Pro Val Thr Lys Gln Ala Tyr Trp
                245                 250                 255

Gln Ile Ala Leu Asp Asn Ile Gln Val Gly Gly Thr Val Met Phe Cys
            260                 265                 270

Ser Glu Gly Cys Gln Ala Ile Val Asp Thr Gly Thr Ser Leu Ile Thr
        275                 280                 285

Gly Pro Ser Asp Lys Ile Lys Gln Leu Gln Asn Ala Ile Gly Ala Ala
    290                 295                 300

Pro Val Asp Gly Glu Tyr Ala Val Glu Cys Ala Asn Leu Asn Val Met
305                 310                 315                 320

Pro Asp Val Thr Phe Thr Ile Asn Gly Val Pro Tyr Thr Leu Ser Pro
                325                 330                 335

Thr Ala Tyr Thr Leu Leu Asp Phe Val Asp Gly Met Gln Phe Cys Ser
            340                 345                 350

Ser Gly Phe Gln Gly Leu Asp Ile His Pro Pro Ala Gly Pro Leu Trp
        355                 360                 365

Ile Leu Gly Asp Val Phe Ile Arg Gln Phe Tyr Ser Val Phe Asp Arg
    370                 375                 380

Gly Asn Asn Arg Val Gly Leu Ala Pro Ala Val Pro
385                 390                 395
```

<210> SEQ ID NO 23
<211> LENGTH: 388
<212> TYPE: PRT
<213> ORGANISM: Homo sapien

<400> SEQUENCE: 23

```
Met Lys Trp Leu Leu Leu Gly Leu Val Ala Leu Ser Glu Cys Ile
1               5                   10                  15

Met Tyr Lys Val Pro Leu Ile Arg Lys Lys Ser Leu Arg Arg Thr Leu
            20                  25                  30

Ser Glu Arg Gly Leu Leu Lys Asp Phe Leu Lys Lys His Asn Leu Asn
        35                  40                  45

Pro Ala Arg Lys Tyr Phe Pro Gln Trp Glu Ala Pro Thr Leu Val Asp
    50                  55                  60

Glu Gln Pro Leu Glu Asn Tyr Leu Asp Met Glu Tyr Phe Gly Thr Ile
65                  70                  75                  80

Gly Ile Gly Thr Pro Ala Gln Asp Phe Thr Val Val Phe Asp Thr Gly
                85                  90                  95

Ser Ser Asn Leu Trp Val Pro Ser Val Tyr Cys Ser Ser Leu Ala Cys
            100                 105                 110

Thr Asn His Asn Arg Phe Asn Pro Glu Asp Ser Ser Thr Tyr Gln Ser
        115                 120                 125

Thr Ser Glu Thr Val Ser Ile Thr Tyr Gly Thr Gly Ser Met Thr Gly
    130                 135                 140

Ile Leu Gly Tyr Asp Thr Val Gln Val Gly Gly Ile Ser Asp Thr Asn
145                 150                 155                 160

Gln Ile Phe Gly Leu Ser Glu Thr Glu Pro Gly Ser Phe Leu Tyr Tyr
                165                 170                 175

Ala Pro Phe Asp Gly Ile Leu Gly Leu Ala Tyr Pro Ser Ile Ser Ser
            180                 185                 190

Ser Gly Ala Thr Pro Val Phe Asp Asn Ile Trp Asn Gln Gly Leu Val
        195                 200                 205

Ser Gln Asp Leu Phe Ser Val Tyr Leu Ser Ala Asp Asp Gln Ser Gly
    210                 215                 220

Ser Val Val Ile Phe Gly Gly Ile Asp Ser Ser Tyr Tyr Thr Gly Ser
225                 230                 235                 240

Leu Asn Trp Val Pro Val Thr Val Glu Gly Tyr Trp Gln Ile Thr Val
                245                 250                 255

Asp Ser Ile Thr Met Asn Gly Glu Ala Ile Ala Cys Ala Glu Gly Cys
            260                 265                 270

Gln Ala Ile Val Asp Thr Gly Thr Ser Leu Leu Thr Gly Pro Thr Ser
        275                 280                 285

Pro Ile Ala Asn Ile Gln Ser Asp Ile Gly Ala Ser Glu Asn Ser Asp
    290                 295                 300

Gly Asp Met Val Val Ser Cys Ser Ala Ile Ser Ser Leu Pro Asp Ile
305                 310                 315                 320

Val Phe Thr Ile Asn Gly Val Gln Tyr Pro Val Pro Ser Ala Tyr
                325                 330                 335

Ile Leu Gln Ser Glu Gly Ser Cys Ile Ser Gly Phe Gln Gly Met Asn
            340                 345                 350

Leu Pro Thr Glu Ser Gly Glu Leu Trp Ile Leu Gly Asp Val Phe Ile
        355                 360                 365

Arg Gln Tyr Phe Thr Val Phe Asp Arg Ala Asn Asn Gln Val Gly Leu
    370                 375                 380
```

```
Ala Pro Val Ala
385

<210> SEQ ID NO 24
<211> LENGTH: 388
<212> TYPE: PRT
<213> ORGANISM: Homo sapien

<400> SEQUENCE: 24

Met Lys Trp Met Val Val Leu Val Cys Leu Gln Leu Leu Glu Ala
 1               5                  10                  15

Ala Val Val Lys Val Pro Leu Lys Lys Phe Lys Ser Ile Arg Glu Thr
                20                  25                  30

Met Lys Glu Lys Gly Leu Leu Gly Glu Phe Leu Arg Thr His Lys Tyr
            35                  40                  45

Asp Pro Ala Trp Lys Tyr Arg Phe Gly Asp Leu Ser Val Thr Tyr Glu
        50                  55                  60

Pro Met Ala Tyr Met Asp Ala Ala Tyr Phe Gly Glu Ile Ser Ile Gly
65                  70                  75                  80

Thr Pro Pro Gln Asn Phe Leu Val Leu Phe Asp Thr Gly Ser Ser Asn
                85                  90                  95

Leu Trp Val Pro Ser Val Tyr Cys Gln Ser Gln Ala Cys Thr Ser His
                100                 105                 110

Ser Arg Phe Asn Pro Ser Glu Ser Ser Thr Tyr Ser Thr Asn Gly Gln
            115                 120                 125

Thr Phe Ser Leu Gln Tyr Gly Ser Gly Ser Leu Thr Gly Phe Phe Gly
        130                 135                 140

Tyr Asp Thr Leu Thr Val Gln Ser Ile Gln Val Pro Asn Gln Glu Phe
145                 150                 155                 160

Gly Leu Ser Glu Asn Glu Pro Gly Thr Asn Phe Val Tyr Ala Gln Phe
                165                 170                 175

Asp Gly Ile Met Gly Leu Ala Tyr Pro Ala Leu Ser Val Asp Glu Ala
            180                 185                 190

Thr Thr Ala Met Gln Gly Met Val Gln Glu Gly Ala Leu Thr Ser Pro
        195                 200                 205

Val Phe Ser Val Tyr Leu Ser Asn Gln Gln Gly Ser Ser Gly Gly Ala
210                 215                 220

Val Val Phe Gly Gly Val Asp Ser Ser Leu Tyr Thr Gly Gln Ile Tyr
225                 230                 235                 240

Trp Ala Pro Val Thr Gln Glu Leu Tyr Trp Gln Ile Gly Ile Glu Glu
                245                 250                 255

Phe Leu Ile Gly Gly Gln Ala Ser Gly Trp Cys Ser Glu Gly Cys Gln
            260                 265                 270

Ala Ile Val Asp Thr Gly Thr Ser Leu Leu Thr Val Pro Gln Gln Tyr
        275                 280                 285

Met Ser Ala Leu Leu Gln Ala Thr Gly Ala Gln Glu Asp Glu Tyr Gly
290                 295                 300

Gln Phe Leu Val Asn Cys Asn Ser Ile Gln Asn Leu Pro Ser Leu Thr
305                 310                 315                 320

Phe Ile Ile Asn Gly Val Glu Phe Pro Leu Pro Pro Ser Ser Tyr Ile
                325                 330                 335

Leu Ser Asn Asn Gly Tyr Cys Thr Val Gly Val Glu Pro Thr Tyr Leu
            340                 345                 350

Ser Ser Gln Asn Gly Gln Pro Leu Trp Ile Leu Gly Asp Val Phe Leu
        355                 360                 365
```

Arg Ser Tyr Tyr Ser Val Tyr Asp Leu Gly Asn Asn Arg Val Gly Phe
        370                 375                 380

Ala Thr Ala Ala
385

<210> SEQ ID NO 25
<211> LENGTH: 412
<212> TYPE: PRT
<213> ORGANISM: Homo sapien

<400> SEQUENCE: 25

Met Gln Pro Ser Ser Leu Leu Pro Leu Ala Leu Cys Leu Leu Ala
 1               5                   10                  15

Pro Ala Ser Ala Leu Val Arg Ile Pro Leu His Lys Phe Thr Ser Ile
                20                  25                  30

Arg Arg Thr Met Ser Glu Val Gly Gly Ser Val Glu Asp Leu Ile Ala
            35                  40                  45

Lys Gly Pro Val Ser Lys Tyr Ser Gln Ala Val Pro Ala Val Thr Glu
50                  55                  60

Gly Pro Ile Pro Glu Val Leu Lys Asn Tyr Met Asp Ala Gln Tyr Tyr
65                  70                  75                  80

Gly Glu Ile Gly Ile Gly Thr Pro Pro Gln Cys Phe Thr Val Val Phe
                85                  90                  95

Asp Thr Gly Ser Ser Asn Leu Trp Val Pro Ser Ile His Cys Lys Leu
            100                 105                 110

Leu Asp Ile Ala Cys Trp Ile His His Lys Tyr Asn Ser Asp Lys Ser
        115                 120                 125

Ser Thr Tyr Val Lys Asn Gly Thr Ser Phe Asp Ile His Tyr Gly Ser
    130                 135                 140

Gly Ser Leu Ser Gly Tyr Leu Ser Gln Asp Thr Val Ser Val Pro Cys
145                 150                 155                 160

Gln Ser Ala Ser Ser Ala Ser Ala Leu Gly Gly Val Lys Val Glu Arg
                165                 170                 175

Gln Val Phe Gly Glu Ala Thr Lys Gln Pro Gly Ile Thr Phe Ile Ala
            180                 185                 190

Ala Lys Phe Asp Gly Ile Leu Gly Met Ala Tyr Pro Arg Ile Ser Val
        195                 200                 205

Asn Asn Val Leu Pro Val Phe Asp Asn Leu Met Gln Gln Lys Leu Val
    210                 215                 220

Asp Gln Asn Ile Phe Ser Phe Tyr Leu Ser Arg Asp Pro Asp Ala Gln
225                 230                 235                 240

Pro Gly Gly Glu Leu Met Leu Gly Gly Thr Asp Ser Lys Tyr Tyr Lys
                245                 250                 255

Gly Ser Leu Ser Tyr Leu Asn Val Thr Arg Lys Ala Tyr Trp Gln Val
            260                 265                 270

His Leu Asp Gln Val Glu Val Ala Ser Gly Leu Thr Leu Cys Lys Glu
        275                 280                 285

Gly Cys Glu Ala Ile Val Asp Thr Gly Thr Ser Leu Met Val Gly Pro
    290                 295                 300

Val Asp Glu Val Arg Glu Leu Gln Lys Ala Ile Gly Ala Val Pro Leu
305                 310                 315                 320

Ile Gln Gly Glu Tyr Met Ile Pro Cys Glu Lys Val Ser Thr Leu Pro
                325                 330                 335

Ala Ile Thr Leu Lys Leu Gly Gly Lys Gly Tyr Lys Leu Ser Pro Glu

```
                  340                 345                 350
Asp Tyr Thr Leu Lys Val Ser Gln Ala Gly Lys Thr Leu Cys Leu Ser
            355                 360                 365
Gly Phe Met Gly Met Asp Ile Pro Pro Ser Gly Pro Leu Trp Ile
370                 375                 380
Leu Gly Asp Val Phe Ile Gly Arg Tyr Tyr Thr Val Phe Asp Arg Asp
385                 390                 395                 400
Asn Asn Arg Val Gly Phe Ala Glu Ala Ala Arg Leu
                405                 410

<210> SEQ ID NO 26
<211> LENGTH: 406
<212> TYPE: PRT
<213> ORGANISM: Homo sapien

<400> SEQUENCE: 26

Met Asp Gly Trp Arg Arg Met Pro Arg Trp Gly Leu Leu Leu Leu Leu
1               5                   10                  15
Trp Gly Ser Cys Thr Phe Gly Leu Pro Thr Asp Thr Thr Thr Phe Lys
            20                  25                  30
Arg Ile Phe Leu Lys Arg Met Pro Ser Ile Arg Glu Ser Leu Lys Glu
        35                  40                  45
Arg Gly Val Asp Met Ala Arg Leu Gly Pro Glu Trp Ser Gln Pro Met
    50                  55                  60
Lys Arg Leu Thr Leu Gly Asn Thr Thr Ser Ser Val Ile Leu Thr Asn
65                  70                  75                  80
Tyr Met Asp Thr Gln Tyr Tyr Gly Glu Ile Gly Ile Gly Thr Pro Pro
                85                  90                  95
Gln Thr Phe Lys Val Val Phe Asp Thr Gly Ser Ser Asn Val Trp Val
            100                 105                 110
Pro Ser Ser Lys Cys Ser Arg Leu Tyr Thr Ala Cys Val Tyr His Lys
        115                 120                 125
Leu Phe Asp Ala Ser Asp Ser Ser Ser Tyr Lys His Asn Gly Thr Glu
    130                 135                 140
Leu Thr Leu Arg Tyr Ser Thr Gly Thr Val Ser Gly Phe Leu Ser Gln
145                 150                 155                 160
Asp Ile Ile Thr Val Gly Gly Ile Thr Val Thr Gln Met Phe Gly Glu
                165                 170                 175
Val Thr Glu Met Pro Ala Leu Pro Phe Met Leu Ala Glu Phe Asp Gly
            180                 185                 190
Val Val Gly Met Gly Phe Ile Glu Gln Ala Ile Gly Arg Val Thr Pro
        195                 200                 205
Ile Phe Asp Asn Ile Ile Ser Gln Gly Val Leu Lys Glu Asp Val Phe
    210                 215                 220
Ser Phe Tyr Tyr Asn Arg Asp Ser Glu Asn Ser Gln Ser Leu Gly Gly
225                 230                 235                 240
Gln Ile Val Leu Gly Gly Ser Asp Pro Gln His Tyr Glu Gly Asn Phe
                245                 250                 255
His Tyr Ile Asn Leu Ile Lys Thr Gly Val Trp Gln Ile Gln Met Lys
            260                 265                 270
Gly Val Ser Val Gly Ser Ser Thr Leu Leu Cys Glu Asp Gly Cys Leu
        275                 280                 285
Ala Leu Val Asp Thr Gly Ala Ser Tyr Ile Ser Gly Ser Thr Ser Ser
    290                 295                 300
```

-continued

```
Ile Glu Lys Leu Met Glu Ala Leu Gly Ala Lys Lys Arg Leu Phe Asp
305                 310                 315                 320

Tyr Val Val Lys Cys Asn Glu Gly Pro Thr Leu Pro Asp Ile Ser Phe
                325                 330                 335

His Leu Gly Gly Lys Glu Tyr Thr Leu Thr Ser Ala Asp Tyr Val Phe
            340                 345                 350

Gln Glu Ser Tyr Ser Ser Lys Lys Leu Cys Thr Leu Ala Ile His Ala
        355                 360                 365

Met Asp Ile Pro Pro Pro Thr Gly Pro Thr Trp Ala Leu Gly Ala Thr
    370                 375                 380

Phe Ile Arg Lys Phe Tyr Thr Glu Phe Asp Arg Arg Asn Asn Arg Ile
385                 390                 395                 400

Gly Phe Ala Leu Ala Arg
                405

<210> SEQ ID NO 27
<211> LENGTH: 751
<212> TYPE: DNA
<213> ORGANISM: Homo sapien

<400> SEQUENCE: 27
aaaaaaaaaa cttcattcta aaccaaaaca gagtggattg ggctgcaggc tctatggggt    60
tcgttatgcc aaagtgtcta catgtgccac aacataaaa caaaaccaag ccttggctcg    120
ttctcttctc tcttcaatct ctggaaaaat aagtacatat agttgataac ccctcttagc    180
ttacaggaag cttttttgtat taattgcctt tgaggttatt ttccgccaga cctcaacctg    240
ggtcaaagtg gtacaggaag gcttgcagta tgatggcagg agaatcagcc tggggcctgg    300
ggatgtaacc aagctgtacc cttgagacct ggaaccagag ccacaggccc cttttgtggg    360
tttctctgtg ctctgaatgg gagccagaat tcactaggag gtcatcaacc gatggtcctc    420
acaagcctct tctgaagatg gaaggccttt tgcccgttga ggtagagggg aaggaaatct    480
cctcttttgt acccaatact tatgttgtat tgttggtgcg aaagtaaaaa cactacctct    540
tttgagactt tgcccagggt cctgtgcctg gatgggggtg caggcagcct tgaccacggc    600
tgttcccctc acccaaaaga attatcatcc caacagccaa gacccaacag gtgctgaact    660
gtgcatcaac caggaagagt tctatcccca agctggccac tatcacatat gcttactctt    720
gcttaaaatt aataaatcat gttttgatga g                                   751
```

What is claimed is:

1. An isolated nucleic acid molecule comprising a polynucleotide at least 90% identical to SEQ ID NO:17.

2. The isolated nucleic acid molecule of claim 1 wherein the polynucleotide has a sequence at least 95% identical to SEQ ID NO:17.

3. The isolated nucleic acid molecule of claim 1 wherein the the polynucleotide has the sequence of SEQ ID NO:17.

4. An isolated nucleic acid molecule comprising at least 400 contiguous nucleotides of SEQ ID NO:17.

5. The isolated nucleic acid molecule of claim 4 comprising at least 450 contiguous nucleotides of SEQ ID NO:17.

6. A kit for the diagnosis or detection of cancer in a mammal, said kit comprising an isolated and purified subgenomic polynucleotide which hybridizes to the nucleotide sequence of SEQ ID NO:17 after washing with 0.2×SSC at 65° C. under highly stringent conditions; primers for amplifying SEQ ID NO:17; and, optionally, instructions for using the kit.

7. The kit of claim 6 wherein the cancer is colon cancer.

* * * * *